US011229406B2

(12) United States Patent
Zhong et al.

(10) Patent No.: US 11,229,406 B2
(45) Date of Patent: Jan. 25, 2022

(54) PATIENT-SPECIFIC GLUCOSE PREDICTION SYSTEMS AND METHODS

(71) Applicant: MEDTRONIC MINIMED, INC., Northridge, CA (US)

(72) Inventors: Yuxiang Zhong, Arcadia, CA (US); Pratik Agrawal, Porter Ranch, CA (US); Huzefa F. Neemuchwala, Simi Valley, CA (US); Sinu Bessy Abraham, Gallatin, TN (US); Boyi Jiang, Northridge, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 972 days.

(21) Appl. No.: 15/933,264

(22) Filed: Mar. 22, 2018

(65) Prior Publication Data

US 2018/0271455 A1 Sep. 27, 2018

Related U.S. Application Data

(60) Provisional application No. 62/476,444, filed on Mar. 24, 2017, provisional application No. 62/476,451, (Continued)

(51) Int. Cl.
*A61B 5/00* (2006.01)
*G16H 50/20* (2018.01)
(Continued)

(52) U.S. Cl.
CPC .......... *A61B 5/7275* (2013.01); *A61B 5/0004* (2013.01); *A61B 5/1112* (2013.01);
(Continued)

(58) Field of Classification Search
CPC .... G16H 20/17; G16H 50/20; A61B 5/14532; A61B 5/7275; A61B 5/742;
(Continued)

(56) References Cited

U.S. PATENT DOCUMENTS

| 4,562,751 A | 1/1986 | Nason et al. |
| 4,685,903 A | 8/1987 | Cable et al. |
| (Continued) | | |

FOREIGN PATENT DOCUMENTS

CN 103293324 A 9/2013

OTHER PUBLICATIONS

Daskalaki et al. "An early warning system for hypoglycemic/hyperglycemic events based on fusion of adaptive prediction models." J Diabetes Sci Technol. May 1, 2013;7(3):689-98. (Year: 2013).*

(Continued)

*Primary Examiner* — Meredith Weare
(74) *Attorney, Agent, or Firm* — Lorenz & Kopf, LLP

(57) ABSTRACT

Infusion devices and related medical devices, patient data management systems, and methods are provided for monitoring a physiological condition of a patient. An exemplary method of monitoring a physiological condition of a patient involves obtaining current measurement data for the physiological condition of the patient provided by a sensing arrangement, obtaining a user input indicative of one or more future events associated with the patient, and in response to the user input, determining a prediction of the physiological condition of the patient in the future based at least in part on the current measurement data and the one or more future events using one or more prediction models associated with the patient, and displaying a graphical representation of the prediction on a display device.

13 Claims, 24 Drawing Sheets

Related U.S. Application Data filed on Mar. 24, 2017, provisional application No. 62/476,456, filed on Mar. 24, 2017, provisional application No. 62/476,468, filed on Mar. 24, 2017, provisional application No. 62/476,493, filed on Mar. 24, 2017, provisional application No. 62/476,506, filed on Mar. 24, 2017, provisional application No. 62/476,517, filed on Mar. 24, 2017, provisional application No. 62/534,051, filed on Jul. 18, 2017.

(51) Int. Cl.
| | |
|---|---|
| A61B 5/145 | (2006.01) |
| G16H 20/17 | (2018.01) |
| A61M 5/172 | (2006.01) |
| G06F 16/28 | (2019.01) |
| G06F 16/22 | (2019.01) |
| G06F 16/332 | (2019.01) |
| G16H 20/70 | (2018.01) |
| A61M 5/142 | (2006.01) |
| G16H 50/50 | (2018.01) |
| G16H 50/30 | (2018.01) |
| G16H 20/10 | (2018.01) |
| G16H 50/70 | (2018.01) |
| G16H 20/30 | (2018.01) |
| A61B 5/11 | (2006.01) |
| G16H 10/60 | (2018.01) |
| G16H 40/63 | (2018.01) |
| G16H 20/60 | (2018.01) |

(52) U.S. Cl.
CPC .......... *A61B 5/14532* (2013.01); *A61B 5/486* (2013.01); *A61B 5/4833* (2013.01); *A61B 5/4839* (2013.01); *A61B 5/7264* (2013.01); *A61B 5/742* (2013.01); *A61B 5/7405* (2013.01); *A61B 5/746* (2013.01); *A61B 5/749* (2013.01); *A61B 5/7455* (2013.01); *A61M 5/142* (2013.01); *A61M 5/14212* (2013.01); *A61M 5/172* (2013.01); *A61M 5/1723* (2013.01); *G06F 16/2264* (2019.01); *G06F 16/288* (2019.01); *G06F 16/3329* (2019.01); *G16H 10/60* (2018.01); *G16H 20/10* (2018.01); *G16H 20/17* (2018.01); *G16H 20/30* (2018.01); *G16H 20/60* (2018.01); *G16H 20/70* (2018.01); *G16H 40/63* (2018.01); *G16H 50/20* (2018.01); *G16H 50/30* (2018.01); *G16H 50/50* (2018.01); *G16H 50/70* (2018.01); *A61B 5/1118* (2013.01); *A61B 5/4848* (2013.01); *A61B 5/4866* (2013.01); *A61B 2560/0252* (2013.01); *A61B 2560/0257* (2013.01); *A61B 2562/029* (2013.01); *A61M 2205/3303* (2013.01); *A61M 2205/3584* (2013.01); *A61M 2205/3592* (2013.01); *A61M 2205/50* (2013.01); *A61M 2205/502* (2013.01); *A61M 2205/505* (2013.01); *A61M 2205/80* (2013.01); *A61M 2230/201* (2013.01)

(58) Field of Classification Search
CPC ... A61B 5/7264; A61B 5/4848; A61B 5/4866; A61B 5/1118
See application file for complete search history.

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,272,480 B1* | 8/2001 | Tresp ................... G06N 3/049 706/44 |
| 6,317,731 B1 | 11/2001 | Luciano |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |

(56) References Cited

U.S. PATENT DOCUMENTS

| | | | |
|---|---|---|---|
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,474,332 B2 | 7/2013 | Bente, IV | |
| 8,674,288 B2 | 3/2014 | Hanson et al. | |
| 8,762,624 B2 | 6/2014 | Binz et al. | |
| 8,838,513 B2 | 9/2014 | Sudharsan | |
| 2003/0208113 A1* | 11/2003 | Mault | A61B 5/14532 600/316 |
| 2005/0192492 A1 | 9/2005 | Cho et al. | |
| 2006/0031094 A1 | 2/2006 | Cohen et al. | |
| 2006/0253296 A1 | 11/2006 | Liisberg et al. | |
| 2007/0123819 A1 | 5/2007 | Mernoe et al. | |
| 2008/0126130 A1 | 5/2008 | Miller et al. | |
| 2009/0006129 A1 | 1/2009 | Thukral et al. | |
| 2009/0305317 A1* | 12/2009 | Brauer | C12Q 1/004 435/14 |
| 2009/0312621 A1 | 12/2009 | Verbitskiy et al. | |
| 2010/0160861 A1 | 6/2010 | Causey, III et al. | |
| 2011/0195970 A1 | 8/2011 | Cincotta | |
| 2012/0328594 A1 | 12/2012 | McKenna et al. | |
| 2013/0338630 A1 | 12/2013 | Agrawal et al. | |
| 2014/0006044 A1 | 1/2014 | Pradhan et al. | |
| 2014/0012511 A1† | 1/2014 | Mensinger | |
| 2014/0066889 A1 | 3/2014 | Grosman et al. | |
| 2014/0149329 A1 | 5/2014 | Shaw | |
| 2014/0172449 A1 | 6/2014 | Reinke et al. | |
| 2014/0187887 A1* | 7/2014 | Dunn | G16H 50/30 600/365 |
| 2014/0309511 A1* | 10/2014 | Stal | A61B 5/7267 600/365 |
| 2015/0095044 A1 | 4/2015 | Hartman et al. | |
| 2015/0111188 A1 | 4/2015 | Maruthurkkara | |
| 2015/0220702 A1 | 8/2015 | Hovorka | |
| 2015/0248540 A1 | 9/2015 | Lovejoy et al. | |
| 2016/0063191 A1 | 3/2016 | Vesto et al. | |
| 2017/0053101 A1 | 2/2017 | Booth et al. | |
| 2017/0068789 A1 | 3/2017 | Dalton et al. | |
| 2017/0091419 A1 | 3/2017 | Hoglund et al. | |
| 2017/0181711 A1 | 6/2017 | Cheng et al. | |
| 2017/0209657 A1 | 7/2017 | Levings et al. | |
| 2017/0235894 A1 | 8/2017 | Cox et al. | |
| 2017/0286622 A1 | 10/2017 | Cox et al. | |

OTHER PUBLICATIONS

Eleni I Georga et al.: "Knowledge-Oriented Applications in Data Mining, Chapter 17: Glucose Prediction in Type 1 and Type 2 Diabetic Patients Using Data Driven Techniques", Knowledge-Oriented Applications in Data Mining, pp. 277-297, Jan. 21, 2011 (Jan. 21, 2011), XP002740540, ISBN: 978-953-307-154-1 Retrieved from the Internet: URL:http://cdn.intechopen.com/pdfs-wm/13173. pdf [retrieved on Jun. 5, 2015].

Fredrik Stahl et al: "Ensemble Glucose Prediction in Insulin-Dependent Diabetes" In: "Advancements of Medical Electronics", Jan. 1, 2014 (Jan. 1, 2014), Springer India, New Delhi, XP055479229, ISSN: 2195-271X, ISBN: 978-81-32-22256-9 pp. 37-71, DOI: 10.1007/978-3-642-54464-4_2.

* cited by examiner
† cited by third party

PATIENT-SPECIFIC GLUCOSE PREDICTION SYSTEMS AND METHODS

CROSS-REFERENCE TO RELATED APPLICATION(S)

This application claims the benefit of the following United States Provisional Patent Applications: U.S. Provisional Patent Application Ser. No. 62/476,444, filed Mar. 24, 2017; U.S. Provisional Patent Application Ser. No. 62/476,451, filed Mar. 24, 2017; U.S. Provisional Patent Application Ser. No. 62/476,456, filed Mar. 24, 2017; U.S. Provisional Patent Application Ser. No. 62/476,468, filed Mar. 24, 2017; U.S. Provisional Patent Application Ser. No. 62/476,493, filed Mar. 24, 2017; U.S. Provisional Patent Application Ser. No. 62/476,506, filed Mar. 24, 2017; U.S. Provisional Patent Application Ser. No. 62/476,517, filed Mar. 24, 2017; and U.S. Provisional Patent Application Ser. No. 62/534,051, filed Jul. 18, 2017, each of which is incorporated by reference herein in its entirety.

TECHNICAL FIELD

Embodiments of the subject matter described herein relate generally to medical devices and related patient monitoring systems, and more particularly, embodiments of the subject matter relate to database systems facilitating improved patient-specific queries, predictions, and recommendations.

BACKGROUND

Infusion pump devices and systems are relatively well known in the medical arts, for use in delivering or dispensing an agent, such as insulin or another prescribed medication, to a patient. Use of infusion pump therapy has been increasing, especially for delivering insulin for diabetics. Continuous insulin infusion provides greater control of a diabetic's condition, and hence, control schemes are being developed that allow insulin infusion pumps to monitor and regulate a patient's blood glucose level in a substantially continuous and autonomous manner, for example, overnight while the patient is sleeping.

Regulating blood glucose level is complicated by variations in the response time for the type of insulin being used along with each patient's individual insulin response. Furthermore, a patient's daily activities and experiences may cause that patient's insulin response to vary throughout the course of a day or from one day to the next. Accordingly, there is a need to facilitate improved glucose control that accounts for the numerous different variables in a personalized manner. Moreover, the effects and efficacy of different therapy regimen may vary from one patient to the next. Thus, it is also desirable to provide a better understanding of how an individual patient's condition is likely to be affected by various actions, or how different therapies or actions could improve regulation of the patient's condition. Other desirable features and characteristics of the methods, devices and systems described herein will become apparent from the subsequent detailed description and the appended claims, taken in conjunction with the accompanying drawings and the preceding background.

BRIEF SUMMARY

Infusion devices and related medical devices, patient data management systems, and methods are provided for monitoring a physiological condition of a patient. One embodiment of a method of monitoring a physiological condition of a patient involves obtaining, at a computing device, current measurement data for the physiological condition of the patient provided by a sensing arrangement, obtaining, at the computing device, a user input indicative of one or more future events associated with the patient, and in response to the user input, determining a prediction of the physiological condition of the patient in the future based at least in part on the current measurement data and the one or more future events using one or more prediction models associated with the patient, and displaying, at the computing device, a graphical representation of the prediction on a display device.

In another embodiment, an apparatus of an electronic device is provided. The electronic device includes a communications interface to receive current measurement data for a physiological condition of a patient from a sensing arrangement, a display device having a graphical user interface display presented thereon, a user interface to obtain a user input indicative of one or more future events, and a control system coupled to the communications interface, the display device, and the user interface to determine a prediction of the physiological condition of the patient in the future based at least in part on the current measurement data and the one or more future events using one or more prediction models associated with the patient, and display a graphical representation of the prediction within the graphical user interface display on the display device.

In another embodiment, a method of monitoring a glucose level of a patient is provided. The method involves obtaining, at a computing device from a glucose sensing arrangement, current sensor glucose measurement data for the patient, obtaining, at the computing device via a user interface, a user input indicative of one or more future events for the patient, determining, at the computing device, a simulated glucose level in the future for the patient based at least in part on the current sensor glucose measurement data and the one or more future events using a plurality of different prediction models associated with the patient, wherein the plurality of different prediction models includes an hourly forecasting model associated with the patient, and displaying, on a display device associated with the computing device, a graphical representation of the simulated glucose level with respect to time in the future.

In another embodiment, a method of monitoring a physiological condition of a patient involves obtaining, from a sensing arrangement, current measurement data for the physiological condition of the patient, predicting one or more events likely influence the physiological condition of the patient at one or more different times in the future based at least in part on historical event data associated with the patient, determining a plurality of forecast values for the physiological condition of the patient associated with a plurality of different time periods in the future based at least in part on the current measurement data and the one or more events using a forecasting model associated with the patient, and displaying, on a display device, the plurality of forecast values with respect to the plurality of different time periods in the future.

In another embodiment, a system is provided that includes a display device, a sensing arrangement to obtain current measurement data for a physiological condition of a patient, and a control system coupled to the display device and the sensing arrangement to determine a plurality of forecast hourly average values for the physiological condition of the patient in the future based at least in part on the current measurement data using an hourly forecasting model associated with the patient and display the plurality of forecast hourly average values on the display device.

In another embodiment, a method of monitoring a glucose level of a patient is provided. The method involves determining an hourly forecasting model for the patient based at least in part on a relationship between historical glucose measurement data for the patient and historical event data associated with the patient, obtaining, from a glucose sensing arrangement, current glucose measurement data for the patient, predicting one or more events likely influence the glucose level of the patient at one or more different times in the future based at least in part on the historical event data associated with the patient, determining a plurality of hourly forecast average glucose values for the patient in the future based at least in part on the current glucose measurement data and the one or more events using the hourly forecasting model associated with the patient, and displaying, on a display device, a graphical representation of the plurality of hourly forecast average glucose values in the future.

In another embodiment, a method of monitoring a physiological condition of a patient involves obtaining, from a sensing arrangement, current measurement data for the physiological condition of the patient, determining a first plurality of predicted values for the physiological condition of the patient in the future based at least in part on the current measurement data using a first prediction model, determining a second plurality of predicted values for the physiological condition of the patient in the future based at least in part on the current measurement data using a second prediction model different from the first prediction model, determining an ensemble prediction for the physiological condition of the patient with respect to time in the future based at least in part on the first plurality of predicted values, the second plurality of predicted values, and weighting factors associated with the respective first and second prediction models, wherein the weighting factors vary with respect to the time in the future based on a relationship between a first reliability metric associated with the first prediction model and a second reliability metric associated with the second prediction model, and displaying, on a display device, a graphical indication of the ensemble prediction for the physiological condition of the patient with respect to the time in the future.

Another method of monitoring a physiological condition of a patient involves obtaining, from a sensing arrangement, current measurement data for the physiological condition of the patient, determining a plurality of predicted values indicative of the physiological condition for a time in the future based at least in part on the current measurement data using a plurality of different prediction models associated with the patient, wherein each predicted value of the plurality of predicted values is associated with a respective prediction model of the plurality of different prediction models, determining, for each respective prediction model of the plurality of different prediction models, a reliability metric associated with the respective prediction model based at least in part on a relationship between the time in the future and a current time of day, determining, for each respective prediction model of the plurality of different prediction models, a weighting factor associated with the respective prediction model based at least in part on the reliability metric associated with the respective prediction model, determining an ensemble predicted value for the physiological condition of the patient as a weighted average of the respective predicted values of the plurality of predicted values and the weighting factors associated with the respective prediction models, and displaying a graphical indication of the ensemble predicted value for the physiological condition of the patient in association with the time in the future.

In another embodiment, an apparatus for an electronic device is provided. The electronic device includes a communications interface to receive current measurement data for a physiological condition of a patient from a sensing arrangement, a display device having a graphical user interface display including a graphical representation of the current measurement data, a user interface to obtain a user input adjusting the graphical user interface display to view into the future, and a control system coupled to the communications interface, the display device, and the user interface to determine a first plurality of predicted values for the physiological condition of the patient in the future based at least in part on the current measurement data using a first prediction model, determine a second plurality of predicted values for the physiological condition of the patient in the future based at least in part on the current measurement data using a second prediction model different from the first prediction model, determine an ensemble prediction for the physiological condition of the patient with respect to time in the future based at least in part on the first plurality of predicted values and the second plurality of predicted values, and display a graphical representation of the ensemble prediction on the graphical user interface display in response to the user input.

In another embodiment, a database system is provided. The database system includes a database to maintain data pertaining to a plurality of entities and a computing device coupled to the database to identify relationships between different pairs of the plurality of entities, generate metadata defining a graph structure maintaining the relationships between the different entities of the plurality of entities for a plurality of different logical layers, and store the metadata in the database.

In another embodiment, a method of managing a database maintaining data pertaining to a plurality of patients is provided. The method involves analyzing, by a computing device, a graph data structure for a logical layer in the database, the graph data structure being defined by metadata in the database and the graph data structure comprising a plurality of entities, wherein each entity of the plurality of entities maintains a logical relationship with one or more fields of observational data associated with a respective patient of the plurality of patients, identifying, by the computing device, a relationship between a pair of entities of the plurality of entities within the logical layer, and updating, by the computing device, the metadata in the database to create a link between the pair of entities.

In another embodiment, a system involves a plurality of medical devices to obtain observational data pertaining to a plurality of patients, a database to maintain data pertaining to a plurality of entities, wherein each entity of the plurality of entities maintains a logical relationship between one or more fields of the observational data stored in the database, and a computing device coupled to the database to identify relationships between different entities of the plurality of entities, generate metadata defining a graph structure maintaining the relationships between the different entities of the plurality of entities for a plurality of different logical layers, and store the metadata in the database.

In another embodiment, a method of querying a database is provided. The method involves receiving, by a computing device coupled to the database, an input query from a client device, identifying, by the computing device, a logical layer of a plurality of different logical layers of the database for searching based at least in part on the input query, generating, by the computing device, a query statement for searching the identified logical layer of the plurality of different logical layers of the database based at least in part on the input query, querying the identified logical layer of the database using the query statement to obtain result data, and providing, by the computing device to the client device, a search result influenced by the result data.

In another embodiment, a database system is provided. The database system includes a database to maintain data pertaining to a plurality of entities and metadata defining a graph structure maintaining relationships between different entities of the plurality of entities for each of a plurality of different logical layers, a client device coupled to a network to transmit a conversational input from a user of the client device, and a computing device coupled to the database and the network to receive the conversational input from the client device, determines a logical layer of the plurality of different logical layers of the database for searching based at least in part on the conversational input, generate a query statement for searching the identified logical layer of the plurality of different logical layers of the database based at least in part on the conversational input to obtain result data from the logical layer of the database, and provide a search result influenced by the result data to the client device over the network.

In another embodiment, a method of querying a database involves providing, at a client electronic device, a graphical user interface display prompting conversational interaction by a user, receiving, at the client electronic device, a conversational input from the user, communicating, from the client electronic device to a remote device over a network, the conversational input, wherein the remote device analyzes the conversational input to identify a logical layer of a plurality of different logical layers of the database for searching based at least in part on the conversational input and queries the identified logical layer of the database to obtain result data, and providing, at the client electronic device, a conversational search result within the graphical user interface display responsive to the conversational input, wherein the conversational search result is influenced by the result data.

In another embodiment, an apparatus for an infusion device is provided. The infusion device includes an actuation arrangement operable to deliver fluid to a user, the fluid influencing a physiological condition of the user, a communications interface to receive measurement data indicative of the physiological condition of the user, a sensing arrangement to obtain contextual measurement data, and a control system coupled to the actuation arrangement, the communications interface and the sensing arrangement to determine a command for autonomously operating the actuation arrangement in a manner that is influenced by the measurement data and the contextual measurement data and autonomously operate the actuation arrangement in accordance with the command to deliver the fluid to the user.

In another embodiment, a method of operating an infusion device to regulate a physiological condition of a patient is provided. The method involves obtaining, at the infusion device, measurement data indicative of the physiological condition from a first sensing arrangement, determining, at the infusion device, a delivery command for autonomously operating an actuation arrangement of the infusion device to deliver fluid influencing the physiological condition to the patient, obtaining, at the infusion device, contextual measurement data from a second sensing arrangement of the infusion device, adjusting the delivery command in a manner that is influenced by the contextual measurement data to obtain an adjusted delivery command, and autonomously operating the actuation arrangement to deliver the fluid in accordance with the adjusted delivery command.

In another embodiment, a method of monitoring a physiological condition of a patient involves obtaining, by a computing device, measurement data pertaining to the physiological condition of the patient from a sensing arrangement, obtaining, by the computing device, medical record data associated with the patient from a database, determining, by the computing device, a risk score associated with the patient for a medical condition based at least in part on the measurement data, the medical record data, and one or more relationships between population measurement data and population medical record data, and initiating one or more actions at the computing device based at least in part on the risk score.

In another embodiment, a system is provided that includes a sensing arrangement to obtain measurement data pertaining to a physiological condition of a patient, a database to maintain medical record data associated with the patient, population measurement data associated with a plurality of patients, and population medical record data associated with the plurality of patients, and a computing device communicatively coupled to the sensing arrangement and the database to determine a risk score associated with the patient for a medical condition based at least in part on the measurement data, the medical record data, and one or more relationships between the population measurement data and the population medical record data and perform one or more actions when the risk score is greater than a threshold.

In another embodiment, a method of monitoring a patient involves obtaining, from a database, population glucose measurement data associated with a plurality of patients, obtaining, from the database, population medical record data associated with the plurality of patients, determining a risk model for a medical condition based on relationships between population glucose measurement data and population medical record data for a subset of the plurality of patients having the medical condition, obtaining, from an interstitial glucose sensing arrangement, sensor glucose measurement data for the patient, obtaining, from the database, medical record data associated with the patient, determining a risk score associated with the patient for the medical condition based at least in part on the sensor glucose measurement data and the medical record data using the risk model, and generating a therapy recommendation for the patient when the risk score is greater than a threshold.

In another embodiment, a method of managing a physiological condition of a patient involves obtaining, by a computing device, measurement data pertaining to the physiological condition of the patient from a sensing arrangement, obtaining, by the computing device, medical records data associated with the patient from a database, classifying, by the computing device, the patient into a patient group based at least in part on the measurement data and the medical records data, obtaining, by the computing device, a plurality of different uplift models associated with the patient group, wherein each uplift model of the plurality of different uplift models corresponds to a respective therapy intervention of a plurality of different therapy interventions, determining, by the computing device, a plurality of uplift metric values associated with the patient for the plurality of different therapy interventions based on the measurement data and the medical record data using the plurality of different uplift models, and providing, by the computing device, an indication of a recommended therapy intervention for the patient based at least in part on a respective uplift metric value associated with the recommended therapy intervention.

In another embodiment, a method of managing a physiological condition of a patient involves obtaining, by a computing device coupled to a database, population measurement data associated with a plurality of patients from the database, obtaining, by the computing device, population medical record data associated with the plurality of patients from the database, determining, by the computing device, a patient group comprising a subset of the plurality of patients for modeling based on at least one of a subset of the population measurement data associated with the subset of the plurality of patients and a subset of the population medical record data associated with the subset of the plurality of patients, determining, by the computing device, a plurality of different uplift models associated with the patient group for different therapy interventions based at least in part on one or more relationships between the subset of the population measurement data and the subset of the population medical record data associated with the subset of patients, obtaining measurement data pertaining to the physiological condition of the patient from a sensing arrangement, obtaining medical record data associated with the patient from the database, determining a plurality of uplift metric values associated with the patient based on the measurement data and the medical record data using the plurality of different uplift models, selecting a recommended therapy intervention of the different therapy interventions based at least in part on the plurality of uplift metric values, and providing an indication of the recommended therapy intervention for the patient.

In another embodiment, a system is provided that includes a sensing arrangement to obtain measurement data pertaining to a physiological condition of a patient, a database to maintain medical record data associated with the patient and a plurality of different uplift models associated with a patient group based on relationships between population measurement data and population medical record data associated with a plurality of patients, wherein each uplift model of the plurality of different uplift models corresponds to a respective therapy intervention of a plurality of different therapy interventions, and a computing device communicatively coupled to the sensing arrangement and the database to classify the patient into the patient group based at least in part on the measurement data and the medical records data, determine a plurality of uplift metric values associated with the patient for the plurality of different therapy interventions based on the measurement data and the medical record data using the plurality of different uplift models, and generate a user notification of a recommended therapy intervention for the patient based at least in part on a respective uplift metric value associated with the recommended therapy intervention.

In another embodiment, a method of managing a physiological condition of a patient involves obtaining, by a computing device, measurement data pertaining to the physiological condition of the patient from a sensing arrangement, obtaining, by the computing device, medical records data associated with the patient from a database, obtaining, by the computing device, a plurality of different adherence models associated with a plurality of different therapy regimens, wherein each adherence model of the plurality of different adherence models corresponds to a respective therapy regimen of a plurality of different therapy regimens, determining, by the computing device, a plurality of adherence metric values associated with the patient for the plurality of different therapy regimens based on the measurement data and the medical record data using the plurality of different adherence models, and providing, by the computing device, an indication of a recommended therapy regimen for the patient based at least in part on a respective adherence metric value associated with the recommended therapy regimen.

In another embodiment, a method of managing a physiological condition of a patient involves obtaining, by a computing device, population medical records data for a plurality of patients prescribed a therapy regimen, obtaining, by the computing device, population medical claims data for the plurality of patients, obtaining, by the computing device, population measurement data for the plurality of patients, determining, by the computing device, an adherence model based at least in part on a relationship between the population medical claims data, the population medical records data, and the population measurement data, obtaining, by the computing device, measurement data pertaining to the physiological condition of the patient from a sensing arrangement, obtaining, by the computing device, medical records data associated with the patient from the database, determining, by the computing device, an adherence metric value for the therapy regimen for the patient based at least in part on the measurement data and the medical records data using the adherence model, and recommending, by the computing device, the therapy regimen for the patient based on the adherence metric value.

In another embodiment, a system is provided that includes a sensing arrangement to obtain measurement data pertaining to a physiological condition of a patient, a database to maintain medical record data associated with the patient and a plurality of different adherence models associated with a plurality of different therapy regimens, wherein each adherence model of the plurality of different adherence models corresponds to a respective therapy regimen of a plurality of different therapy regimens, and a computing device communicatively coupled to the sensing arrangement and the database to determine a plurality of adherence metric values associated with the patient for the plurality of different therapy regimens based on the measurement data and the medical record data using the plurality of different adherence models and generate a user notification of a recommended therapy regimen for the patient based at least in part on a respective adherence metric value associated with the recommended therapy regimen.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
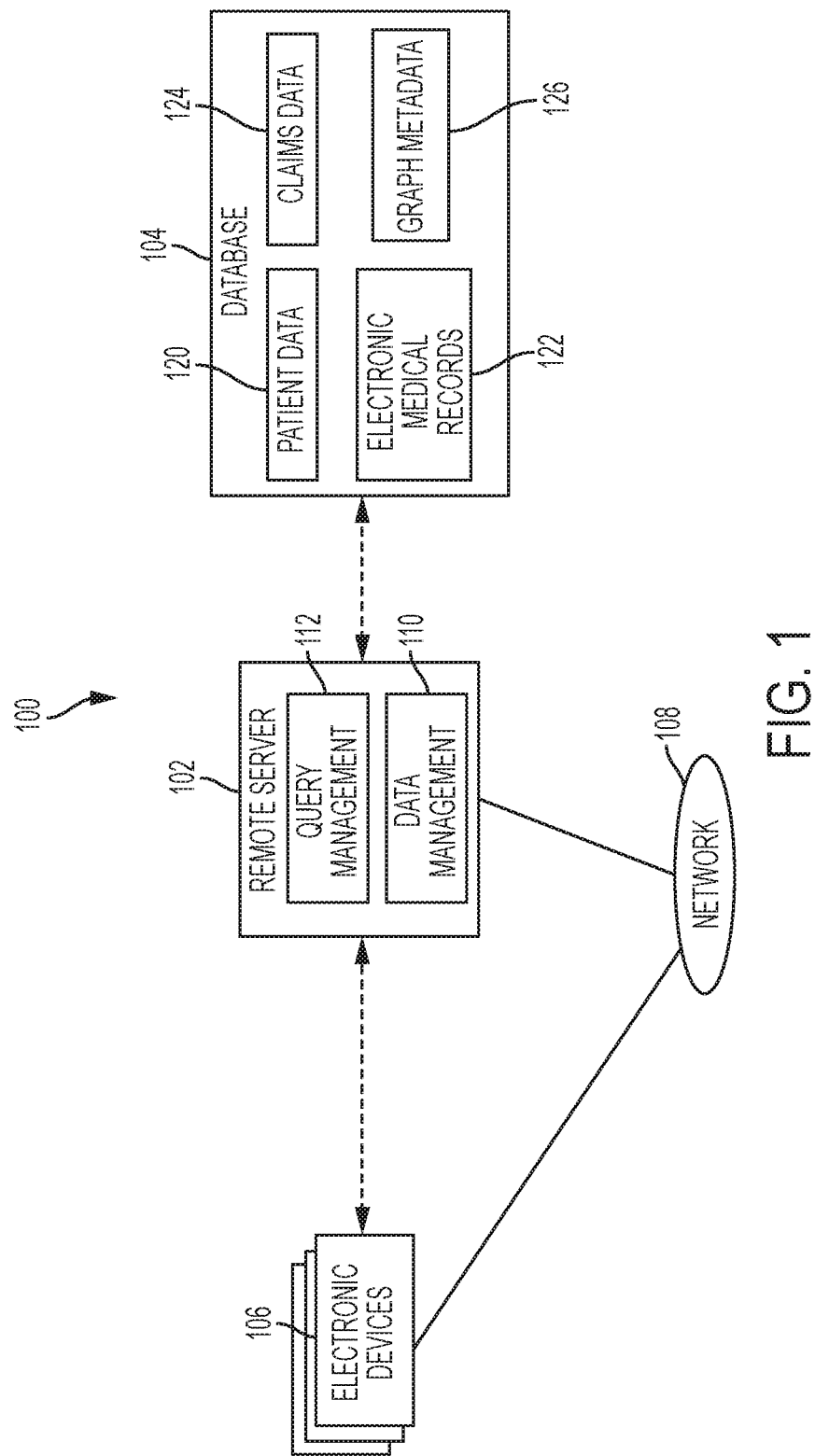
FIG. 1 depicts an exemplary embodiment of a patient data management system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

For purposes of explanation, the subject matter may be described herein primarily in the context of infusion systems and devices configured to support monitoring and/or regulating a glucose level in the body of the user in a personalized and/or context-sensitive manner. That said, the subject matter described herein is not necessarily limited to glucose regulation or insulin infusion, and in practice, could be implemented in an equivalent manner with respect to any number of other medications, physiological conditions, and/or the like.

While the subject matter described herein can be implemented in the context of any electronic device, exemplary embodiments described below are implemented in connection with medical devices, such as portable electronic medical devices. Although many different applications are possible, the following description may primarily focus on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference. A fluid infusion device generally includes a motor or other actuation arrangement that is operable to linearly displace a plunger (or stopper) of a reservoir provided within the fluid infusion device to deliver a dosage of fluid, such as insulin, to the body of a user. In one or more exemplary embodiments, delivery commands (or dosage commands) that govern operation of the motor are determined in a substantially autonomous manner and on a substantially continual basis based on a difference between a measured value for a physiological condition in the body of the user and a target value using closed-loop control to regulate the measured value to the target value.

As described in greater detail below in the context of FIGS. 1-5, in one or more embodiments, historical observational patient data (e.g., measurement data, insulin delivery data, event log data, contextual data, and the like), electronic medical records data, and medical insurance claims data associated with a plurality of different patients are stored or otherwise maintained in a database and organized into a plurality of different logical layers. Each logical layer has its own associated directed graph data structure that maintains associations or relationships between different entities within that logical layer. In this regard, an entity generally represents a container or logical grouping of fields, attributes or other information characterizing the entity. Thus, an entity may maintain a logical association between one or more fields of a patient's historical observational data, the patient's electronic medical records data and/or the patient's medical insurance claims data. For example, a patient identifier and one or more additional fields of data associated with an individual patient may be mapped to different entities within a particular logical database layer, which in turn function as nodes within the directed graph data structure associated with that logical database layer that are linked to other nodes (or entities) within that logical database layer. Thus, similarities or commonalities between different patients or entities within a logical database layer may be utilized to establish links between different patients, lifestyle events, therapy regimens, patient outcomes, and the like, which, in turn, may be utilized to provide improved recommendations pertaining to management of a given patient's condition or otherwise improve the control, regulation, or understanding of a given patient's condition. Similarly, in some embodiments, similarities, commonalities, or causalities may be utilized to establish links between an entity within one logical database layer with another entity in a different logical database layer, thereby establishing links or edges that span logical database layers.

Links or edges between different nodes (or entities) may be initially created when the corresponding data for an entity is loaded, created, or otherwise instantiated in the database. For example, when a new patient is introduced into the database system, a corresponding entity for the patient may be created within a logical database layer for patients. Thereafter, the logical database layer may be searched to identify other entities that are related to or associated with some aspect of that new entity. For example, if the new patient's entity includes an identifier for the patient's healthcare provider, a bidirectional link may be created to the node corresponding to an existing entity associated with the patient's healthcare provider (which may be in the same or different logical layer of the database).

In one or more exemplary embodiments, for each logical database layer, the entities or nodes in the graph data structure associated with that layer are periodically analyzed to identify and create new causal or logical relationships between different nodes of the graph data structure. In one or more embodiments, a generative recurrence neural network or other machine learning or artificial intelligence techniques may periodically scan nodes of the graph data structure to identify cause and effect pairs and establish causality links (or edges) between such nodes of the graph data structure. For example, directional links between entities corresponding to different types of meals and entities corresponding to different types of glucose excursion events (e.g., a hyperglycemic event, a hypoglycemic event, acute diabetic ketoacidosis, and/or the like) may be created in response to a causality engine employing machine learning identifying a causal relationship based on a common sequence of events occurring with respect to one or more patients. In one or more embodiments, generative recurrence neural network techniques are applied by randomly starting from different outcome nodes of interest and backtracking links or edges to that node in a "rule-less" manner to establish whether specific patterns or sequences lead to that particular outcome node. Additionally, query logs associated with queries executed on or at a particular logical database layer may be analyzed to detect repeated associations or query paths involving at least a threshold number of nodes to establish new edges between end nodes of the query paths to improve query performance. In some embodiments, new edges or relationships between entities or nodes in the graph data structure may also be established manually (e.g., based upon new research, clinical evidence, data scraping and manual verification, or other external knowledge).

As described in greater detail below in the context of FIGS. 3-5, the different logical database layers allow for the observational patient data, electronic medical records data, and medical insurance claims data to be effectively translated into different forms with different interrelationships between different subsets of data, thereby accommodating different types of queries. Moreover, the query results may be more personalized or otherwise yield a better patient outcome, recommendation, or understanding of a patient's physiological condition. For example, natural language processing or other artificial intelligence techniques may be applied to an input query or search string to determine an intent or objective associated with the input query, and based thereon, identify one or more of the logical database layers for searching based on the intent of the query. Query statements are then constructed and executed on the identified logical database layers to obtain results for the input query. In one or more embodiments, the initial query results are filtered or otherwise parsed based on information pertaining to a current operational context (e.g., time of day, day of week, geographic location, environmental conditions, and/or the like) to obtain context-sensitive query results, which are then output or otherwise provided in response to the input query.

As described in greater detail below primarily in the context of FIGS. 3-7, In one or more embodiments, a medical device, such as an infusion device, a sensing device, a monitoring device, or the like, includes or otherwise supports a user interface capable of receiving a conversational input query, which, in turn, is parsed or otherwise analyzed at the medical device to obtain the input query to be analyzed for purposes of identifying logical database layers for searching and generating corresponding query statements. For example, in one or more embodiments, a medical device includes a microphone or similar audio input device that is adapted to receive an audio input from a user, which, in turn is processed, parsed, or otherwise analyzed to identify a conversational input query within the audio input. The query results may subsequently be presented or otherwise provided to the user in a conversational manner or otherwise within the context of a conversation or dialog with the user within the user interface. Thus, a patient or user may be capable of conversationally interacting with and querying the database system, which, in turn, is capable of being transformed to allow the queries to be executed on different logical layers in an expeditious manner and provide results that are personalized and context-sensitive while also leveraging interrelationships across different types and subsets of data (e.g., different patients with similar demographic characteristics, different patients with similar medical histories, different patients with similar therapy regimen, and/or the like).

Diabetes Intelligence Network

FIG. 1 depicts an exemplary embodiment of a patient data management system 100 that includes, without limitation, a computing device 102 coupled to a database 104 that is also communicatively coupled to one or more electronic devices 106 over a communications network 108, such as, for example, the Internet, a cellular network, a wide area network (WAN), or the like. It should be appreciated that FIG. 1 depicts a simplified representation of a patient data management system 100 for purposes of explanation and is not intended to limit the subject matter described herein in any way.

In exemplary embodiments, the electronic devices 106 include one or more medical devices, such as, for example, an infusion device, a sensing device, a monitoring device, and/or the like. Additionally, the electronic devices 106 may include any number of non-medical client electronic devices, such as, for example, a mobile phone, a smartphone, a tablet computer, a smart watch, or other similar mobile electronic device, or any sort of electronic device capable of communicating with the computing device 102 via the network 108, such as a laptop or notebook computer, a desktop computer, or the like. One or more of the electronic devices 106 may include or be coupled to a display device, such as a monitor, screen, or another conventional electronic display, capable of graphically presenting data and/or information pertaining to the physiological condition of a patient. Additionally, one or more of the electronic devices 106 also includes or is otherwise associated with a user input device, such as a keyboard, a mouse, a touchscreen, a microphone, or the like, capable of receiving input data and/or other information from a user of the electronic device 106.

In exemplary embodiments, one or more of the electronic devices 106 transmits, uploads, or otherwise provides data or information to the computing device 102 for processing at the computing device 102 and/or storage in the database 104. For example, when an electronic device 106 is realized as a sensing device, monitoring device, or other device that includes sensing element is inserted into the body of a patient or otherwise worn by the patient to obtain measurement data indicative of a physiological condition in the body of the patient, the electronic device 106 may periodically upload or otherwise transmit the measurement data to the computing device 102. In other embodiments, when the electronic device 106 is realized as an infusion device or similar device capable of delivering a fluid or medicament to a patient, the electronic device 106 may periodically upload or otherwise transmit delivery data indicating the timing and amounts of the fluid or medicament being delivered to the patient. In yet other embodiments, client electronic device 106 may be utilized by a patient to manually define, input or otherwise log meals, activities, or other events experienced by the patient and then transmit, upload, or otherwise provide such event log data to the computing device 102.

The computing device 102 generally represents a server or other remote device configured to receive data or other information from the electronic devices 106, store or otherwise manage data in the database 104, and analyze or otherwise monitor data received from the electronic devices 106 and/or stored in the database 104, as described in greater detail below. In practice, the computing device 102 may reside at a location that is physically distinct and/or separate from the electronic devices 106, such as, for example, at a facility that is owned and/or operated by or otherwise affiliated with a manufacturer of one or more medical devices utilized in connection with the patient data management system 100. For purposes of explanation, but without limitation, the computing device 102 may alternatively be referred to herein as a server, a remote server, or variants thereof. The server 102 generally includes a processing system and a data storage element (or memory) capable of storing programming instructions for execution by the processing system, that, when read and executed, cause processing system to create, generate, or otherwise facilitate the applications or software modules configured to perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random access memory (RAM), read only memory (ROM), flash memory, magnetic or optical mass storage, or any other suitable non-transitory short or long term data storage or other computer-readable media, and/or any suitable combination thereof.

In exemplary embodiments, the database 104 is utilized to store or otherwise maintain historical observational patient data 120, electronic medical records data 122, and medical insurance claims data 124 for a plurality of different patients. In this regard, a subset of patients having associated data in one of the data sets 120, 122, 124 may also have associated data in another one of the data sets 120, 122, 124. That is, some but not necessarily all of the patients having associated with one of the data sets 120, 122, 124 may be common to another of the data sets 120, 122, 124. In exemplary embodiments, the database 104 also stores or maintains metadata 126 utilized to characterize or otherwise define directed graph data structures corresponding to different logical layers within the database 104. In this regard, the graph metadata 126 may define the nodes (or entities) that make up the graph data structure associated with a particular logical database layer, with each of those nodes (or entities) being mapped to one or more fields of the sets of data 120, 122, 124. Additionally, the graph metadata 126 characterizes or defines the edges or links between nodes within the graph data structure associated with a particular logical database layer that establish the logical or causal relationship between nodes within that logical database layer. In various embodiments, a node (or entity) may exist in multiple different logical database layers, or a node (or entity) in one logical database layer may be linked to another node (or entity) in a different logical database layer.

In the illustrated embodiment, the server 102 implements or otherwise executes a data management application 110 that receives or otherwise obtains data from the electronic devices 106, stores the received data in the database 104, generates or otherwise creates the entities logically associating different fields of the stored data 120, 122, 124. The data management application 110 also generates or otherwise creates the graph metadata 126 maintaining relationships between the different entities in the database 104, as described in greater detail below in the context of FIGS. 2-5. In the illustrated embodiment, the server 102 also implements or otherwise executes a query management application 112 that receives or otherwise obtains input queries from one or more of the electronic devices 106 and generates, executes or otherwise performs corresponding query statements on one or more of the different logical layers of the database 104 to obtain results provided to the respective electronic devices 106 in response to the respective input queries, as described in greater detail below in the context of FIGS. 2-5.

Still referring to FIG. 1, in exemplary embodiments, the historical observational data 120 maintained in the database 104 includes, in association with a particular patient (or patient identifier), historical measurement data indicative of the patient's physiological condition (e.g., historical blood glucose values, historical interstitial glucose values, and/or the like) with respect to time, historical delivery data indicative of dosages of fluid or medicament delivered to the patient (e.g., historical meal or correction boluses, basal dosages or other automated delivery amounts, and the like) with respect to time, historical meal data and/or other event log data associated with the patient, historical contextual data pertaining to the measurement data, the delivery data, the event log data, and the like. For example, the server 102 may receive, from a medical device via the network 108, measurement data values associated with a particular patient (e.g., sensor glucose measurements, acceleration measurements, and the like) that were obtained using a sensing element, and the server 102 stores or otherwise maintains the historical measurement data as patient data 120 in the database 104 in association with the patient (e.g., using one or more unique patient identifiers). Additionally, the server 102 may also receive, from or via a client device 106, meal data or other event log data that may be input or otherwise provided by the patient (e.g., via a client application at the client device 106) and store or otherwise maintain historical meal data and other historical event or activity data associated with the patient in the database 104. In this regard, the meal data include, for example, a time or timestamp associated with a particular meal event, a meal type or other information indicative of the content or nutritional characteristics of the meal, and an indication of the size associated with the meal. In exemplary embodiments, the server 102 also receives historical fluid delivery data (e.g., insulin delivery dosage amounts and corresponding timestamps) corresponding to basal or bolus dosages of fluid delivered to the patient by an infusion device 106. The server 102 may also receive geolocation data and potentially other contextual data associated with an electronic device 106 providing the patient data 120, and store or otherwise maintain the historical operational context data in association with the particular patient. In this regard, one or more of the devices 106 may include a global positioning system (GPS) receiver or similar modules, components or circuitry capable of outputting or otherwise providing data characterizing the geographic location of the respective device 106 in real-time.

The electronic medical records (EMR) data 122 generally includes, in association with one or more identifiers for a given patient within the EMR data set, information indicative of medical diagnoses or medical conditions the patient has been diagnosed with, drugs or medications that have been administered or taken by the patient, prescription information, therapy changes for the patient, laboratory results or measurements for physiological conditions of the patient, immunization records for the patient, microbiology results or other observations pertaining to the patient, healthcare utilization information (e.g., hospitalizations, emergency room visits, outpatient visits, etc.), demographic information associated with the patient (e.g., age, income, education, location, gender), past medical procedures, clinical observations or other habitual behavior information (e.g., smoking, alcohol usage, etc.), family medical history, physician notes and care plans, and/or the like. The EMR data 122 may also include data about the healthcare provider(s) associated with various aspects of a patient's medical records, the patient's insurance information, and/or the like. In various embodiments, the EMR data 122 could be received or obtained by the server 102 from another server computing device, another database different from database 104 (e.g., by replication from another database), individual computing devices associated with healthcare providers, patients, and/or the like. The claims data 124 generally includes, in association with one or more identifiers for a given patient within the claims data set, information pertaining to medical insurance claims submitted by or on behalf of the patient, including cost information, prescriptions filled or refilled by the patient, and the like. Similar to the EMR data 122, the claims data 124 could be received or obtained by the server 102 from another server computing device, another database different from database 104 (e.g., by replication from another database), individual computing devices associated with healthcare providers, patients, pharmacies, and/or the like. In exemplary embodiments, the claims data 124 includes medical, pharmaceutical, and confinement related claims data, including the respective diagnosis, procedure, prescription code(s), cost(s) (e.g., net plus allowed amount(s), etc.), and the like.

Figure 2:
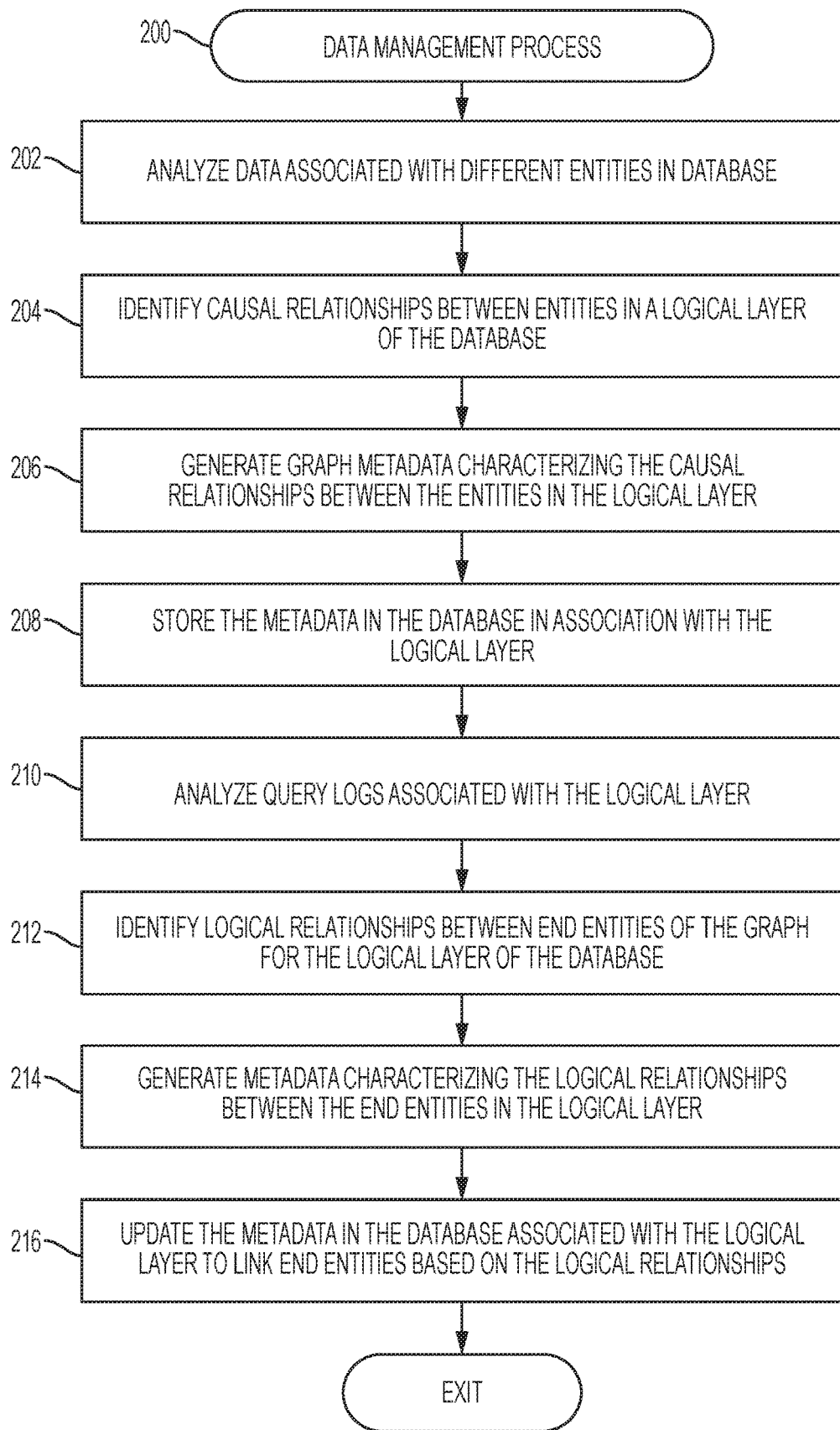
FIG. 2 is a flow diagram of an exemplary data management process suitable implementation in connection with the patient data management system of FIG. 1 in one or more exemplary embodiments.

FIG. 2 depicts an exemplary data management process 200 suitable for implementation by a computing device, such as the server 102 in the patient data management system 100 of FIG. 1. The various tasks performed in connection with the data management process 200 may be performed by hardware, firmware, software executed by processing circuitry, or any combination thereof. For illustrative purposes, the following description refers to elements mentioned above in connection with FIG. 1. In practice, portions of the data management process 200 may be performed by different elements of the patient data management system 100; however, for purposes of explanation, the data management process 200 may be described primarily in the context of implementation at or by the server 102 and/or the data management application 110. It should be appreciated that the data management process 200 may include any number of additional or alternative tasks, the tasks need not be performed in the illustrated order and/or the tasks may be performed concurrently, and/or the data management process 200 may be incorporated into a more comprehensive procedure or process having additional functionality not described in detail herein. Moreover, one or more of the tasks shown and described in the context of FIG. 2 could be omitted from a practical embodiment of the data management process 200 as long as the intended overall functionality remains intact.

In exemplary embodiments, the data management process 200 is performed, facilitated, or otherwise supported by the data management application 110 at the server 102 to generate graph metadata 126 for the different logical layers to be supported by the database 104. For example, in one embodiment where the database system 104 maintains data 120, 122, 124 pertaining to diabetic patients, the database 104 supports five different logical layers: a patient layer, a lifestyle layer, a therapy layer, a diabetes management layer, and a diabetes knowledge layer. The patient layer contains subsets of patient data 120 and EMR data 122 pertaining to individual patients including, but not limited to, historical patient glucose measurements, information characterizing historical glucose excursion events, and information characterizing complications or improvements to a respective patient's physiological condition. In this regard, the graph metadata 126 may indicate which fields of the patient data 120 and the EMR data 122 associated with an individual patient should be mapped to or otherwise utilized for nodes of the patient layer graph data structure along with the corresponding edges or links between those nodes. The patient layer can be queried to obtain information pertaining to the patient's health history, such as glucose measurements, excursion events, year-over-year improvements, comorbidities, complications, and/or the like. The lifestyle layer incorporates event log data and potentially other subsets of patient data 120 and EMR data 122 pertaining to respective individual patients. The therapy layer incorporates subsets of data 120, 122, 124 that indicate what drugs, medications, or other therapies are associated with a respective patient, and may include, for example, indication of what types of medical devices the patient may be using to manage or monitor his or her therapy (e.g., an infusion device, a continuous glucose monitoring device, or the like) along with costs associated with the patient's therapy. The diabetes management layer incorporates subsets of the data 120, 122, 124 that support maintaining relationships between different individuals or entities represented within the data sets 120, 122, 124 including patients, healthcare providers, physicians, payers, hospitals, and the like. The diabetes knowledge layer incorporates subsets of the data 120, 122, 124 that supports queries for general knowledge that is patient independent, such as, for example, queries pertaining to a particular physiological condition or diagnosis (e.g., Type 1 diabetes, Type 2 diabetes, or the like), pharmacodynamics of insulin or other fluids, drugs, or medications, excursion events, types of meals, and the like.

For each logical database layer, the illustrated data management process 200 periodically scans or otherwise analyzes the nodes or entities within the graph data structure associated with the respective logical database layer to identify causal relationships between entities within that logical database layer (tasks 202, 204). In one or more embodiment, the data management application 110 implements or otherwise performs machine learning-based causality analysis to discover repeated cause and effect pairings of nodes within the graph data structure. For example, timestamps or other temporal relationships between meal event entities and glucose excursion event entities associated with a particular patient or across multiple different patients may be utilized to identify a causal relationship between the meal event and glucose excursion event and establish a causal link between the meal event and glucose excursion event entities in the lifestyle layer. In response to discovering a relationship between previously unconnected nodes or entities within the graph data structure associated with the respective logical database layer, the data management process 200 creates or otherwise generates updated graph metadata characterizing the identified relationship between nodes and stores or otherwise maintains the updated graph metadata in the database in association with the logical database layer (tasks 206, 208). In this regard, the data management application 110 updates the graph metadata 126 associated with the particular logical database layer to create new directional edges or links between previously unconnected nodes or entities within that logical database layer that were identified as having a causal relationship.

As one example, the data management application 110 may detect a pattern where meals with more than a threshold amount of fat (e.g., more than 50 grams) result in a hyperglycemic excursion event having longer than a threshold duration (e.g., more than 45 minutes), and thereby establish a directional link or edge between one or more meal event nodes having more than the threshold amount of fat and the corresponding hyperglycemic excursion outcome node. The newly created edges may be assigned a weighting or other quantitative value that corresponds to or otherwise reflects the strength of the relationship between the nodes (e.g., based on a probabilistic analysis of the rate of occurrence of the outcome). As another example, it may be determined that for a particular group of patients having certain characteristics in common, exercising more than a threshold number of times per week (e.g., 3 or more times per week) results in an increase in insulin sensitivity, thereby establish a directional link or edge between certain exercise event nodes and an increased insulin sensitivity outcome node with a weighting corresponding to the relative probability of an increase in insulin sensitivity resulting from the respective exercise event.

Still referring to FIG. 2, in exemplary embodiments, the data management process 200 also analyzes query logs associated with the respective logical database layers to identify relationships between previously unconnected nodes or entities within that logical database layer based on the results of previously executed queries. In this regard, the database 104 may store or otherwise maintain a query log where in response to executing a query statement, a corresponding log entry is created that maintains an association between the logical database layer being queried and the query path resulting from execution of the query statement (e.g., the sequence of nodes and edges traversed within that logical database layer during execution of the query statement).

In exemplary embodiments, for each logical database layer, the illustrated data management process 200 periodically analyzes the query logs associated with that logical database layer to identify logical relationships between nodes or entities within that logical database layer based on repeated queries that traverse those nodes or entities (tasks 210, 212). For example, in one or more embodiment, the data management application 110 analyzes the query logs associated with a particular logical database layer to identify or retrieve query paths that traverse more than a threshold number of nodes or entities within the database layer (e.g., more than 3 nodes). Within that subset of query paths traversing more than the threshold number of nodes, the data management application 110 identifies repeated query paths having common end nodes and establishes logical relationships between those end nodes within the logical database layer. In this regard, the data management process 200 creates or otherwise generates updated graph metadata establishing a logical relationship between the previously unconnected end nodes and stores or otherwise maintains the updated graph metadata in the database in association with the logical database layer (tasks 214, 216). In this manner, the data management application 110 creates new edges or links between the end nodes of repeated query paths having common end nodes and traversing more than a threshold number of nodes.

By virtue of the data management process 200 creating or otherwise establishing relationships between previously unconnected nodes within the graph data structure for a particular logical database layer, subsequent queries of that logical database layer may be executed or performed more efficiently, or otherwise provide improved results that reflect likely causal and/or logical relationships between nodes of the graph data structure. In exemplary embodiments, the data management process 200 is performed for each different logical database layer, and the data management process 200 may repeat periodically (e.g., daily, weekly, monthly, or the like) to continually analyze and update the relationships between the nodes or entities within the respective logical database layers.

Figure 3:
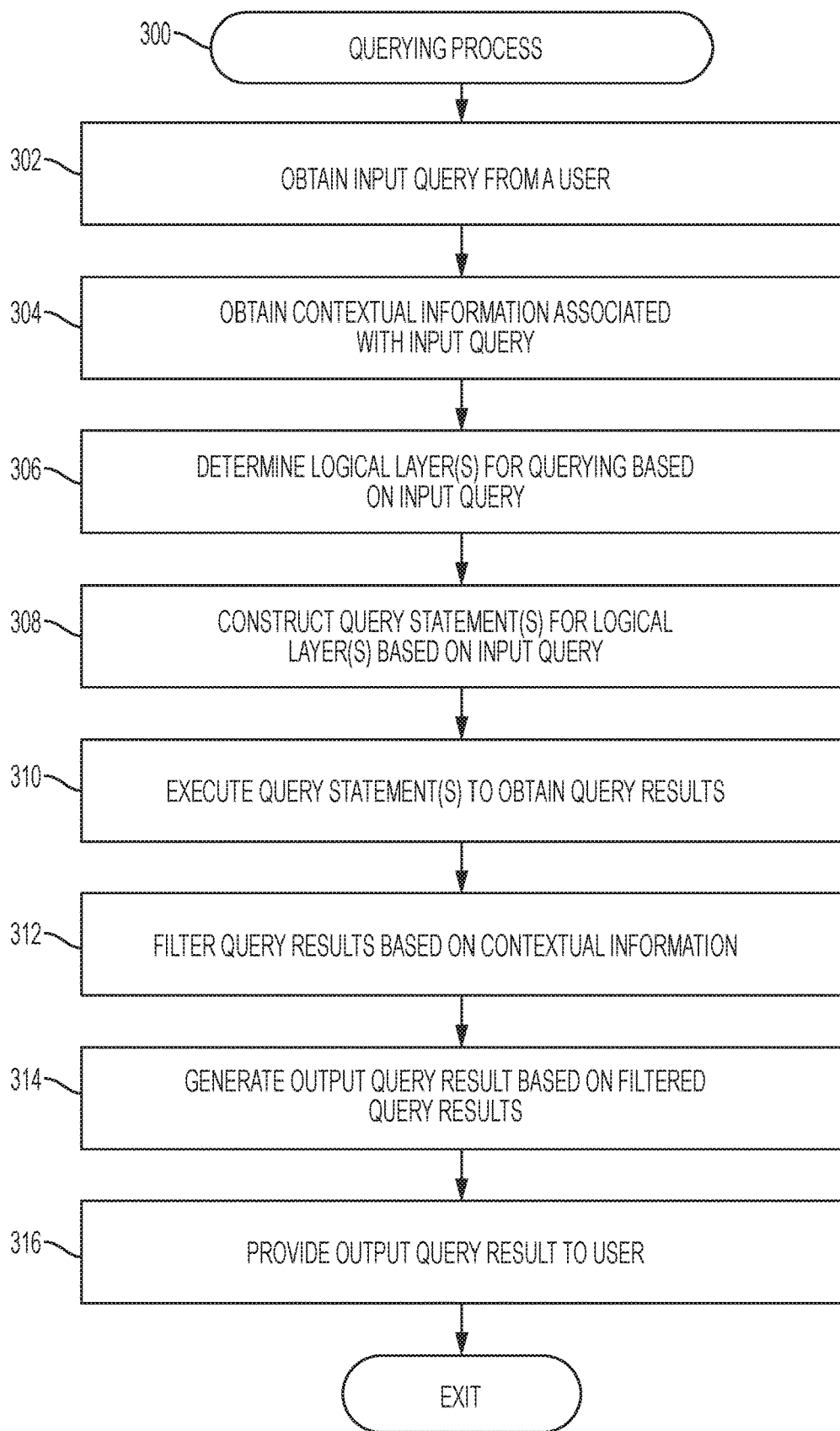
FIG. 3 is a flow diagram of an exemplary querying process suitable implementation in connection with the patient data management system of FIG. 1 in one or more exemplary embodiments.

FIG. 3 depicts an exemplary querying process 300 suitable for querying a database having a plurality of different logical layers, such as the database 104 in the patient data management system 100 of FIG. 1. For purposes of explanation, the querying process 300 may be described herein primarily in the context of input queries received from human users or patients in a conversational form; however, it should be appreciated that the querying process 300 is not limited to conversational input queries received from users, and the querying process 300 could be implemented in an equivalent manner for queries that are neither submitted or initiated by users nor provided in a conversational form. The various tasks performed in connection with the querying process 300 may be performed by hardware, firmware, software executed by processing circuitry, or any combination thereof. For illustrative purposes, the following description refers to elements mentioned above in connection with FIG. 1. In practice, portions of the querying process 300 may be performed by different elements of the patient data management system 100; however, for purposes of explanation, the querying process 300 may be described primarily in the context of implementation at or by the server 102 and/or the query management application 112. It should be appreciated that the querying process 300 may include any number of additional or alternative tasks, the tasks need not be performed in the illustrated order and/or the tasks may be performed concurrently, and/or the querying process 300 may be incorporated into a more comprehensive procedure or process having additional functionality not described in detail herein. Moreover, one or more of the tasks shown and described in the context of FIG. 3 could be omitted from a practical embodiment of the querying process 300 as long as the intended overall functionality remains intact.

In the illustrated embodiment, the querying process 300 receives or otherwise obtains an input query from a patient or other user (task 302). For example, a patient may interact with or otherwise manipulate a user interface associated with a client application on an electronic device 106 to create an input query, which is then transmitted or otherwise provided to the server 102 via the network 108. In one or more embodiments, the input query is realized as a conversational string of words or text provided to the server 102. In this regard, the input query may be created or otherwise provided by the user in a free-form or unstructured manner using natural language rather than a predefined syntax. For example, in one or more embodiments, the electronic device 106 includes an audio input device and a speech recognition engine or vocabulary that supports parsing or otherwise resolving a conversational speech or audio input by a user of the device 106 into a corresponding textual representation to be provided to the server 102. In various embodiments, the conversational input query may be received unprompted, or alternatively, the user may manipulate the device 106 to select or otherwise activate a graphical user interface (GUI) element that enables or initiates the querying process 300. For example, in one or more embodiments, the querying process 300 may be initiated in response to a user selecting a GUI element for a search feature, a digital assistant, or similar feature supported by a client application at the device 106. In response, the client application at the device 106 may generate or otherwise provide a GUI display or other GUI elements that prompts the user to indicate what he or she would like to know or inquire about. Thereafter, the user may input a conversational string of words (e.g., via voice, typing, swiping, touch, or any other suitable input method), with a textual representation of the conversational input query being provided by the device 106 to the server 102 over the network 108.

In exemplary embodiments, the querying process 300 also receives or otherwise obtains contextual information associated with the input query from the client electronic device providing the input query (task 304). The operational context information provided along with the input query characterizes the current operational state or environment at the time of the input query. For example, in association with a submitted input query, the client device 106 may also transmit or otherwise provide contextual information pertaining to the operations of the client device 106, such as, for example, the current location of the client device 106, the current local time and the current day of week at the location of the client device 106, the current environmental conditions at the location of the client device 106, and/or the like. Additionally, in some embodiments, the client device 106 may also provide information indicative of the current physiological condition of the user and/or the current operational status of an infusion device or other medical device associated with the user. For example, along with the input query, the client device 106 may transmit or otherwise provide one or more of a current or most recent glucose measurement associated with the user, indication of whether delivery of insulin by an infusion device associated with the user is suspended or not, the current or most recent insulin delivery to the user, the current or most recent heart rate measurement associated with the user, an acceleration measurement or other measurement of an activity level associated with the user, and/or the like.

The illustrated querying process 300 continues by identifying or otherwise determining which one or more logical database layers should be queried based at least in part on the input query and then generating or otherwise constructing one or more corresponding query statements to be executed on the identified logical database layers based at least in part on the input query (tasks 306, 308). In this regard, the query management application 112 at the server 102 may analyze the input query to identify or otherwise determine the probable intent or objective of the query, and then determine which logical database layers to be queried based on the intent or objective of the query. In some embodiments, the query management application 112 at the server 102 may also analyze the context information associated with the input query along with the content of the input query when determining which of logical database layers should be queried. Once the logical layers to be queried are identified, the query management application 112 at the server 102 analyzes the content of the input query to obtain parameters or criteria to be utilized for the querying and then generates or otherwise constructs query statements for execution on the identified logical database layers using those parameters or criteria. Additionally, in some embodiments, the query management application 112 at the server 102 may also utilize operational context information associated with the input query for one or more parameters or criteria when constructing the query statements.

After constructing query statements, the querying process 300 executes or otherwise initiates execution of the constructed query statements on the identified logical database layer(s) to obtain results for the input query from the identified logical database layer(s) (task 310). In this regard, when the constructed query statements are linked or otherwise depend on one another, the query management application 112 at the server 102 may initiate a first query statement on a first logical layer of the database 104 to obtain results to that intermediary query statement, which, in turn, are utilized by a second query statement performed on a different logical layer of the database 104. For example, results obtained from querying one logical database layer may be utilized as parameters or criteria in a subsequent query statement on a different logical database layer. Additionally, in some embodiments, the results obtained from querying one logical database layer may be filtered, processed, analyzed, or otherwise optimized to determine the parameters or criteria for use in a subsequent query statement on a different logical database layer, as described in greater detail below in the context of FIG. 4.

To execute a query statement, the database 104 utilizes the graph metadata 126 to traverse the nodes or entities within the queried logical database layer in accordance with the established edges or links between the nodes or entities within that logical database layer to obtain results for the query statement. It should be noted that by virtue of the weighted directed graph data structures utilized to maintain data in the database 104, the response time for executing query statements at the database 104 is typically less than traditional databases reliant on primary key and/or foreign key based table scanning by supporting point-based index referencing that does not require complex table scanning sequences. In exemplary embodiments, a query path detailing the nodes or entities and corresponding edges traversed during execution of the query statement is also stored or otherwise maintained in a query log at one of the server 102 or the database 104 in association with the queried logical database layer, as described above.

In one or more exemplary embodiments, the querying process 300 filters the initial query results based on the operational context information associated with the input query prior to generating an output query result responsive to the received input query based on the filtered query results (task 312). In this regard, the initial query results may be analyzed with respect to the current operational context associated with the input query to select or otherwise identify a subset of the initial query results that is most relevant to one or more aspects of the current operational context. The query management application 112 at the server 102 may select, from among the initial query results obtained by executing the query statements, a subset of information that is most likely to be relevant to the current location of the client device 106, the current local time of day at the location of the client device 106, the current day of the week, the current environmental conditions at the location of the client device 106, the current physiological condition of the patient, the current operational status of an infusion device or other medical device, and/or the like. For example, the query management application 112 may select one of the initial query results that is closest to or within a threshold distance of the current location of the client device 106. As another example, the query management application 112 may select one of the initial query results that is most likely to yield the best patient outcome based on the patient's current glucose level, the current operational status of the patient's infusion device (e.g., delivery suspended, reservoir depletion, or the like).

The querying process 300 generates or otherwise constructs a response to the input query based on the filtered query results and then presents or otherwise provides the query response in response to the input query (tasks 314, 316). For example, in one or more embodiments, the query management application 112 generates a conversational query response using the filtered query results and then transmits the conversational query response to the querying client device 106 for presentation or reproduction within the context of a conversation that includes the conversational input query.

Figure 4:
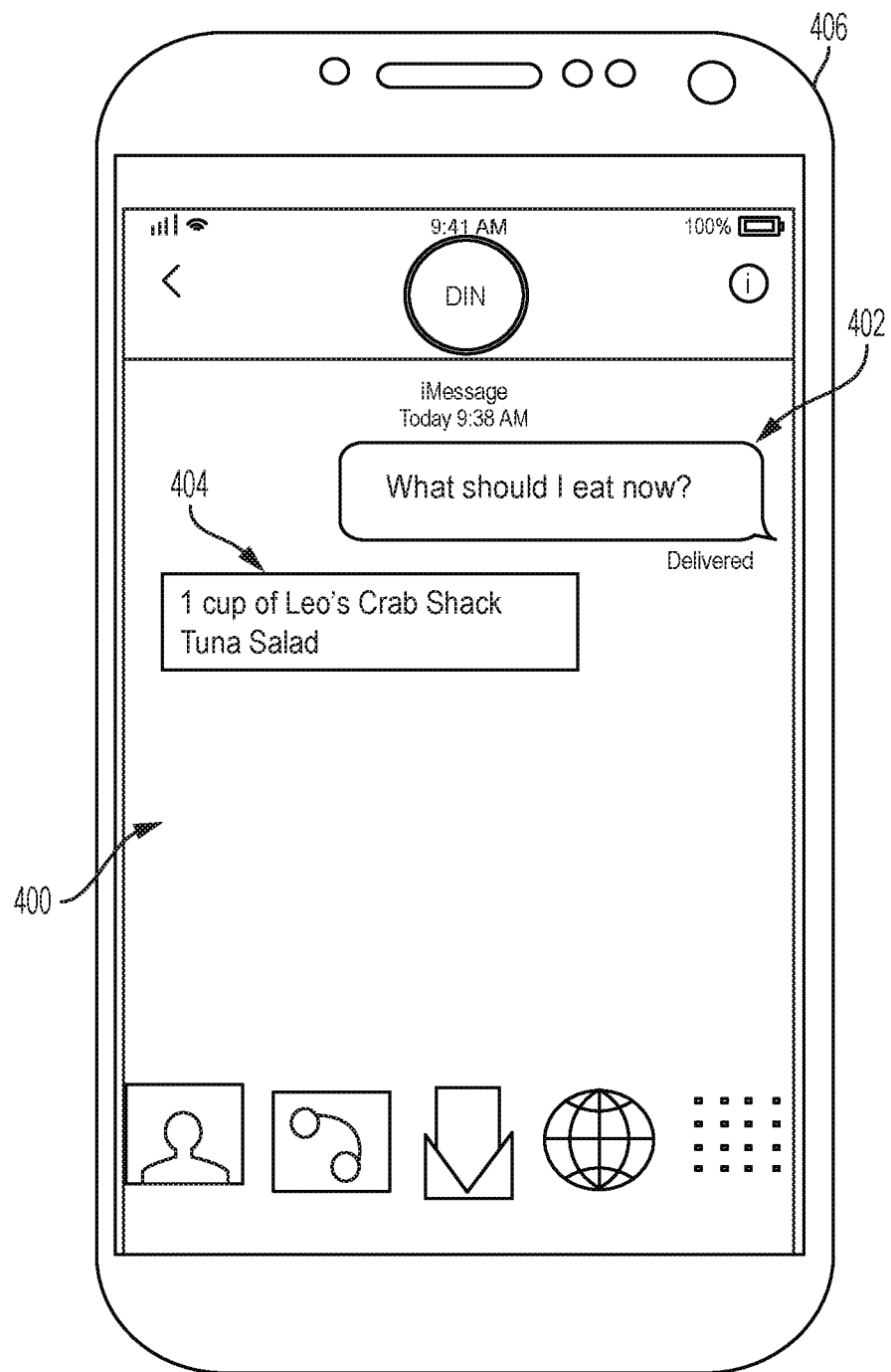
FIG. 4 depicts an exemplary graphical user interface (GUI) display suitable for presentation on a client electronic device in the patient data management system of FIG. 1 in accordance with an exemplary embodiment of the querying process of FIG. 3.

FIG. 4 depicts an exemplary embodiment of a graphical user interface (GUI) display 400 that may be presented at a querying client device 406 (e.g., one of devices 106) in the patient data management system 100 of FIG. 1 in connection with the querying process 300 of FIG. 3. The GUI display 400 includes a dialog box or one or more similar GUI elements that prompt a user to interact with the client device 106, 406 conversationally to query the database 104. In the illustrated embodiment, a patient using the querying client device 106, 406 utilizes an input device or user interface at the client device 106, 406 to input or otherwise provide a conversational input query. In response, an application at the client device 106, 406 updates the GUI display 400 to graphically depict a textual representation of the conversational input query 402 received by the client device 106, 406. The application at the client device 106, 406 transmits, submits, or otherwise provides the conversational input query text to the query management application 112 at the server 102 for execution.

As described above in the context of FIG. 3, the query management application 112 analyzes the conversational input query text "What should I eat now?" to determine the intent or objective of the input query (e.g., intent=find food), the subject of the input query (e.g., subject=patient identifier), and any other temporal or contextual parameters contained within or associated with the input query (e.g., time=now). Based on identifying the subject of the input query as the patient, the query management application 112 may determine that the lifestyle logical layer of the database 104 should be queried to obtain lifestyle information pertaining to the patient. In this regard, the query management application 112 may construct an initial query statement for querying the lifestyle logical layer of the database 104 using the patient's unique identifier to retrieve lifestyle information associated with the patient. For example, executing the query on the lifestyle logical layer of the database 104 may return information indicating the current or recent type of diet that the patient has been consuming (e.g., low carb), information pertaining to the patient's exercise habits or other recent activity by the patient, and/or potentially other contextual information characterizing the patient's lifestyle. Additionally, based on identifying the subject of the input query as the patient, the query management application 112 may also query the patient logical layer of the database 104 to identify other patient's similar to the patient that is the subject of the input query (e.g., based on the edges or links in the graph metadata 126 for the patient logical layer linking those other patients with the current patient via more than a threshold number of common nodes or entities).

Using the lifestyle information obtained from querying the lifestyle logical layer and the identifiers for other patient's similar to the subject patient, the query management application 112 generates or otherwise constructs a query statement for querying the patient logical layer to obtain meal logs or other meal information associated with a subset of the similar patients that have similar lifestyle information associated therewith (e.g., patients that have similar exercise or activity behavior, geographic location, and/or the like) and for which the outcome of the meals were good (e.g., no hypoglycemic or hyperglycemic events or other excursion events following the meals for having similar lifestyle contexts, postprandial glucose within a threshold amount of a patient's target glucose value, etc.). After obtaining information for the meals consumed by similar patients that had positive outcomes from the patient logical layer, the query management application 112 may generates or otherwise constructs a query statement for querying the lifestyle logical layer to identify a subset of those meals that best match or are most closely associated with the patient's lifestyle information (e.g., meals associated with low carb diets or other patient's having low carb diets associated therewith, and/or the like). In one or more exemplary embodiments, the query statement may also account for the current operational context for the patient (e.g., meals within a threshold distance of the current location of the client device 106, 406, and/or the like). In yet other embodiments, the current operational context is utilized to filter or otherwise exclude query results and identify a meal result that best matches the querying patient's current operational context and lifestyle.

After obtaining a meal result from the querying the lifestyle logical layer that best matches the patient's lifestyle and current operational context and achieved a positive outcome for one or more similar patients, the query management application 112 generates or otherwise constructs a query response that includes or incorporates that meal result in a conversational form. In this regard, in one or more embodiments, based on the identified meal type and the current location associated with the input query, the query management application 112 queries a database of restaurant information including geographic location information and menu data associated with a plurality of restaurants to identify a restaurant closest to or otherwise in the vicinity of the current location of the querying device 106, 406 that serves an item that matches or corresponds to the identified meal. The query management application 112 may then generate query response text that indicates the identified restaurant and menu item that best matches the meal result from querying the database 104. The query management application 112 transmits or otherwise provides the conversational query response text to the querying client device 106, 406 for presentation at the client device 106, 406. An application at the client device 106, 406 updates the GUI display 400 to graphically depict the textual representation of the conversational query response 404 received by the client device 106, 406 from the server 102 within the context of the conversation including the conversational input query 402.

Figure 5:
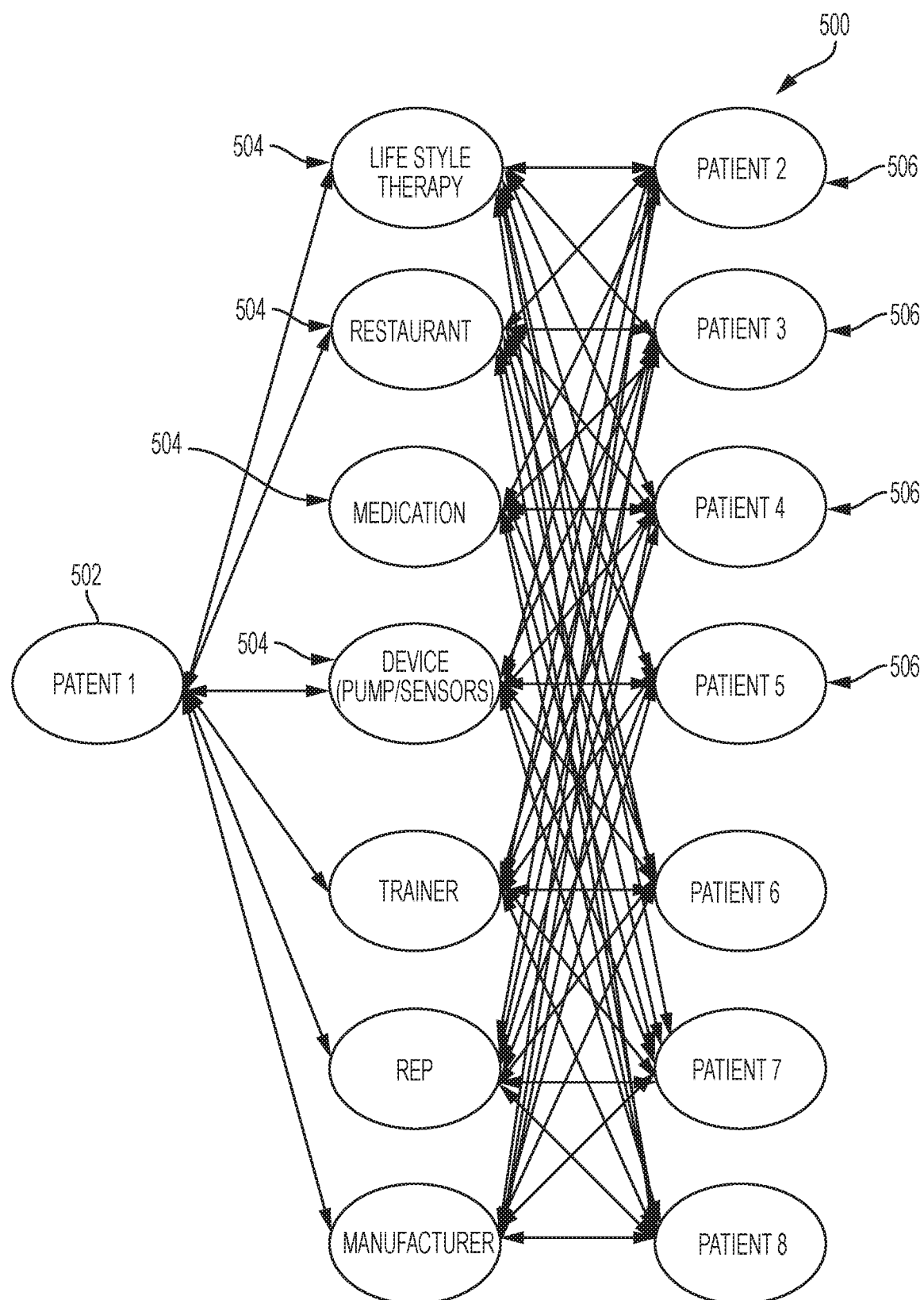
FIG. 5 depicts an exemplary graph data structure suitable for implementation at a logical database layer in the patient data management system of FIG. 1.

FIG. 5 depicts an exemplary graphical representation of a partial graph data structure 500 corresponding to a subset of a patient logical layer in the database 104 that depicts the relationships between different patients that may be related to a query subject patient based on the graph metadata 126. In this regard, FIG. 5 depicts a node 502 within the patient logical layer that is associated with a querying patient. Based on the graph metadata 126, the querying patient node 502 is associated with a plurality of different entity nodes 504 within the patient logical layer, with those entity nodes 504 corresponding to different fields or subsets of the data 120, 122, 124 in the database 104 that are associated with the querying patient and mapped to the various nodes based on the graph metadata 126 for the patient logical layer. Additionally, the graph metadata 126 for the patient logical layer may also define edges or links between the entity nodes 504 associated with the querying patient 502 to one or more other patient nodes 506 associated with different patients having similar values for their associated fields or subsets of the data 120, 122, 124 in the database 104 that map to those entity nodes 504. In some embodiments, the edges between an entity node 504 and a similar patient node 506 may be assigned a weight based on the difference or similarity between the value(s) of the querying patient's associated fields or subsets of the data 120, 122, 124 that map to that node 504 and the value(s) of those fields or subsets of the data 120, 122, 124 associated with the respective patient having his or her patient node 506 linked to the respective entity node 504. Thus, both the number of edges between respective pairs of related patient nodes 502, 506 and the respective weightings assigned to those edges may be utilized to calculate or otherwise determine a metric indicative of the relative similarity between the query subject associated with patient node 502 and a different patient associated with one of patient nodes 506.

As described above in the context of FIG. 4, the graph metadata 126 associated with the patient logical layer in the database 104 may be utilized when executing a query statement on the patient logical layer to obtain patient identifiers associated with patient nodes 506 that are most similar to the query subject (e.g., based on a similarity metric characterizing the relationship between respective pairs of patient nodes 502, 506). The patient identifiers associated with the similar patient nodes 506 may then be utilized to query other logical layers of the database 104 to obtain information indicative of meals, activities, medications, therapies, and/or the like by those patients and how such variables affected those patients' physiological conditions (e.g., glucose measurements, excursion events, and/or the like) to generate recommendations or otherwise provide query results that are most likely to achieve the best outcome in regards to the physiological condition of the query subject patient.

In some embodiments, the nodes 504 could reside in a different logical layer of the database 104 than the patient nodes 502, 506, with respective pairs of patient nodes 502, 506 having at least a threshold number of nodes 504 in common or shared within another logical layer being utilized to establish a relationship between the respective pair of patient nodes 502, 506 or otherwise classify the pair of patient nodes 502, 506 to a common group or cohort, as described in greater detail below.

Cognitive Pump

Figure 6:
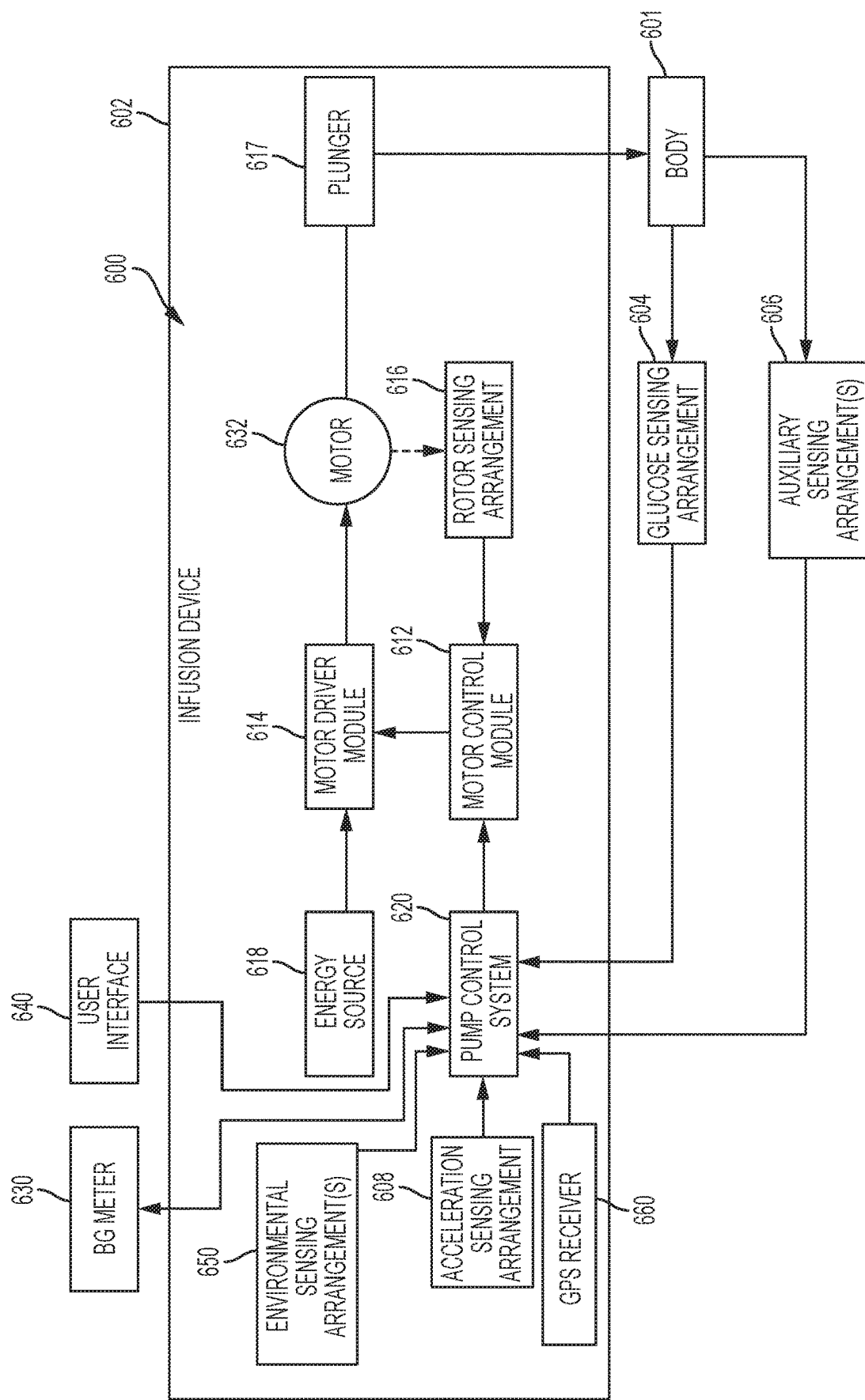
FIG. 6 is a block diagram of an exemplary infusion system suitable for use with a fluid infusion device in one or more embodiments.

Referring now to FIG. 6, in accordance with one or more exemplary embodiments, an infusion device 602 in an infusion system 600 is utilized as an electronic device 106 capable of querying the database 104 via the server 102 in the patient data management system 100 of FIG. 1. In this regard, the infusion device 602 is capable of receiving a conversational user input as well as capturing contemporaneous, concurrent, or otherwise temporally relevant operational context information associated with conversational user input and providing corresponding conversational input query text and associated context information to the query management application 112 at the server 102 in accordance with the querying process 300 of FIG. 3.

In exemplary embodiments, the infusion system 600 is also capable of controlling or otherwise regulating a physiological condition in the body 601 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 604 (e.g., sensing arrangement 604) communicatively coupled to the infusion device 602. However, it should be noted that in alternative embodiments, the condition being regulated by the infusion system 600 may be correlative to the measured values obtained by the sensing arrangement 604. That said, for clarity and purposes of explanation, the subject matter may be described herein in the context of the sensing arrangement 604 being realized as a glucose sensing arrangement that senses, detects, measures or otherwise quantifies the user's glucose level, which is being regulated in the body 601 of the user by the infusion system 600.

In exemplary embodiments, the sensing arrangement 604 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 601 of the user. The output electrical signals are filtered or otherwise processed to obtain a measurement value indicative of the user's interstitial fluid glucose level. In exemplary embodiments, a blood glucose meter 630, such as a finger stick device, is utilized to directly sense, detect, measure or otherwise quantify the blood glucose in the body 601 of the user. In this regard, the blood glucose meter 630 outputs or otherwise provides a measured blood glucose value that may be utilized as a reference measurement for calibrating the sensing arrangement 604 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 604 may alternatively be referred to herein as the sensor glucose value, the sensed glucose value, or variants thereof.

In exemplary embodiments, the infusion system 600 also includes one or more additional sensing arrangements 606, 608 configured to sense, detect, measure or otherwise quantify a characteristic of the body 601 of the user that is indicative of a condition in the body 601 of the user. In this regard, in addition to the glucose sensing arrangement 604, one or more auxiliary sensing arrangements 606 may be worn, carried, or otherwise associated with the body 601 of the user to measure characteristics or conditions of the user (or the user's activity) that may influence the user's glucose levels or insulin sensitivity. For example, a heart rate sensing arrangement 606 could be worn on or otherwise associated with the user's body 601 to sense, detect, measure or otherwise quantify the user's heart rate, which, in turn, may be indicative of exercise (and the intensity thereof) that is likely to influence the user's glucose levels or insulin response in the body 601. In yet another embodiment, another invasive, interstitial, or subcutaneous sensing arrangement 606 may be inserted into the body 601 of the user to obtain measurements of another physiological condition that may be indicative of exercise (and the intensity thereof), such as, for example, a lactate sensor, a ketone sensor, or the like. Depending on the embodiment, the auxiliary sensing arrangement(s) 606 could be realized as a standalone component worn by the user, or alternatively, the auxiliary sensing arrangement(s) 606 may be integrated with the infusion device 602 or the glucose sensing arrangement 604.

The illustrated infusion system 600 also includes an acceleration sensing arrangement 608 (or accelerometer) that may be worn on or otherwise associated with the user's body 601 to sense, detect, measure or otherwise quantify an acceleration of the user's body 601, which, in turn, may be indicative of exercise or some other condition in the body 601 that is likely to influence the user's insulin response.

While the acceleration sensing arrangement 608 is depicted as being integrated into the infusion device 602 in FIG. 6, in alternative embodiments, the acceleration sensing arrangement 608 may be integrated with another sensing arrangement 604, 606 on the body 601 of the user, or the acceleration sensing arrangement 608 may be realized as a separate standalone component that is worn by the user.

In exemplary embodiments, the infusion device 602 also includes one or more environmental sensing arrangements 650 to sense, detect, measure or otherwise quantify the current operating environment around the infusion device 602. In this regard, the environmental sensing arrangements 650 may include one or more of a temperature sensing arrangement (or thermometer), a humidity sensing arrangement, a pressure sensing arrangement (or barometer), and/or the like. In exemplary embodiments, the infusion device 602 also includes a position sensing arrangement 660 to sense, detect, measure or otherwise quantify the current geographic location of the infusion device 602, such as, for example, a global positioning system (GPS) receiver.

In the illustrated embodiment, the pump control system 620 generally represents the electronics and other components of the infusion device 602 that control operation of the fluid infusion device 602 according to a desired infusion delivery program in a manner that is influenced by the sensed glucose value indicating the current glucose level in the body 601 of the user. For example, to support a closed-loop operating mode, the pump control system 620 maintains, receives, or otherwise obtains a target or commanded glucose value, and automatically generates or otherwise determines dosage commands for operating an actuation arrangement, such as a motor 632, to displace the plunger 617 and deliver insulin to the body 601 of the user based on the difference between the sensed glucose value and the target glucose value. In other operating modes, the pump control system 620 may generate or otherwise determine dosage commands configured to maintain the sensed glucose value below an upper glucose limit, above a lower glucose limit, or otherwise within a desired range of glucose values. In practice, the infusion device 602 may store or otherwise maintain the target value, upper and/or lower glucose limit(s), insulin delivery limit(s), and/or other glucose threshold value(s) in a data storage element accessible to the pump control system 620.

Still referring to FIG. 6, the target glucose value and other threshold glucose values utilized by the pump control system 620 may be received from an external component or be input by a user via a user interface element 640 associated with the infusion device 602. In practice, the one or more user interface element(s) 640 associated with the infusion device 602 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 640 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 6 depicts the user interface element(s) 640 as being separate from the infusion device 602, in practice, one or more of the user interface element(s) 640 may be integrated with the infusion device 602. Furthermore, in some embodiments, one or more user interface element(s) 640 are integrated with the sensing arrangement 604 in addition to and/or in alternative to the user interface element(s) 640 integrated with the infusion device 602. The user interface element(s) 640 may be manipulated by the user to operate the infusion device 602 to deliver correction boluses, adjust target and/or threshold values, modify the delivery control scheme or operating mode, and the like, as desired.

Still referring to FIG. 6, in the illustrated embodiment, the infusion device 602 includes a motor control module 612 coupled to a motor 632 that is operable to displace a plunger 617 in a reservoir and provide a desired amount of fluid to the body 601 of a user. In this regard, displacement of the plunger 617 results in the delivery of a fluid, such as insulin, that is capable of influencing the user's physiological condition to the body 601 of the user via a fluid delivery path (e.g., via tubing of an infusion set). A motor driver module 614 is coupled between an energy source 618 and the motor 632. The motor control module 612 is coupled to the motor driver module 614, and the motor control module 612 generates or otherwise provides command signals that operate the motor driver module 614 to provide current (or power) from the energy source 618 to the motor 632 to displace the plunger 617 in response to receiving, from a pump control system 620, a dosage command indicative of the desired amount of fluid to be delivered.

In exemplary embodiments, the energy source 618 is realized as a battery housed within the infusion device 602 that provides direct current (DC) power. In this regard, the motor driver module 614 generally represents the combination of circuitry, hardware and/or other electrical components configured to convert or otherwise transfer DC power provided by the energy source 618 into alternating electrical signals applied to respective phases of the stator windings of the motor 632 that result in current flowing through the stator windings that generates a stator magnetic field and causes the rotor of the motor 632 to rotate. The motor control module 612 is configured to receive or otherwise obtain a commanded dosage from the pump control system 620, convert the commanded dosage to a commanded translational displacement of the plunger 617, and command, signal, or otherwise operate the motor driver module 614 to cause the rotor of the motor 632 to rotate by an amount that produces the commanded translational displacement of the plunger 617. For example, the motor control module 612 may determine an amount of rotation of the rotor required to produce translational displacement of the plunger 617 that achieves the commanded dosage received from the pump control system 620. Based on the current rotational position (or orientation) of the rotor with respect to the stator that is indicated by the output of the rotor sensing arrangement 616, the motor control module 612 determines the appropriate sequence of alternating electrical signals to be applied to the respective phases of the stator windings that should rotate the rotor by the determined amount of rotation from its current position (or orientation). In embodiments where the motor 632 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 612 operates the motor driver module 614 to apply the determined alternating electrical signals (e.g., the command signals) to the stator windings of the motor 632 to achieve the desired delivery of fluid to the user.

When the motor control module 612 is operating the motor driver module 614, current flows from the energy source 618 through the stator windings of the motor 632 to produce a stator magnetic field that interacts with the rotor magnetic field. In some embodiments, after the motor control module 612 operates the motor driver module 614 and/or motor 632 to achieve the commanded dosage, the motor control module 612 ceases operating the motor driver module 614 and/or motor 632 until a subsequent dosage command is received. In this regard, the motor driver module 614 and the motor 632 enter an idle state during which the motor driver module 614 effectively disconnects or isolates the stator windings of the motor 632 from the energy source 618. In other words, current does not flow from the energy source 618 through the stator windings of the motor 632 when the motor 632 is idle, and thus, the motor 632 does not consume power from the energy source 618 in the idle state, thereby improving efficiency.

Depending on the embodiment, the motor control module 612 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 612 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 612. The computer-executable programming instructions, when read and executed by the motor control module 612, cause the motor control module 612 to perform or otherwise support the tasks, operations, functions, and processes described herein.

It should be appreciated that FIG. 6 is a simplified representation of the infusion device 602 for purposes of explanation and is not intended to limit the subject matter described herein in any way. In this regard, depending on the embodiment, some features and/or functionality of the sensing arrangement 604 may implemented by or otherwise integrated into the pump control system 620, or vice versa. Similarly, in practice, the features and/or functionality of the motor control module 612 may implemented by or otherwise integrated into the pump control system 620, or vice versa. Furthermore, the features and/or functionality of the pump control system 620 may be implemented by control electronics located in the fluid infusion device 602, while in alternative embodiments, the pump control system 620 may be implemented by a remote computing device that is physically distinct and/or separate from the infusion device 602 (e.g., a mobile computing device communicatively coupled to the infusion device 602 over a personal area network or the like).

Figure 7:
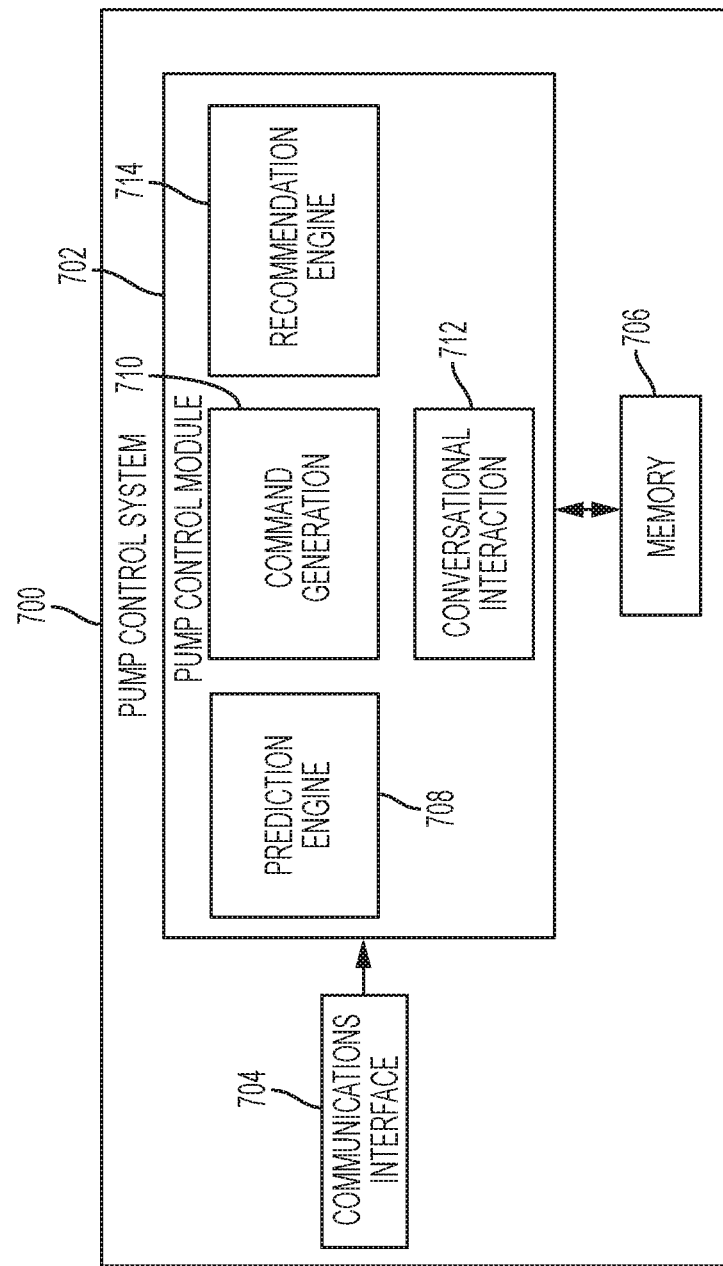
FIG. 7 is a block diagram of an exemplary pump control system suitable for use in the infusion device in the infusion system of FIG. 6 in one or more embodiments.

FIG. 7 depicts an exemplary embodiment of a pump control system 700 suitable for use as the pump control system 620 in FIG. 6 in accordance with one or more embodiments. The illustrated pump control system 700 includes, without limitation, a pump control module 702, a communications interface 704, and a data storage element (or memory) 706. The pump control module 702 is coupled to the communications interface 704 and the memory 706, and the pump control module 702 is suitably configured to support the operations, tasks, and/or processes described herein. In various embodiments, the pump control module 702 is also coupled to one or more user interface elements (e.g., user interface 640) for receiving user inputs (e.g., target glucose values or other glucose thresholds) and providing notifications, alerts, or other therapy information to the user.

The communications interface 704 generally represents the hardware, circuitry, logic, firmware and/or other components of the pump control system 700 that are coupled to the pump control module 702 and configured to support communications between the pump control system 700 and one or more of the various sensing arrangements 604, 606, 608, 650, 660. In this regard, the communications interface 704 may include or otherwise be coupled to one or more transceiver modules capable of supporting wireless communications between the pump control system 620, 700 and an external sensing arrangement 604, 606. For example, the communications interface 704 may be utilized to wirelessly receive sensor measurement values or other measurement data from each external sensing arrangement 604, 606 in an infusion system 600. In other embodiments, the communications interface 704 may be configured to support wired communications to/from the external sensing arrangement(s) 604, 606. In various embodiments, the communications interface 704 may also support communications with a remote server (e.g., server 102) or another electronic device in an infusion system (e.g., to upload sensor measurement values, receive control information, and the like).

The pump control module 702 generally represents the hardware, circuitry, logic, firmware and/or other component of the pump control system 700 that is coupled to the communications interface 704 and the sensing arrangements 604, 606, 608, 650, 660 and configured to determine dosage commands for operating the motor 632 to deliver fluid to the body 601 based on measurement data received from the sensing arrangements 604, 606, 608, 650, 660 and perform various additional tasks, operations, functions and/or operations described herein. For example, in exemplary embodiments, pump control module 702 implements or otherwise executes a command generation application 710 that supports one or more autonomous operating modes and calculates or otherwise determines dosage commands for operating the motor 632 of the infusion device 602 in an autonomous operating mode based at least in part on a current measurement value for a condition in the body 601 of the user. For example, in a closed-loop operating mode, the command generation application 710 may determine a dosage command for operating the motor 632 to deliver insulin to the body 601 of the user based at least in part on the current glucose measurement value most recently received from the sensing arrangement 604 to regulate the user's blood glucose level to a target reference glucose value. In various embodiments, the dosage commands may also be adjusted or otherwise influenced by contextual measurement data, that is, measurement data that characterizes, quantifies, or otherwise indicates the contemporaneous or concurrent operating context for the dosage command(s), such as, for example, environmental measurement data obtained from an environmental sensing arrangement 650, the current location information obtained from a GPS receiver 660 and/or other contextual information characterizing the current operating environment for the infusion device 602. Additionally, the command generation application 710 may generate dosage commands for boluses that are manually-initiated or otherwise instructed by a user via a user interface element.

In one or more exemplary embodiments, the pump control module 702 also implements or otherwise executes a prediction application 708 (or prediction engine) that is configured to estimate or otherwise predict the future physiological condition and potentially other future activities, events, operating contexts, and/or the like in a personalized, patient-specific (or patient-specific) manner. In this regard, in some embodiments, the prediction engine 708 cooperatively configured to interact with the command generation application 710 to support adjusting dosage commands or control information dictating the manner in which dosage commands are generated in a predictive or prospective manner. In this regard, in some embodiments, based on correlations between current or recent measurement data and the current operational context relative to historical data associated with the patient, the prediction engine 708 may forecast or otherwise predict future glucose levels of the patient at different times in the future, and correspondingly adjust or otherwise modify values for one or more parameters utilized by the command generation application 710 when determining dosage commands in a manner that accounts for the predicted glucose level, for example, by modifying a parameter value at a register or location in memory 706 referenced by the command generation application 710. In various embodiments, the prediction engine 708 may predict meals or other events or activities that are likely to be engaged in by the patient and output or otherwise provide an indication of how the patient's predicted glucose level is likely to be influenced by the predicted events, which, in turn, may then be reviewed or considered by the patient to prospectively adjust his or her behavior and/or utilized to adjust the manner in which dosage commands are generated to regulate glucose in a manner that accounts for the patient's behavior in a personalized manner.

In one or more exemplary embodiments, the pump control module 702 also implements or otherwise executes a conversational interaction application 712 that is configured to support conversational interactions with a patient or other user. For example, the conversational interaction application 712 may generate or otherwise provide a GUI display on a display device 640 associated with an infusion device 602 that includes a dialog box that prompts a user to conversationally interact with the infusion device 602. In this regard, in one or more embodiments, the conversational interaction application 712 may generate a GUI display that prompts a user to conversationally query or search a database system 104, such as GUI display 400. The conversational interaction application 712 may also support conversationally monitoring or managing a patient's physiological condition, as described above in the context of FIGS. 3-4 and in greater detail below in the context of FIGS. 13-16. In one or more exemplary embodiments, the pump control module 702 also implements or otherwise executes a recommendation application 714 (or recommendation engine) that is configured to support providing therapy recommendations to the patient, as described in greater detail below in the context of FIGS. 17-19.

Still referring to FIG. 7, depending on the embodiment, the pump control module 702 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 702, or in any practical combination thereof. In exemplary embodiments, the pump control module 702 includes or otherwise accesses the data storage element or memory 706, which may be realized using any sort of non-transitory computer-readable medium capable of storing programming instructions for execution by the pump control module 702. The computer-executable programming instructions, when read and executed by the pump control module 702, cause the pump control module 702 to implement or otherwise generate the applications 708, 710, 712, 714 and perform tasks, operations, functions, and processes described herein.

It should be understood that FIG. 7 is a simplified representation of a pump control system 700 for purposes of explanation and is not intended to limit the subject matter described herein in any way. For example, in some embodiments, the features and/or functionality of the motor control module 612 may be implemented by or otherwise integrated into the pump control system 700 and/or the pump control module 702, for example, by the command generation application 710 converting the dosage command into a corresponding motor command, in which case, the separate motor control module 612 may be absent from an embodiment of the infusion device 602.

Glucose Predictions and Forecasting

In one or more exemplary embodiments, a patient-specific forecasting model for a physiological condition is determined based on historical data associated with a patient and utilized to predict future values or levels of the physiological condition based at least in part on the current operational context and current measurements for the physiological condition. Additionally, historical event data and associated context information may be utilized to predict one or more future events at different times in the future within the forecast horizon based at least in part on the current measurement data, and/or the current operational context (e.g., the current time of day, the current day of the week, the current geographic location, and the like), which, in turn may be input to the patient-specific forecasting model to adjust the forecasted values or levels of the physiological condition at appropriate times in the future to reflect the predicted events. While the subject matter is described herein in the context of glucose forecasting and predictions, the subject matter is not necessarily limited to glucose levels and could be implemented in an equivalent manner to forecast or predict other physiological conditions of an individual.

In exemplary embodiments, a patient-specific glucose forecasting model is determined that allows for the patient's glucose level to be forecasted for discrete time intervals in the future. For purposes of explanation, the subject matter is described herein in the context of hourly forecasting that allows for the patient's glucose level to be forecast on an hourly basis; however, it should be noted that the subject matter described herein is not limited to hourly forecasting and could be utilized for different forecast time intervals (e.g., on an every 15-minute basis, a 30-minute basis, every 4 hours, and/or the like).

Figure 8:
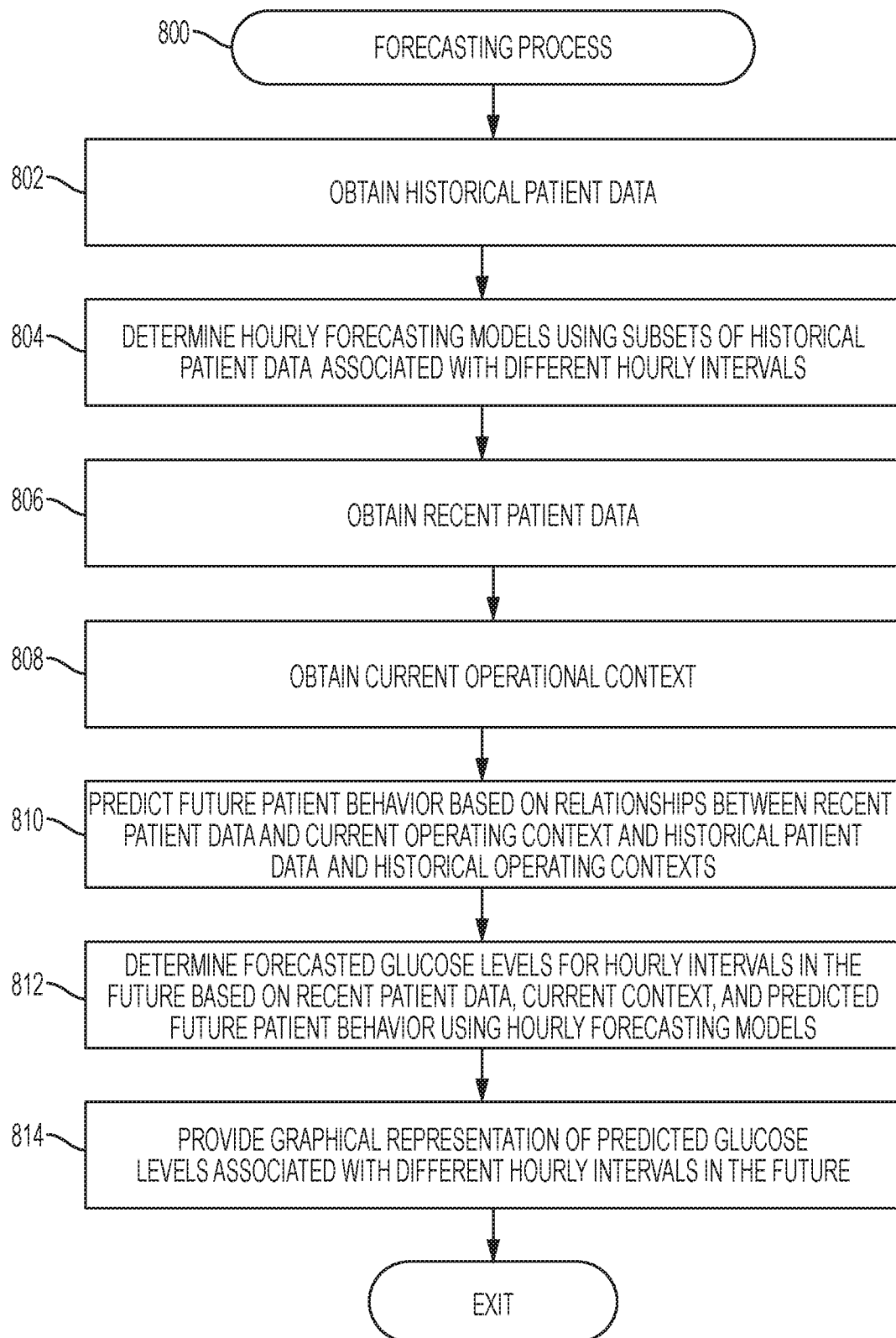
FIG. 8 is a flow diagram of an exemplary forecasting process suitable implementation in connection with a patient data management system in one or more exemplary embodiments.

FIG. 8 depicts an exemplary forecasting process 800 suitable for implementation by a computing device, such as a server 102 or client electronic device 106 in the patient data management system 100 of FIG. 1. The various tasks performed in connection with the forecasting process 800 may be performed by hardware, firmware, software executed by processing circuitry, or any combination thereof. For illustrative purposes, the following description refers to elements mentioned above in connection with FIGS. 1 and 6-7. In practice, portions of the forecasting process 800 may be performed by different elements of a patient data management system 100 or an infusion system 600, such as, for example, the server 102, the electronic device(s) 106, an infusion device 602, and/or the pump control system 620, 700. It should be appreciated that the forecasting process 800 may include any number of additional or alternative tasks, the tasks need not be performed in the illustrated order and/or the tasks may be performed concurrently, and/or the forecasting process 800 may be incorporated into a more comprehensive procedure or process having additional functionality not described in detail herein. Moreover, one or more of the tasks shown and described in the context of FIG. 8 could be omitted from a practical embodiment of the forecasting process 800 as long as the intended overall functionality remains intact.

The illustrated embodiment of the forecasting process 800 initializes or otherwise begins by retrieving or otherwise obtaining historical data associated with the patient of interest to be modeled and developing, training, or otherwise determining a forecasting model for the patient using the historical data associated with the patient (tasks 802, 804). In one or more exemplary embodiments, for an individual patient within the patient data management system 100, the server 102 periodically retrieves or otherwise obtains the historical patient data 120 associated with that patient from the database 104 and analyzes the relationships between different subsets of the historical patient data 120 to create a patient-specific forecasting model associated with that patient. Depending on the embodiment, the patient-specific forecasting model may be stored on the database 104 in association with the patient and utilized by the server 102 to determine a glucose forecast for the patient (e.g., in response to a request from a client device 106) and provide the resulting glucose forecast to a client device 106 for presentation to a user. In other embodiments, the server 102 pushes, provides, or otherwise transmits the patient-specific forecasting model to one or more electronic devices 106 associated with the patient (e.g., infusion device 602) for implementing and supporting glucose forecasts at the end user device (e.g., by prediction engine 708).

In one or more exemplary embodiments, a recurrent neural network is utilized to create hourly neural network cells that are trained to predict an average glucose level for the patient associated with that respective hourly interval based on subsets of historical patient data corresponding to that hourly interval across a plurality of different days preceding development of the model. For example, in one embodiment, for each hourly interval within a day, a corresponding long short-term memory (LSTM) unit (or cell) is created, with the LSTM unit outputting an average glucose value for that hourly interval as a function of the subset of historical patient data corresponding to that hourly interval and the variables from one or more of the LSTM units preceding the current LSTM unit. For example, a LSTM unit associated with the 1-2 PM time interval is configured to calculate an average glucose value for the patient over the 1-2 PM timeframe based on the subset of historical patient data timestamped within or otherwise associated with the 1-2 PM timeframe and the inputs to and/or outputs from one or more preceding LSTM units (e.g., the average glucose value for the patient over the 12-1 PM timeframe output by the 12-1 PM LSTM unit, a correlative portion of the subset of historical patient data timestamped within or otherwise associated with the 12-1 PM timeframe, and/or the like).

For each LSTM unit, machine learning may be utilized to determine a corresponding equation, function, or model for calculating the average glucose value for the patient for that time interval based at least in part on the historical insulin delivery data, historical meal data, and historical exercise data for the patient during that time interval. In this regard, the model for a particular hourly interval is capable of characterizing or mapping the insulin delivery data during the hourly interval, the meal data during the hourly interval, the exercise data during the hourly interval, and the average glucose value for the preceding hourly interval to the average sensor glucose value for the hourly interval being modeled. Additionally, the hourly model may account for historical auxiliary measurement data (e.g., historical acceleration measurement data, historical heart rate measurement data, and/or the like), historical medication data or other historical event log data, historical geolocation data, historical environmental data, and/or other historical or contextual data may be correlative to or predictive of the average glucose level for the patient during that time interval. Thus, as different variables have a greater or lesser impact on the patient's glucose level during the course of the day, the individual functions or equations associated with the respective LSTM units may increase or decrease the weighting or emphasis a particular input variable has on the average glucose value calculated by a respective LSTM unit as appropriate. It should be noted that any number of different machine learning techniques may be utilized to determine what input variables are predictive for a current patient of interest and a current hourly interval of the day, such as, for example, artificial neural networks, genetic programming, support vector machines, Bayesian networks, probabilistic machine learning models, or other Bayesian techniques, fuzzy logic, heuristically derived combinations, or the like.

The forecasting process 800 continues by receiving, retrieving, or otherwise obtaining recent patient data, identifying or otherwise obtaining the current operational context associated with the patient, and predicting future behavior of the patient based on the recent patient data and the current operational context (tasks 806, 808, 810). In this regard, predictive models for future insulin deliveries, future meals, future exercise events, and/or future medication dosages may be determined that characterize or map a particular combination of one or more of the current (or recent) sensor glucose measurement data, auxiliary measurement data, delivery data, geographic location, meal data, exercise data, patient behavior or activities, and the like to a value representative of the current probability or likelihood of a particular event or activity and/or a current value associated with that event or activity (e.g., a predicted meal size, a predicted exercise duration and/or intensity, a predicted bolus amount, and/or the like). Thus, the forecasting process 800 may obtain from one or more of the sensing arrangements 604, 606, 608 the infusion device 602 and/or the database 104 the current or most recent sensor glucose measurement values associated with the patient, along with data or information quantifying or characterizing recent insulin deliveries, meals, exercise, and potentially other events, activities or behaviors by the user within a preceding interval of time (e.g., within the preceding 2 hours). The forecasting process 800 may also obtain from one or more of the sensing arrangements 650, 660, the infusion device 602 and/or the database 104 data or information quantifying or characterizing the current or recent operational contexts associated with the infusion device 602.

Based on the current and recent patient measurement data, insulin delivery data, meal data, and exercise data, along with the current time of day, the current day of the week, and/or other current or recent context data, the forecasting process 800 determines event probabilities and/or characteristics for future hourly time intervals. For example, for each hourly time interval in the future, the forecasting process 800 may determine a meal probability and/or a predicted meal size during that future hourly time interval that may be utilized as an input to the LSTM unit for that hourly time interval. Similarly, the forecasting process 800 may determine a predicted insulin delivery amount, a predicted exercise probability and/or a predicted exercise intensity or duration, a predicted medication dosage, and/or the like during each respective future hourly time interval based on the relationships between the recent patient data and context data and historical patient data and context data preceding occurrence of previous instances of those events. Some examples of predicting patient behaviors or activities are described in U.S. patent application Ser. No. 15/847,750, which is incorporated by reference herein.

Still referring to FIG. 8, after predicting future patient behavior likely to influence the patient's future glucose levels, the forecasting process 800 continues by calculating or otherwise determining forecasted glucose levels for hourly intervals in the future based at least in part on the current or recent glucose measurement data and the predicted future behavior and generating or otherwise providing graphical representations of the forecasted glucose levels associated with the different future hourly intervals (tasks 812, 814). Based on the current time of day, the forecasting model for the next hourly interval of the day may be selected and utilized to calculate a forecasted glucose level for that hourly interval based at least in part on the recent sensor glucose measurement value(s) and the predicted meals, exercise, insulin deliveries and/or medication dosages for the next hourly interval of the day. For example, the current sensor glucose measurement value and preceding sensor glucose measurement values obtained within the current hourly interval may be averaged or otherwise combined to obtain an average sensor glucose measurement value for the current hourly interval that may be input to the forecasting model for the next hourly interval of the day. The forecasting model is then utilized to calculate a forecasted average glucose value for the next hourly interval of the day based on that average sensor glucose measurement value for the current hourly interval and the predicted patient behavior during the next hourly interval. The forecasted average glucose value for the next hourly interval may then be input to the forecasting model for the subsequent hourly interval for calculating a forecasted glucose value for that subsequent hourly interval based on its associated predicted patient behavior, and so on.

Figure 9:
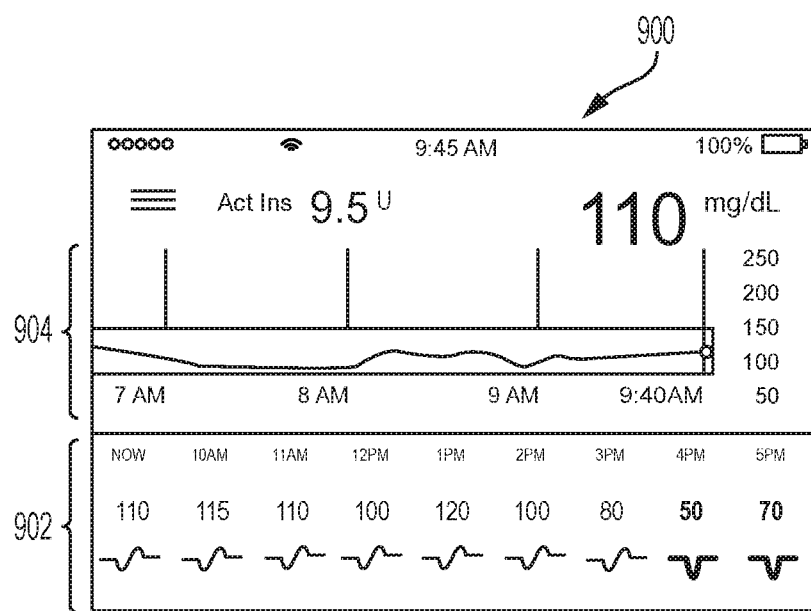
FIG. 9 depicts an exemplary GUI display suitable for presentation on a client electronic device in accordance with an exemplary embodiment of the forecasting process of FIG. 8.

FIG. 9 depicts an exemplary GUI display 900 including a glucose forecast region 902 that includes graphical representations of forecasted glucose levels for a patient in association with subsequent hourly intervals of the day. In the illustrated GUI display 900, a graphical representation 904 of the patient's recent sensor glucose measurement data is presented adjacent to the glucose forecast region 902. In exemplary embodiments, the sensor glucose measurement display region 904 includes a line chart or line graph of the patient's historical sensor glucose measurement data with a visually distinguishable overlay region that indicates a target range for the patient's sensor glucose measurement values. Depending on the embodiment, the GUI display 900 may be presented on a display device 640 associated with an infusion device 602 or on another electronic device 102, 106 within a patient data management system 100. In one or more embodiments, the forecasting process 800 is performed to generate the forecast region 902 on the GUI display 900 in response to a patient selecting a GUI element configured to cause presentation of the forecast region 902 or otherwise requesting presentation of a glucose forecast (e.g., by conversationally requesting a glucose forecast via conversational interaction application 712).

Figure 10:
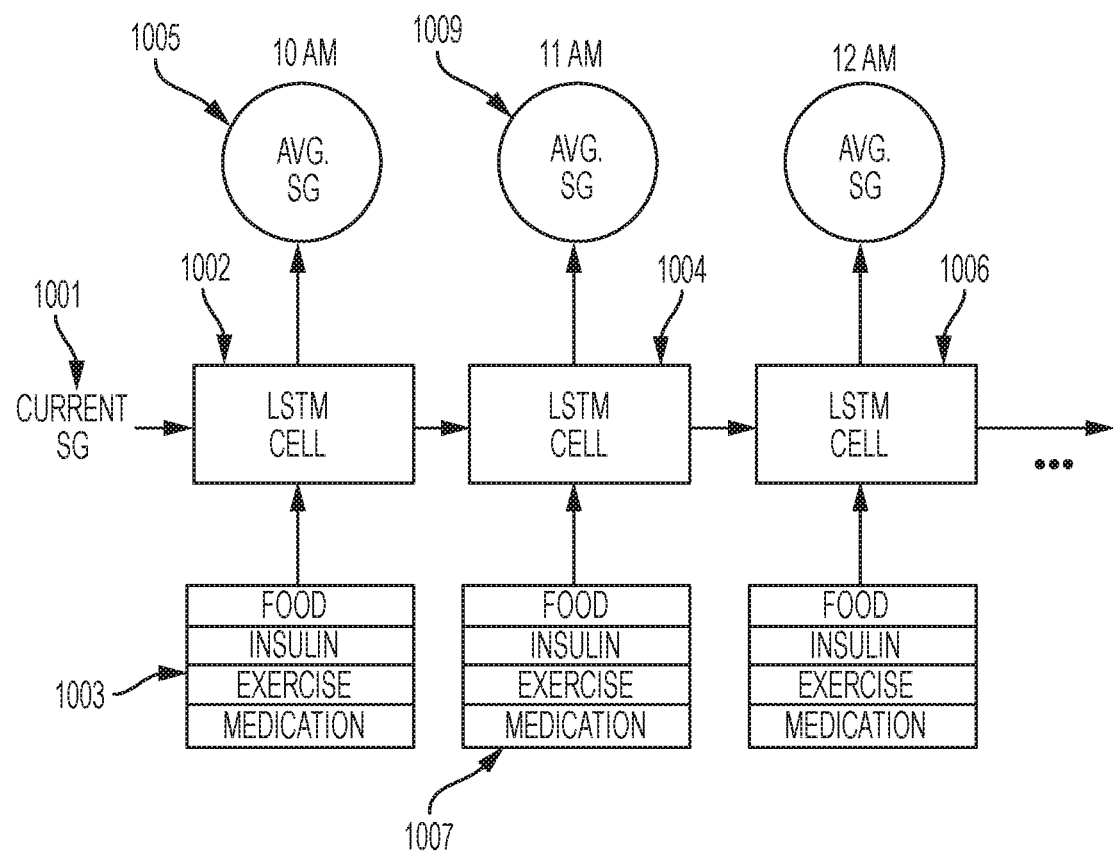
FIG. 10 depicts a block diagram of an hourly forecasting model suitable for use in connection with an exemplary embodiment of the forecasting process of FIG. 8.

Referring to FIGS. 8-9, in one or more exemplary embodiments, based on the current time of day (e.g., 9:45 AM), the current sensor glucose measurement value (e.g., 110 mg/dL), and potentially other recent patient data (e.g., recent meals, exercise, or boluses) and/or the current operating context, the forecasting process 800 calculates or otherwise determines predicted patient behavior for the 10 AM hourly interval and subsequent hourly intervals for which the patient's glucose levels are to be forecast. FIG. 10 depicts a graphical representation of a part of a recurrent neural network including hourly LSTM cells configured to calculate forecasted glucose levels depicted in FIG. 9 using the predicted patient behavior for future hourly intervals and the patient's current sensor glucose measurement data. In this regard, an average sensor glucose value for the current interval 1001 is input to the 10 AM hourly interval LSTM cell 1002 along with the predicted patient behavior 1003 for the 10 AM hourly interval (e.g., the predicted amount of carbohydrates consumed, insulin delivered, exercise, medication, and the like for the patient during the 10 AM to 11 AM time period). Depending on the embodiment, the current interval sensor glucose value 1001 may be realized as the current or most recent sensor glucose measurement value (e.g., 110 mg/dL), an average of the current and preceding sensor glucose measurement values obtained during the current interval (e.g., an average of the sensor glucose measurement values timestamped between 9:00 AM and 9:45 AM), or another sensor glucose value calculated based at least in part on the current sensor glucose measurement value. For example, the current sensor glucose measurement value and other recent behavior may be utilized to predict the patient's glucose level for the remainder of the current time interval (e.g., from 9:45 AM to 10 AM), which in turn, may be averaged, weighted, or otherwise combined with the average of the preceding sensor glucose measurement values obtained during the current interval (e.g., from 9 AM to 9:45 AM) to obtain an estimated average sensor glucose measurement value for the current time interval.

Based on the average sensor glucose value for the current interval 1001 and the predicted patient behavior 1003 for the 10 AM interval, the LSTM cell 1002 calculates or otherwise determines an average glucose value 1005 associated with the 10 AM interval utilizing the forecasting model for the 10 AM hourly interval that was determined based on the subsets of the patient's historical patient data associated with the 10 AM hourly interval (e.g., task 804). Here, it should be noted that in one or more embodiments, the amount of active insulin or carbohydrates are not necessarily required to be calculated for the 10 AM interval or input to the LSTM cell 1002 since the active insulin, carbohydrates, and/or a proxy therefore may be obtained from a preceding LSTM cell and scaled, reduced, discarded, or otherwise adjusted according to the model associated with the LSTM cell 1002. The average glucose value 1005 associated with the 10 AM interval (e.g., 115 mg/dL) is displayed on the forecast region 902 of the GUI display 900 in association with the 10 AM hourly interval. The forecasted 10 AM glucose value 1005 is also input to the 11 AM hourly interval LSTM cell 1004 along with the predicted patient behavior 1007 for the 11 AM hourly interval (e.g., the predicted amount of carbohydrates consumed, insulin delivered, exercise, medication, and the like for the patient during the 11 AM to 12 PM time period). The LSTM cell 1004 calculates or otherwise determines an average glucose value 1009 associated with the 11 AM interval utilizing the forecasting model for the 11 AM hourly interval that was determined based on the subsets of the patient's historical patient data associated with the 11 AM hourly interval (e.g., task 804). The forecasted glucose value 1009 for the 11 AM interval (e.g., 110 mg/dL) is displayed on the forecast region 902 of the GUI display 900 in association with the 11 AM hourly interval and input to the 12 PM hourly interval LSTM cell 1006 for determining a forecasted glucose value for the 12 PM interval (e.g., 100 mg/dL), and so on.

In one or more exemplary embodiments, the forecasted glucose values in the glucose forecast region 902 are displayed or otherwise rendered with visually distinguishable characteristics that indicate the relationship of an individual forecasted glucose value with respect to one or more threshold values. For example, in the illustrated embodiment of FIG. 9, forecasted glucose values within a target range of glucose values for the patient (e.g., between 80 mg/dL and 140 mg/dL) are rendered using a visually distinguishable characteristic that indicates those values are normal, desirable, or otherwise acceptable (e.g., a green color), with forecasted glucose values outside the target range being rendered using a different visually distinguishable characteristic that indicates those values are potentially problematic or undesirable (e.g., a red color). In this regard, for the illustrated embodiment, the forecasted glucose values associated with the 4 PM and 5 PM hourly intervals in the glucose forecast region 902 may be rendered in red to indicate they are below a lower threshold value for the patient's target glucose range indicative of a potential hypoglycemic event being forecasted for the patient at or around those times, while the forecasted glucose values preceding 4 PM in the glucose forecast region 902 may be rendered in green to indicate the patient's glucose is forecasted to be within the target range for the next 6 hours.

In one or more embodiments, the glucose forecast region 902 is scrollable or otherwise adjustable to allow the patient or user to view forecasted glucose values further into the future. For example, in one or more embodiments, the glucose forecast region 902 is scrollable or otherwise adjustable to allow the patient or user to view forecasted glucose values for the next 24 hours. Additionally, it should be noted that in some embodiments, the forecasted glucose values in the glucose forecast region 902 may be dynamically updated in real-time in response to changes to the patient's current sensor glucose measurement value, the current operational context, or other real-time behaviors or activities by the patient.

Figure 11:
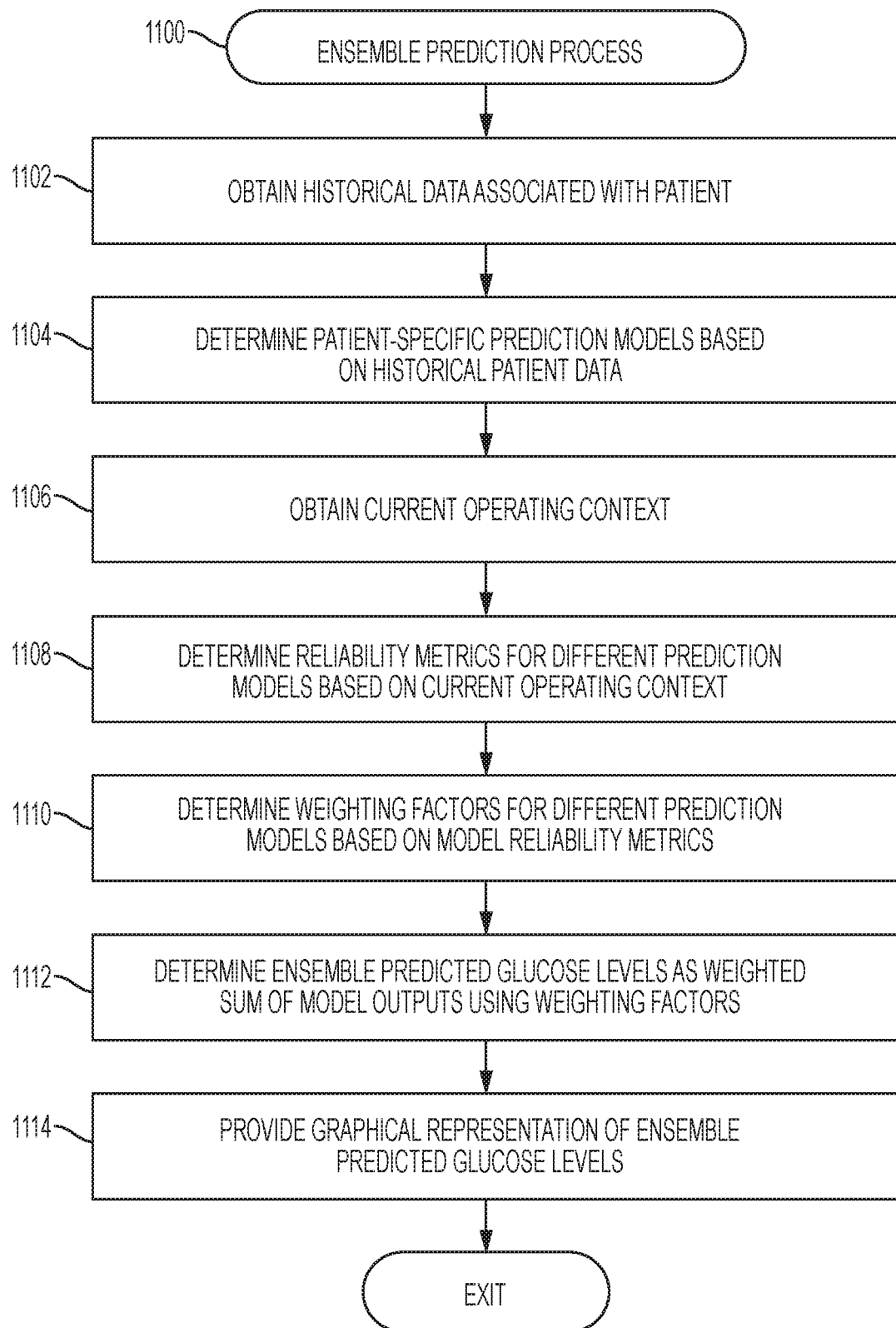
FIG. 11 is a flow diagram of an exemplary ensemble prediction process suitable implementation in connection with a patient data management system in one or more exemplary embodiments.

Referring now to FIG. 11, in accordance with one or more embodiments, an ensemble prediction process 1100 may be performed to determine an ensemble prediction for the physiological condition of the patient as a combination of predicted values determined using a plurality of different prediction models. Since the different prediction models may utilize different input variables, different prediction horizons, and/or different formulas or techniques for determining future glucose values, the ensemble prediction of the patient's glucose level may better reflect the potential variability in the patient's future glucose level rather than reliance on any individual prediction model. In this regard, forecasted hourly glucose values determined in accordance with the forecasting process 800 may be weighted or otherwise combined with predicted glucose values for the patient determined using other prediction models to obtain an ensemble prediction of the patient's glucose level with respect to time that reflects the relative reliability or accuracy of the respective prediction models with respect to time.

The various tasks performed in connection with the ensemble prediction process 1100 may be performed by hardware, firmware, software executed by processing circuitry, or any combination thereof. For illustrative purposes, the following description refers to elements mentioned above in connection with FIGS. 1 and 6-7. In practice, portions of the ensemble prediction process 1100 may be performed by different elements of a patient data management system 100 or an infusion system 600, such as, for example, the server 102, the electronic device(s) 106, an infusion device 602, and/or the pump control system 620, 700. It should be appreciated that the ensemble prediction process 1100 may include any number of additional or alternative tasks, the tasks need not be performed in the illustrated order and/or the tasks may be performed concurrently, and/or the ensemble prediction process 1100 may be incorporated into a more comprehensive procedure or process having additional functionality not described in detail herein. Moreover, one or more of the tasks shown and described in the context of FIG. 11 could be omitted from a practical embodiment of the ensemble prediction process 1100 as long as the intended overall functionality remains intact.

The ensemble prediction process 1100 begins by retrieving or otherwise obtaining historical data associated with a particular patient and developing, training, or otherwise determining multiple different patient-specific glucose prediction models based on the patient's historical data (tasks 1102, 1104). In this regard, in addition to determining a glucose forecasting model as described above in the context of the forecasting process 800, one or more additional models for the patient may be determined based on the patient's historical data 120 that predict the patient's future glucose levels in a different way (e.g., using a different algorithm or modeling technique, etc.), based on different input variables, with a different level of temporal granularity (e.g., on a minute-by-minute basis, an hourly basis, etc.), and/or the like. It should be noted that in practice there are numerous different types of predictive models that could be utilized, and the subject matter described herein is not intended to be limited to any particular type or combination of models, techniques, or methods used to predict glucose levels.

For example, in one or more embodiments, in addition to a patient-specific neural network-based forecasting model, an autoregressive integrated moving average (ARIMA) model for predicting future glucose levels is also determined using the patient's historical data. In this regard, the ARIMA model predicts future glucose levels based on cyclical patterns in the patient's historical data, which may be correlated to different events and/or operational contexts. In exemplary embodiments, the ARIMA model is configured to determine predicted glucose values for the patient at increments in the future corresponding to the sampling rate associated with the glucose sensing arrangement 604 and/or the patient's historical sensor glucose measurement data. For example, in one embodiment, the glucose sensing arrangement 604 provides new or updated sensor glucose measurement values every 5 minutes, and the ARIMA model is configured to determine predicted glucose values at 5 minute intervals into the future. In one or more exemplary embodiments, machine learning or similar techniques are utilized to determine which combination of historical delivery data, historical auxiliary measurement data, historical event log data, historical geolocation data, and other historical or contextual data are correlated to or predictive of the historical sensor glucose measurement data, and then determines a corresponding ARIMA model for calculating or predicting future sensor glucose measurement values based on that set of input variables and a preceding subset of historical sensor glucose measurement values. In this regard, the trajectory of the preceding subset of historical sensor glucose measurement values in conjunction with concurrent or preceding events or operational contexts that are historically correlative to or predictive of changes in the patient's sensor glucose level influence the predicted future sensor glucose measurement values determined using the model. In one embodiment, the training of the autoregressive component of the ARIMA model attempts to identify the capability of the patient's glucose level to regress on its own while the moving average component of the ARIMA model attempts to compensate for a slow background shift in the patient's glucose levels.

In one or more embodiments, a patient-specific physiological model for predicting future glucose levels is also determined using the patient's historical data in a manner that attempts to emulate the patient's pharmacodynamics and pharmacokinetics with compensation for inter- and intra-personal variance. Similar to the ARIMA model, the patient-specific physiological model may be configured to determine predicted glucose values for the patient at increments in the future corresponding to the sampling rate associated with the glucose sensing arrangement 604 and/or the patient's historical sensor glucose measurement data. That said, the patient-specific physiological model may determine the predicted glucose values in a different manner than the ARIMA model and/or based on different input variables than those used by the ARIMA model. For example, in one or more embodiments, one or more patient-specific physiological parameters (e.g., glucose rate of appearance, insulin action, and/or the like) are determined for the patient based on relationships between the patient's historical sensor glucose measurement data, historical meal data, historical delivery data, historical bolus data, and/or the like. The physiological model utilizes the patient-specific physiological parameters to predict future sensor glucose measurement values based on the patient's current or recent sensor glucose measurement values, current insulin on board, recent meal data, and/or the like. In this regard, the output of the patient-specific physiological parameters represents the expected glucose levels for the patient based on the patient's historical physiological response given the current amount of insulin on board and/or amount of carbohydrates yet to be metabolized by the patient.

Still referring to FIG. 11, in exemplary embodiments, after determining or otherwise obtaining a plurality of different patient-specific glucose prediction models, the ensemble prediction process 1100 continues by identifying or otherwise obtaining the current operational context for the patient and calculating or otherwise determining reliability metrics associated with the different patient-specific glucose prediction models for different prediction horizons in advance of the current time of day based on the current operational context (tasks 1106, 1108). In this regard, the current time of day, the current day of the week, the current geographic location, the current network address and/or type of network connectivity, and/or other contextual data associated with a device 106, 602 associated with the patient is identified or otherwise obtained. Based on the current operational context, subsets of the patient's historical data 120 corresponding to the current operational context are obtained and utilized to determine one or more accuracy or reliability metrics associated with the different glucose prediction models. For example, if the current operational context indicates it is 8 AM on a Wednesday and the patient is at home, prior subsets of the patient's historical data 120 having associated timestamps at or around 8 AM on Wednesdays and/or having associated geographic locations corresponding to the patient's home geographic location may be obtained and then utilized to determine the reliability of the different glucose prediction models.

For each prediction model, the appropriate input variables are obtained from the relevant subset of the patient's historical data, and the calculated glucose values output by the model are compared to the patient's historical sensor glucose measurement values at corresponding times to obtain a reliability metric for the model. For example, a mean absolute difference, standard deviation, or other statistical measurement may be calculated by comparing a set of output values from a glucose prediction model corresponding to a prediction horizon after a point of time (e.g., the four hours of predicted glucose values following the 8 AM reference point) to the corresponding historical glucose measurement values (e.g., the four hours of historical patient sensor glucose measurement values following the 8 AM reference point on a Wednesday). In one or more embodiments, the reliability metrics are determined for hourly intervals, for example, by calculating the mean absolute difference within the first hour after the prediction time (e.g., using values corresponding to the 8 AM to 9 AM timeframe), the mean absolute difference within the second hour after the prediction time (e.g., using values corresponding to the 9 AM to 10 AM timeframe), and so on. In this regard, the reliability metric associated with each particular prediction model may vary depending on the particular prediction horizon or time window in advance of the current prediction time.

Based on the reliability metrics associated with the different prediction models, the ensemble prediction process 1100 calculates or otherwise determines weighting factors to be associated with the outputs of the different patient-specific glucose prediction models for different prediction horizons in advance of the current time of day and then calculates or otherwise determines ensemble predicted glucose values within those different prediction horizons as weighted averages of the outputs of the different patient-specific glucose prediction models using those weighting factors (tasks 1110, 1112). In this regard, based on the relationship between the reliability metrics across the different patient-specific glucose prediction models for a particular prediction horizon, time window or sampling time, weighting factors may be assigned to the different models accordingly to increase the influence of the more reliable model(s) on the ensemble predicted glucose values within that prediction horizon.

For example, if the patient's ARIMA model is fifty percent more reliable than the patient's hourly forecasting model for the second hour in advance of the current prediction time (e.g., the 9 AM to 10 AM timeframe), the predicted glucose values output by the ARIMA model for the second hour may be assigned a weighting factor that is fifty percent higher than the weighting factor assigned to the hourly forecasting model. Ensemble predicted values for that prediction horizon (i.e., the second hour in advance of the current time) may then be determined as the weighted average of the 5-minute predicted glucose values output by the ARIMA model for that time frame (e.g., the 9 AM to 10 AM values) and the hourly forecast glucose value output by the hourly forecast model (e.g., the forecasted average glucose level for the 9 AM to 10 AM time window), resulting in 5-minute ensemble predicted values that are composed of 60% of the ARIMA predicted glucose value at that particular 5 minute sampling time (e.g., the ARIMA predicted glucose value for 9:05 AM) and 40% of the hourly forecast glucose value for the prediction horizon. However, for the third hour in advance of the current prediction time, the patient's hourly forecasting model may be fifty percent more reliable than the predicted glucose values output by the ARIMA model for the third hour, resulting in the weighting factor assigned to the hourly forecasting model being fifty percent higher than that assigned to the ARIMA model, thereby resulting in 5-minute ensemble predicted values that are composed of 40% of the ARIMA predicted glucose value at a particular 5 minute sampling time (e.g., the ARIMA predicted glucose value for 10:05 AM, 10:10 AM, and so on) and 60% of the hourly forecast glucose value for the prediction horizon (e.g., the hourly forecasted glucose value for the 10 AM to 11 AM time period).

Figure 12:
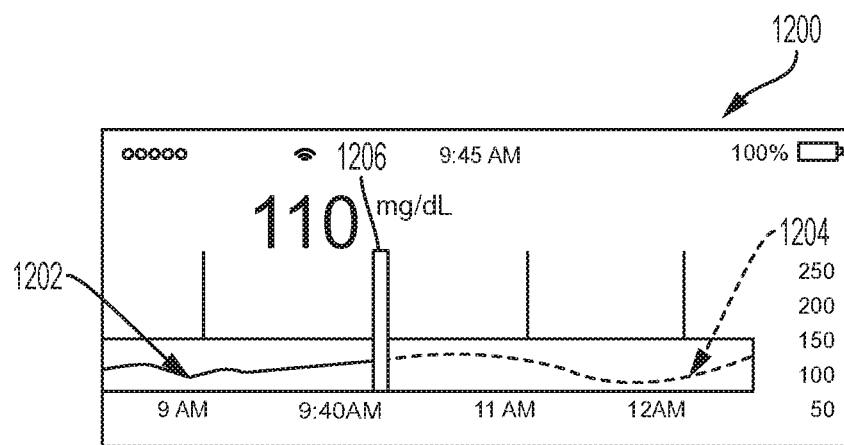
FIG. 12 depicts an exemplary GUI display suitable for presentation on a client electronic device in accordance with an exemplary embodiment of the ensemble prediction process of FIG. 11.

After determining an ensemble glucose prediction into the future, the ensemble prediction process 1100 continues by generating or otherwise providing a graphical representation of the ensemble predicted glucose values to the patient or other user (task 1114). For example, as depicted in FIG. 12, a GUI display 1200 may be presented on a client electronic device 106 and/or infusion device 602 that includes a graphical representation 1202 of the patient's sensor glucose measurement data with respect to time preceding a marker 1206 or similar graphical indication of the current time, followed by a graphical representation 1204 of the ensemble predicted glucose values with respect to time after the marker indicating the current time. In one or more embodiments, the reliability metrics associated with the ARIMA model, physiological model, or other shorter term prediction models decrease relative to the reliability metrics associated with the hourly forecasting model as the prediction horizon advances further into the future in advance of the current time, such that the graphical representation of the ensemble predicted glucose values converge toward the hourly forecast glucose levels as the patient or user scrolls, slides, or otherwise adjusts the GUI display 1200 to advance the prediction horizon associated with the displayed values. In this regard, scrolling or adjusting the sensor glucose measurement display region 904 may result in updating the sensor glucose measurement display region 904 to present the GUI display 1200 depicting the ensemble glucose prediction 1204 extending into the future from the current time marker 1206.

In one or more exemplary embodiments, the earlier portions of the ensemble glucose prediction 1204 are weighted more heavily toward outputs of prediction models that are more reliable in the short-term while portions of the ensemble glucose prediction 1204 further into the future are weighted more heavily toward outputs of prediction models having better longer term reliability. For example, the portion of the ensemble glucose prediction 1204 from 10 AM to 11 AM may be composed of 60% of the output of the patient's ARIMA model and 40% of the patient's hourly forecasting model, while the subsequent portion of the ensemble glucose prediction 1204 from 11 AM to 12 PM may be composed of 40% of the output of the patient's ARIMA model and 60% of the patient's hourly forecasting model, the portion of the ensemble glucose prediction 1204 from 12 PM to 1 PM may be composed of 30% of the output of the patient's ARIMA model and 70% of the patient's hourly forecasting model, and so on.

Figure 13:
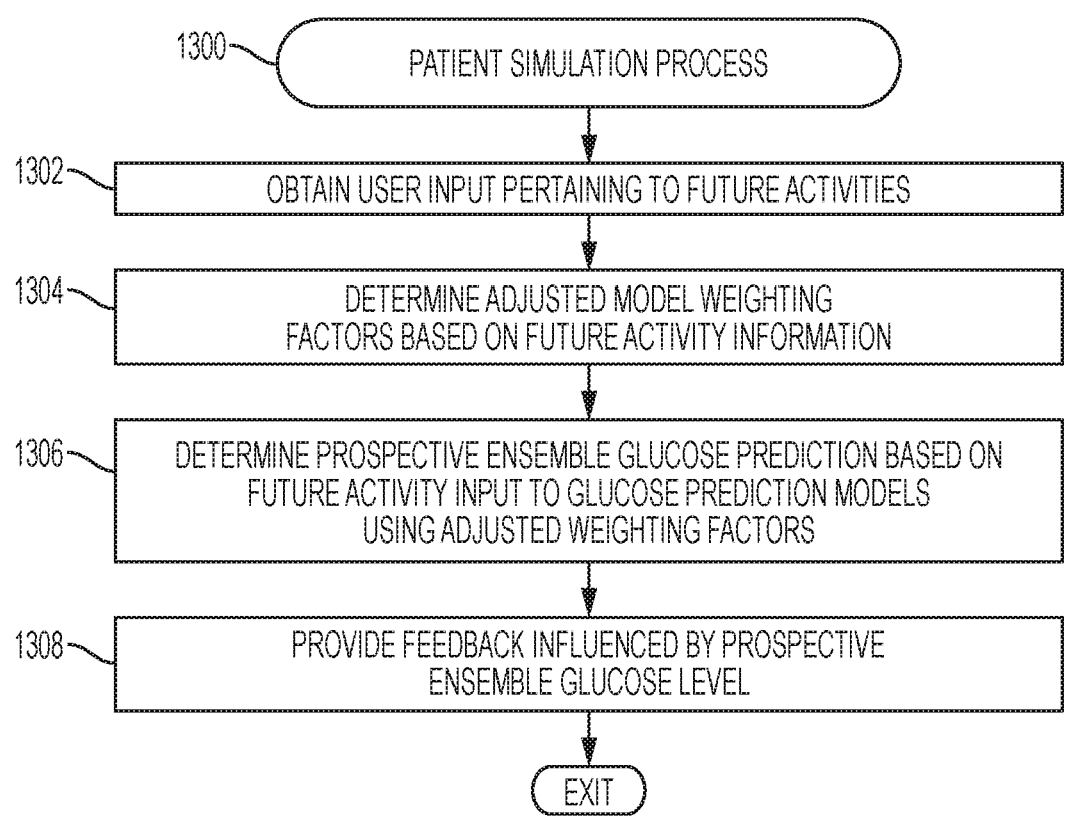
FIG. 13 is a flow diagram of an exemplary patient simulation process suitable implementation in connection with a patient data management system in one or more exemplary embodiments.

FIG. 13 depicts an exemplary patient simulation process 1300 suitable for implementation in connection with the ensemble prediction process 1100 to simulate or otherwise predict how different events or actions by the patient are likely to influence the patient's glucose levels in the future. The various tasks performed in connection with the patient simulation process 1300 may be performed by hardware, firmware, software executed by processing circuitry, or any combination thereof. For illustrative purposes, the following description refers to elements mentioned above in connection with FIGS. 1 and 6-7. In practice, portions of the patient simulation process 1300 may be performed by different elements of a patient data management system 100 or an infusion system 600, such as, for example, the server 102, the electronic device(s) 106, an infusion device 602, and/or the pump control system 620, 700. It should be appreciated that the patient simulation process 1300 may include any number of additional or alternative tasks, the tasks need not be performed in the illustrated order and/or the tasks may be performed concurrently, and/or the patient simulation process 1300 may be incorporated into a more comprehensive procedure or process having additional functionality not described in detail herein. Moreover, one or more of the tasks shown and described in the context of FIG. 13 could be omitted from a practical embodiment of the patient simulation process 1300 as long as the intended overall functionality remains intact.

The patient simulation process 1300 begins by receiving or otherwise obtaining user input indicative of future events, actions or other activities for a patient (task 1302). In this regard, the patient or another user may input or otherwise provide information that characterizes, quantifies, or otherwise defines actions or events that are anticipated, contemplated, or otherwise being considered by the patient. For example, the user input may indicate a prospective amount of carbohydrates to be consumed by the patient, a prospective amount of exercise to be performed by the patient, a prospective bolus amount of insulin to be administered by the patient, and/or the like. Additionally, the user input may indicate a time of day associated with the prospective activities (e.g., an expected meal time for a future amount of carbohydrates), a time window or duration of time of interest, or other temporal information characterizing the prospective activity by the patient. In some events, the prediction engine 708 may automatically predict future actions or events and corresponding parameters or criteria associated therewith based on the patient's historical measurement data, event log data, contextual data, and/or the like. In such embodiments, the patient or another user may input or otherwise provide confirmation of the predicted future events, or otherwise adjust one or more characteristics associated with the predicted future events (e.g., adjusting the future timing, an amount, duration, type or other character associated with the event, and/or the like).

The patient simulation process 1300 continues by calculating or otherwise determining adjusted weighting factors for combining output from the patient's glucose prediction models into an ensemble prediction based on the current operational context and the input future activity information (task 1304). In this regard, similar to as described above in the context of the ensemble prediction process 1100, the patient simulation process 1300 calculating or otherwise determining reliability metrics associated with the different patient-specific glucose prediction models for different prediction horizons in the future based on the current time of day and other operational contexts in a manner that also accounts for the input future activity information.

In one or more embodiments, when selecting subsets of the patient's historical data 120 for determining reliability metrics, the patient simulation process 1300 may exclude, from the subsets of the patient's historical data 120 corresponding to the current operational context, any subset of the patient's historical data 120 corresponding to the current operational context that does not contain one or more of the input future activities within the prediction horizon or otherwise within a threshold period of time from the current time of day. For example, if the current operational context indicates it is 8 AM on a Wednesday and the patient is at home, and the user input indicates the patient is intending to consume carbohydrates or otherwise experience a meal event within a threshold amount of time, only prior subsets of the patient's historical data 120 having associated timestamps at or around 8 AM on Wednesdays and/or having associated geographic locations corresponding to the patient's home geographic location that are also have a contemporaneous or concurrent meal within a threshold amount of time after 8 AM are selected for analysis. In this regard, varying the data set used in calculating the reliability metrics associated with the different prediction models may result in prospectively-adjusted reliability metric values associated with the respective prediction models that are different from the normal reliability metric values that would otherwise be associated with the respective prediction models in the absence of accounting for future activity. The patient simulation process 1300 then determines prospectively-adjusted weighting factors based on the relationship between the adjusted reliability metrics across the different patient-specific glucose prediction models. In a similar manner as described above, the prospectively-adjusted weighting factors may also vary with respect to the prediction time in advance of the current time.

Still referring to FIG. 13, after determining weighting factors prospectively-adjusted to account for the input future activity information, the patient simulation process 1300 calculates or otherwise determines a prospective ensemble glucose prediction based on the input future activity information using the prospectively-adjusted weighting factors (task 1306). In this regard, the input future activity information is provided as an input to one or more of the patient's glucose prediction models to thereby alter or influence the predicted glucose values output by the model(s) in a manner that accounts for the prescribed future event(s) at the corresponding time(s) in the future. For example, if the user input indicates the patient is likely to eat a meal at a particular time in the future, the input meal information is provided as an input to the LSTM cell of the patient's hourly forecasting model that encompasses or otherwise corresponds to that time in the future, thereby influencing the forecasted glucose value for that time interval and/or subsequent time intervals. As another example, if the user input indicates the patient is likely to administer a bolus of insulin at the current time, the input bolus amount may be provided to each of the patient's glucose prediction models in a manner that accounts for the bolus amount of insulin upon initialization (e.g., by adding the input bolus amount to the current amount of active insulin associated with the current time of day).

After predicted glucose values accounting for the prospective patient activity are calculated using each of the patient's glucose prediction models, ensemble predicted values are determined as a weighted average of the respective predicted glucose values output by the respective glucose prediction models using the prospectively-adjusted weighting factors, in a similar manner as described above (e.g., task 1112). By virtue of prospectively adjusting the weighting factors as well as utilizing the future activity as input to the prediction models, the resulting ensemble predicted values effectively simulate or project the patient's glucose level into the future if the patient engages in the input activity. Accordingly, the prospective ensemble prediction may alternatively be referred to herein as the patient's simulated glucose level.

In exemplary embodiments, the patient simulation process 1300 generates or otherwise provides a graphical representation of the patient's simulated glucose level or other feedback that is influenced by the prospective ensemble glucose prediction (task 1308). For example, in some embodiments, a line chart or graph of the patient's simulated glucose level may be presented in response to the input future activity information. In other embodiments, the simulated glucose values may be processed or otherwise analyzed to provide one or more recommendations to the patient (e.g., indication of whether or not to engage in the input activity, or the like).

Figures 14, 15:
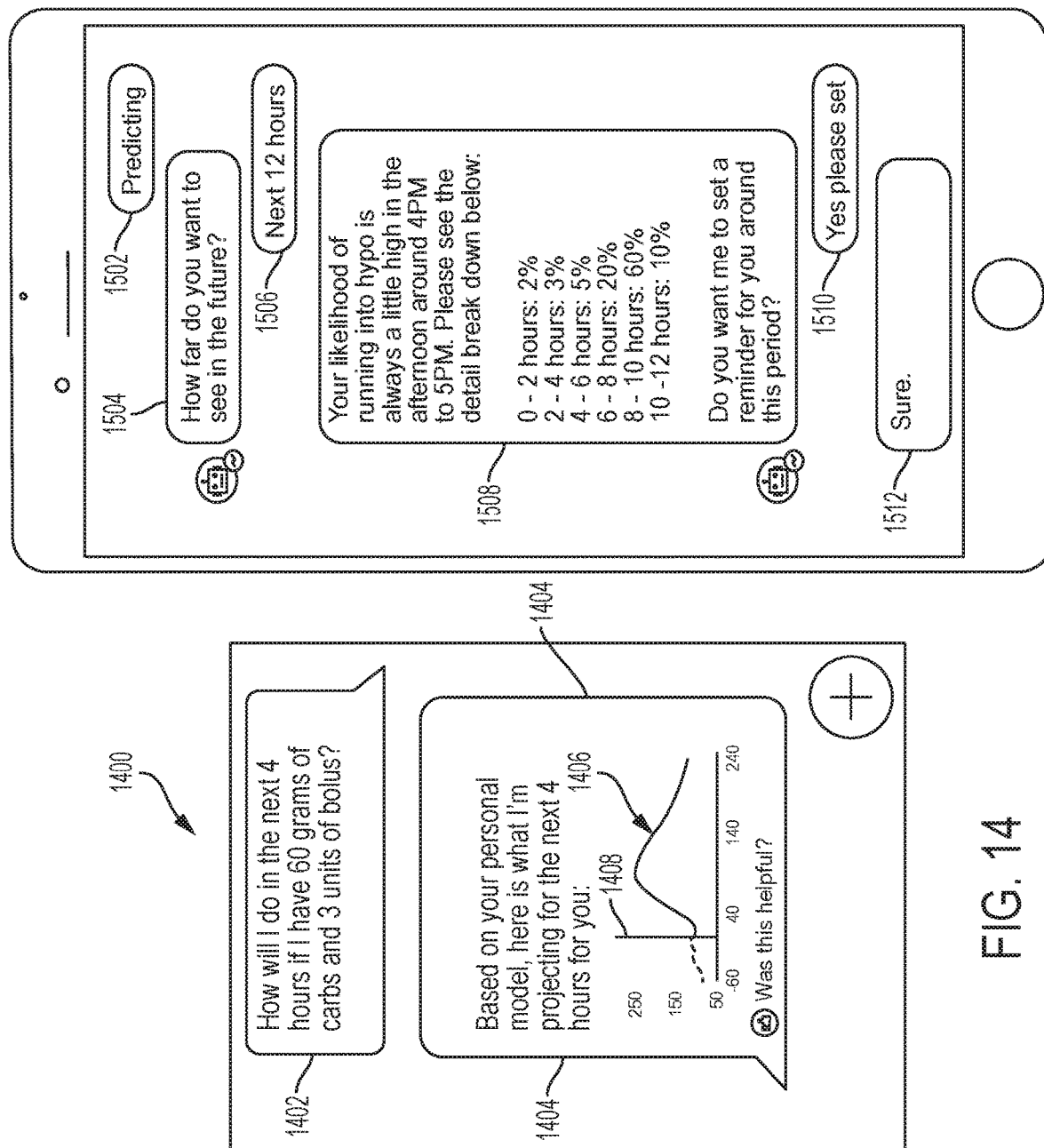
FIGS. 14-16 depicts exemplary GUI displays suitable for presentation on a client electronic device in accordance with various exemplary embodiments of the patient simulation process of FIG. 13.

For example, referring now to FIG. 14 with reference to FIG. 13, in one or more embodiments, the patient simulation process 1300 is performed in conjunction with a conversational interaction with the patient that may be supported by a conversational interaction application 712 at an infusion device 602 or other client device 106. In the illustrated embodiment, the patient manipulates or otherwise interacts with the client device 106, 602 to input that the patient would like to view his or her simulated glucose levels 4 hours into the future if the patient contemporaneously consumes 60 grams of carbohydrates and administers a bolus of 3 units of insulin. In response to receiving the user input, the conversational interaction application 712 may provide the input parameters to the prediction engine 708 for simulating the patient's glucose levels in accordance with the patient simulation process 1300. In this regard, the patient simulation process 1300 determines prospectively-adjusted weighting factors for the patient's prediction models based on the respective reliability metrics associated with the models for the subsequent 4 hours after instances when the patient historically has consumed carbohydrates and/or administered a bolus of insulin at or around the current time of day. The patient simulation process 1300 then inputs or otherwise provides 60 grams of carbohydrates and 3 units of insulin to each of the patient's prediction models to initialize the models as if the carbohydrates are being consumed and the insulin is being delivered contemporaneously or otherwise upon startup of the model. Thereafter, predicted glucose values for the patient are calculated for the next 4 hours into the future using the patient's prediction models initialized with 60 grams of carbohydrates and 3 units of insulin. Prospective ensemble predicted glucose values for the next 4 hours are then determined as a weighted average of the predicted glucose values accounting for the contemporaneous intake of carbohydrates and insulin using the prospectively-adjusted weighting factors.

After determining the prospective ensemble predicted glucose values for the patient, the prediction engine 708 may provide the prospective ensemble predicted glucose values to the conversational interaction application 712 for presentation to the patient within the context of the ongoing conversational interaction. In this regard, the conversation GUI display 1400 including a graphical representation 1402 of the user input is updated to include a conversational response 1404 to the user input that is influenced by the simulated glucose values. In the illustrated embodiment, the conversational response 1404 includes a graphical representation 1406 of the patient's simulated glucose level (e.g., a line chart of the prospective ensemble predicted glucose values) for the next 4 hours following a marker 1408 indicating the current time of day.

FIG. 15 depicts another exemplary GUI display 1500 depicting a conversational interaction that may incorporate the ensemble prediction process 1100 of FIG. 11 and/or the patient simulation process 1300 of FIG. 13. In the illustrated embodiment, the conversational interaction application 712 receives an initial user input 1502 and analyzes the initial user input to determine the patient is interested in a prediction of his or her physiological condition. The conversational interaction application 712 generates or otherwise provides a conversational response 1504 that prompts the patient to input or otherwise provide an indication of a prediction horizon and/or potentially other parameter for the prediction to be performed. For example, in some embodiments, the conversational interaction application 712 may prompt the patient to provide input of any anticipated activities within the input prediction horizon for prospectively adjusting the prediction in accordance with the patient simulation process 1300.

In response to receiving a subsequent user input 1506 indicating that the patient is interested in a prediction over the next 12 hours, the conversational interaction application 712 commands, signals, or otherwise instructs the prediction engine 708 to predict the patient's glucose level for the next 12 hours. The prediction engine 708 performs the ensemble prediction process 1100 to calculate or otherwise determine ensemble predicted glucose values for the patient over the next 12 hours based on the patient's current or recent glucose measurements, current active insulin, the current operational context, and/or the like as described above. In the illustrated embodiment, the prediction engine 708 also utilizes the reliability metrics associated with the respective prediction models (e.g., standard deviations, mean absolute differences, and/or the like) to probabilistically determine the likelihood of one or more physiological events (e.g., a hypoglycemic event, a hyperglycemic event, and/or the like) within the prediction horizon based on the ensemble predicted glucose values. The prediction engine 708 provides the ensemble predicted glucose values and corresponding physiological event probabilities to the conversational interaction application 712, which generates a conversational response 1508 providing feedback influenced by the patient's ensemble predicted values. For example, the illustrated conversational response 1508 includes graphical representations of hypoglycemic event probabilities with respect to different intervals within the prediction horizon along with an indication of when the probability of a hypoglycemic event based on the current time of day.

In the illustrated embodiment, the conversational response 1508 also prompts the patient for whether or not the patient could like to configure one or more settings at the device 106, 602 based on the predicted glucose levels. In response to receiving a user input 1510 indicating a desire to configure a reminder, the conversational interaction application 712 may configure itself to generate or otherwise provide a reminder at the time of day when the probability of a hypoglycemic event is highest based on the ensemble predicted values and reliability metrics and then generate or otherwise provide a conversational response 1512 confirming or otherwise indicating the reminder has been set.

Figure 16:
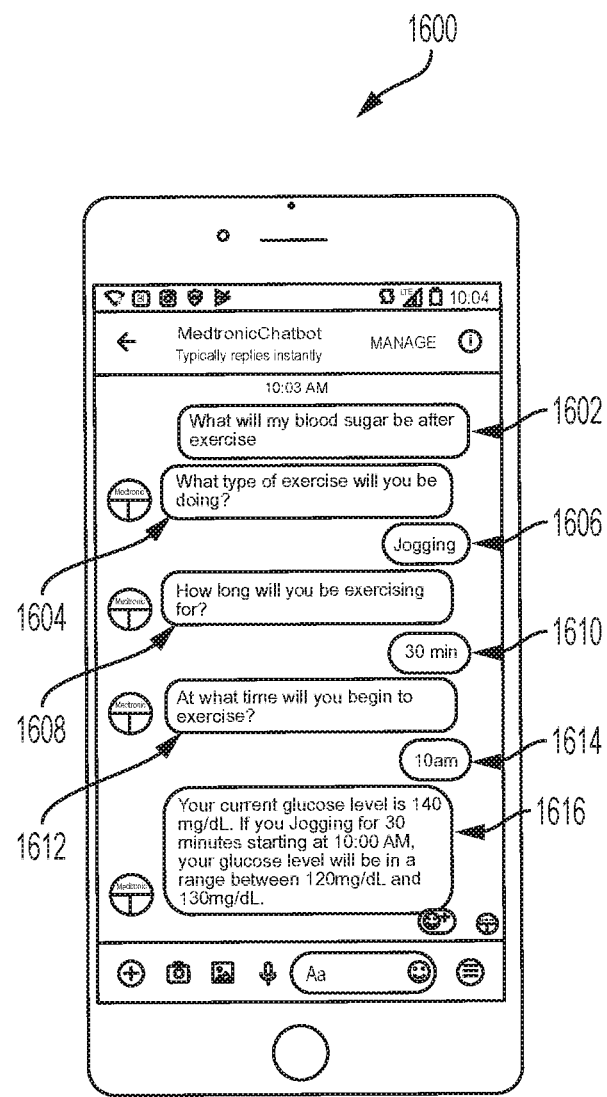

FIG. 16 depicts another exemplary GUI display 1600 depicting a conversational interaction that may incorporate one or more of the processes 300, 800, 1100, 1300 described above. In the illustrated embodiment, the conversational interaction application 712 receives an initial conversational user input 1602 and analyzes the initial user input to determine the patient is interested in a prediction of his or her physiological condition in response to a future exercise event. The conversational interaction application 712 generates or otherwise provides a sequence of conversational responses 1604, 1608, 1612 that prompts the patient to conversationally input 1606, 1610, 1614 and define anticipated attributes for the future exercise event, such as, the anticipated type of event, the anticipated duration of the event, and the anticipated timing of the event. After the attributes of the future event are defined, the prediction engine 708 performs the patient simulation process 1300 to calculate or otherwise determine a prospective glucose level for the patient after the event (e.g., at a time corresponding to a sum of the input timing 1614 for the event and the input duration 1610 for the event) based on the patient's current glucose measurement, current active insulin, the current operational context, with the attributes associated with the future event being input or otherwise provided to the patient's forecasting and prediction models in accordance with the anticipated timing input by the patent.

In some embodiments, to adjust the model weighting factors, reliability metrics, or other aspects of the patient simulation process 1300 to account for the prospective patient activity, the querying process 300 may be performed to obtain data or information characterizing the responses of other similar patients to the prospective future event. For example, the querying process 300 may be performed to identify similar patients based on common links or edges between nodes within a logical database layer and obtain historical measurement data for those similar patients' glycemic responses to the input type of activity for the input duration at the input time of day (e.g., sensor glucose measurement data for similar patients when jogging at 10 AM for the following 30 minutes). The average or typical physiological response by similar patents may then be utilized to adjust or otherwise augment the individual patient's physiological prediction model, which, in turn is then utilized by the ensemble prediction process 1100 and/or the patient simulation process 1300 to obtain an prospective ensemble glucose prediction that is influenced by the patient's hourly glucose forecasts accounting for the input future exercise (e.g., by inputting the exercise attributes to the 10 AM LSTM unit) in combination with the adjusted physiological prediction for the patient's glucose level.

As another example, a patient may conversationally interact with a client device 106, 602 to obtain a prediction of what his or her sensor glucose level is likely to be upon waking up in the morning. Based on the patient's historical event log data, an estimated sleep duration and/or estimated wake up time for the patient may be determined, and which may be utilized to adjust the model weighting factors and be provided as input to the patient's prediction models to obtain a prospective ensemble prediction of the patient's glucose level at or around the estimated wake up time. In one or more embodiments, the prospective ensemble glucose prediction is also utilized to generate one or more recommendations to the patient. For example, if the prospective ensemble glucose prediction at the estimated wakeup time is outside of the target range of glucose values, the querying process 300 may be performed to identify actions performed by similar patients at or before bed time or otherwise associated with the overnight period that resulted in a change in those patients' glucose levels that, if a corresponding increase or decrease occurred with respect to the current patient, would result in the prospective ensemble glucose prediction at the estimated wakeup time being within the target range. In this regard, the querying process 300 may be utilized to identify a recommended amount of carbohydrates the patient should eat, a recommended amount of insulin the patient should bolus, and/or a recommended amount of exercise that the patient should perform prior to sleeping to achieve a desired glucose level upon waking. If the prospective ensemble glucose prediction at the estimated wakeup time is within the target range of glucose values, other recommendations that are likely to improve the patient's glucose regulation (e.g., increase the percentage of the day within the target glucose range, minimize glucose excursion events, and/or the like) may be determined based on similar patients and provided to the patient, such as, for example, a recommended duration of sleep, a recommended amount of carbohydrates for the following day, a recommended amount of exercise for the following day, and/or the like.

Referring to FIGS. 8-16 and with reference to FIG. 1, in some embodiments, one or more of the processes 800, 1100, 1300 may be implemented in connection with the patient data management system 100 and adapted to leverage the graph data structures in the database 104 to improve the accuracy of the modeling and resulting predictions. In this regard, weighted directional or causal links between nodes or entities may be utilized to identify predictive relationships and corresponding influences on patient outcomes for improved modeling, while such relationships could otherwise be indeterminable or computationally impractical using conventional databases reliant on tables that lack causal and/or probabilistic relationships between entities.

Prospective Therapy Management

Figure 17:
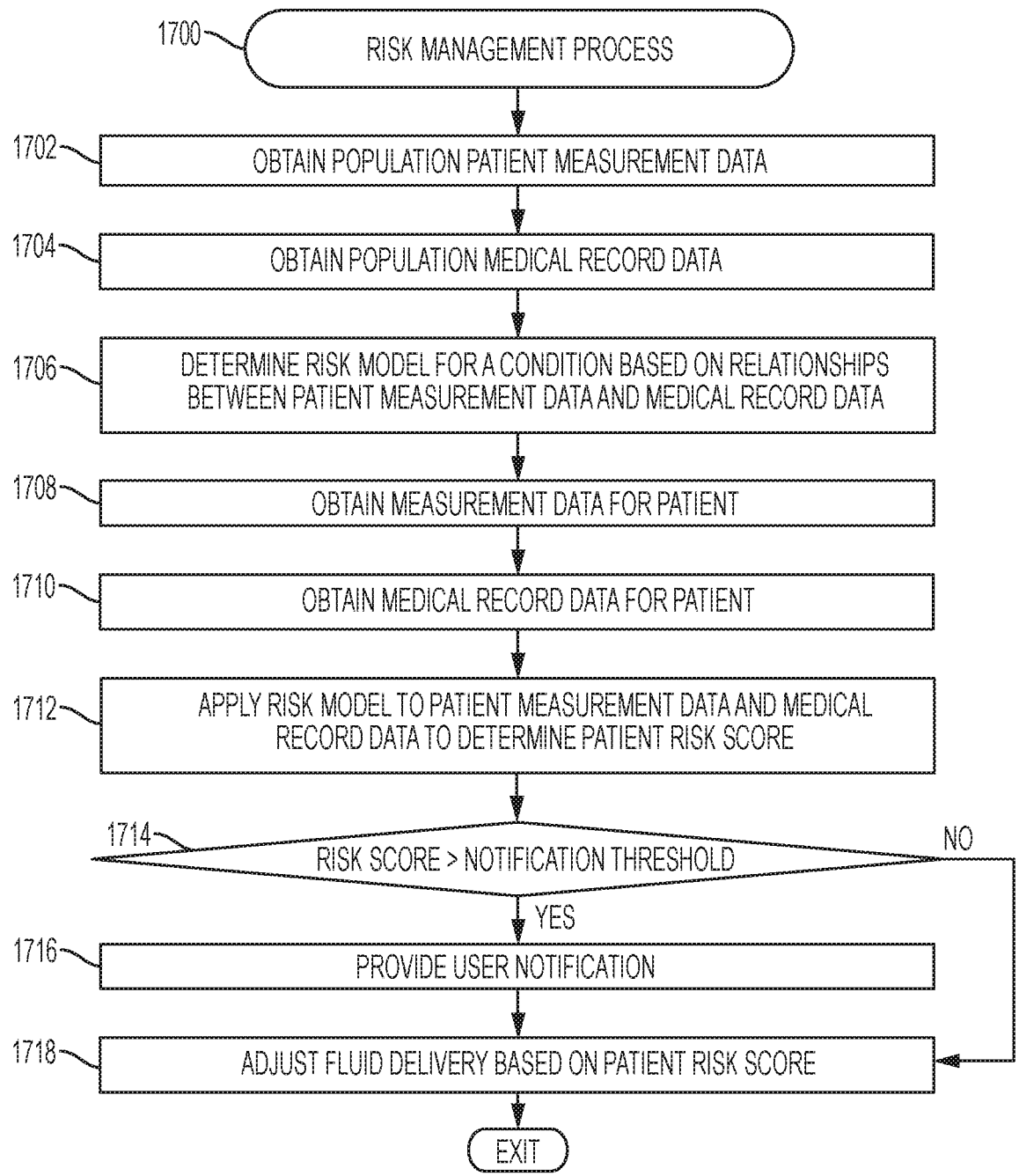
FIG. 17 is a flow diagram of an exemplary risk management process suitable implementation in connection with a patient data management system in one or more exemplary embodiments.

Referring now to FIG. 17, in accordance with one or more embodiments, a risk management process 1700 utilizes measurement data pertaining to a patient's physiological condition in conjunction with the patient's medical records data to calculate or otherwise determine a metric indicative of the patient's risk of experiencing a particular condition. For example, a patient's sensor glucose measurement data or a metric calculated based thereon may be utilized in conjunction with a subset of the patient's medical records data to calculate or otherwise determine a metric indicative of how at risk the patient is for experiencing one or more acute diabetic crises (e.g., severe hypoglycemia, acute diabetic ketoacidosis, hyperosmolarity, and/or the like) and/or long-term complications. In exemplary embodiments, the risk management process 1700 generates or otherwise provides notifications or recommendations pertaining to a condition the patient is at risk of to an end user (e.g., the patient, the patient's healthcare provider, the patient's care partner, and/or the like). For purposes of explanation, the subject matter may be described herein in the context of notifications or recommendations being provided to the patient, however, it should be appreciated that the subject matter described herein is not limited to the type of end user to whom the notifications or recommendations are being provided. In some embodiments, one or more therapy recommendations are provided to the patient in accordance with one or more of the process 1800 and/or the process 1900, as described in greater detail below in the context of FIGS. 18-19. Additionally, in the illustrated embodiment of FIG. 17, the value of the metric indicating the patient's level of risk for a particular condition may be utilized to adjust, modify, or otherwise influence the delivery of fluid by an infusion device 602 associated with the patient and/or otherwise alter the patient's therapy.

The various tasks performed in connection with the risk management process 1700 may be performed by hardware, firmware, software executed by processing circuitry, or any combination thereof. For illustrative purposes, the following description refers to elements mentioned above in connection with FIGS. 1 and 6-7. In practice, portions of the risk management process 1700 may be performed by different elements of a patient data management system 100 or an infusion system 600, such as, for example, the server 102, the electronic device(s) 106, an infusion device 602, and/or the pump control system 620, 700. It should be appreciated that the risk management process 1700 may include any number of additional or alternative tasks, the tasks need not be performed in the illustrated order and/or the tasks may be performed concurrently, and/or the risk management process 1700 may be incorporated into a more comprehensive procedure or process having additional functionality not described in detail herein. Moreover, one or more of the tasks shown and described in the context of FIG. 17 could be omitted from a practical embodiment of the risk management process 1700 as long as the intended overall functionality remains intact.

In the illustrated embodiment, the risk management process 1700 begins by receiving or otherwise obtaining measurement data and medical records data for a patient population (tasks 1702, 1704). For example, the server 102 may retrieve, from the database 104, a subset of historical patient data 120 for a population of patients and a corresponding subset of the electronic medical records data 122 for that patient population. In one embodiment, historical patient data 120 and electronic medical records data 122 are obtained for all common patients across data sets. However, in other embodiments, the patient population may be tailored for a particular demographic or combination of demographic attributes (e.g., by age, gender, income, and/or the like).

After obtaining measurement data and medical records data for a patient population, the risk management process 1700 determines a risk model for a particular condition based on relationships between the measurement data and the medical records data across the patient population (task 1706). In exemplary embodiments, stepwise feature selection, such as recursive feature elimination, is performed to identify which fields or attributes of the patient measurement data and medical records data are most correlative to or predictive of the occurrence of a particular condition within the patient population.

For example, the server 102 may analyze the historical sensor glucose measurement data for the patient population to identify which sensor glucose metrics (e.g., mean sensor glucose measurement value, sensor glucose measurement standard deviation, overnight mean sensor glucose measurement value, percentage of time the sensor glucose measurement value is within range, percentage of time the sensor glucose measurement value is above a hyperglycemia threshold, percentage of time the sensor glucose measurement value is below a hypoglycemia threshold, etc.) for some subset of the patient population are predictive of or correlative to the occurrence of a particular medical diagnosis code within the electronic medical records for that subset of the patient population. In this regard, for a given medical diagnosis code of interest (e.g., hypoglycemia, diabetic ketoacidosis, hyperosmolarity, cardiovascular disease, and/or the like), the server 102 may perform stepwise feature selection across of the different sensor glucose measurement metrics associated with the population patients to identify or otherwise determine a subset of the sensor glucose measurement metrics that are correlative to or predictive of occurrence of that medical condition's diagnostic code within the electronic medical records data 122. Similarly, for the medical condition of interest, the server 102 may analyze the electronic medical records data for the patient population by performing stepwise feature selection to identify which fields or attributes of the patient medical records (e.g., age, gender, income, education level, smoking, A1C values or other laboratory values, insulin status or other medications or therapies, other medical conditions, and/or the like) are correlative to or predictive of occurrence of that medical condition. It should be noted that in some embodiments, operating context data for the patient population may also be analyzed to identify whether any particular operating contexts (e.g., geographic location, temperature, humidity, and/or the like) are correlative to or predictive of occurrence of a particular medical condition.

After identifying the sensor glucose measurement variables and medical record variables that are correlative to or predictive of occurrence of a medical condition, the server 102 then calculates or otherwise determines an equation, function, or model for calculating the probability or likelihood of the occurrence of the medical condition of interest based on that predictive subset of sensor glucose measurement variables and medical record variables. For example, a risk prediction model for cardiovascular disease may calculate the probability of a patient developing cardiovascular disease in the future based on the patient's mean sensor glucose measurement value, sensor glucose measurement standard deviation, the percentage of time the patient's sensor glucose measurement value is outside of a target range, patient age, and whether or not the patient is on insulin therapy. Depending on the embodiment, a risk prediction model could calculate a risk probability within a limited future prediction horizon (e.g., within the next 18 months, within the patient's life expectancy, and/or the like) or for an unlimited or unbounded duration of time. After determining risk prediction models for various medical conditions and/or patient populations, the server 102 may store or otherwise maintain the risk prediction models for the different medical conditions in the database 104 in association with the patient population demographic criteria for the respective model. In other embodiments, the server 102 may transmit or push the risk prediction models to one or more client electronic devices 106, 602. In this regard, in some embodiments, the server 102 may periodically update the risk prediction models (e.g., weekly, monthly, yearly, and/or the like) to reflect new or more recent data in the database 104.

Still referring to FIG. 17, the illustrated risk management process 1700 receives or otherwise obtains measurement data and medical records data for an individual patient and applies one or more risk prediction models to the patient's measurement data and medical records data to determine the patient's individual risk of experiencing the condition(s) associated with the respective risk prediction model(s) (tasks 1708, 1710, 1712). In this regard, an individual patient's sensor glucose measurement data and electronics medical records data may be periodically or continually analyzed using the risk prediction models to ascertain whether the patient's risk of a particular medical condition is above a threshold risk tolerance. In one or more exemplary embodiments, an individual patient's risk for particular conditions is analyzed or otherwise determined at a client device 106, 602 associated with the patient. In this regard, the client device 106, 602 may download or otherwise retrieve, from the database 104 via the server 102, risk prediction models for conditions that its associated patient does not have or has not been diagnosed. The demographic information and medical records data associated with the patient may be utilized to identify which patient population(s) the patient belongs to and then select risk prediction models associated with the identifier patient population(s) for the medical conditions that do not have diagnosis codes present in the patient's medical records data.

After obtaining a risk prediction model for a particular medical condition, the client device 106, 602 utilizes the current or recent sensor glucose measurement data associated with the patient to calculate or otherwise determine one or more inputs to the risk prediction model. Additionally, the client device 106, 602 may download or otherwise retrieve, from the database 104 via the server 102, the field(s) of the patient's medical records data that are also utilized as inputs to the risk prediction model. The client device 106, 602 then utilizes the equation, formula, or function associated with the risk prediction model to calculate or otherwise determine, based on the patient's recent measurement data and medical record fields, an output value representing the patient's probability of developing or experiencing the medical condition associated with the risk prediction model, that is, the patient's risk score for that condition. Additionally, in embodiments where the risk prediction model utilizes contextual information as an input, the client device 106, 602 may obtain the current operating context via one or more sensing arrangements 650, 660 at the client device 106, 602 and input the current operating context to the risk prediction model.

In exemplary embodiments, when the patient's risk score is greater than a notification threshold, the risk management process 1700 generates or otherwise provides a user notification that indicates the potential risk to the patient (tasks 1714, 1716). For example, a user notification may be generated or otherwise provided at the client device 106, 602 that identifies the medical condition that the patient may be at risk of experiencing or exhibiting. In some embodiments, the risk management process 1700 generates or otherwise provides a therapy recommendation based on the medical condition. In this regard, the patient's measurement data and/or medical records data input to the risk prediction model may be analyzed to identify or otherwise determine whether any of the input variables are capable of being modified to decrease the patient's risk score and provide recommended remedial actions to the patient. For example, a GUI display may be generated at the client device 106, 602 that includes recommended actions that the patient could take (e.g., exercise, dietary changes, etc.) to lower his or her mean sensor glucose measurement value when a higher sensor glucose measurement value is predictive of a particular medical condition. As another example, a GUI display at the client device 106, 602 may include recommended therapy changes (e.g., changing therapy types, adding a new medication, and/or the like). In this regard, the risk management process 1700 may initiate the process 1800 described below to identify which therapy modifications should be recommended to the patient to achieve a desired reduction in the patient's risk score.

Still referring to FIG. 17, in one or more exemplary embodiments, the risk management process 1700 adjusts or modifies delivery of fluid by an infusion device based at least in part on the patient's risk score for a particular medical condition (task 1718). In this regard, based on the magnitude of the patient's risk score(s) and/or the medical condition(s), the command generation application 710 may adjust one or more delivery commands to compensate for the patient's risk. For example, when the patient's risk score indicates that the patient's risk of a severe hypoglycemic event is greater than a threshold probability, the command generation application 710 may decrease delivery commands to mitigate the risk of a hypoglycemic event. Thus, even though the patient's current sensor glucose measurement value or predicted glucose levels based on preceding measurement values or trends are above a hypoglycemic threshold or otherwise expected to remain within a target range of glucose values, the command generation application 710 may decrease insulin delivery (e.g., by scaling down or decreasing delivery commands, increasing the patient's target glucose level, increasing the patient's insulin sensitivity factor, and/or the like) to proactively account for a heightened risk of hypoglycemia. As another example, when the patient's risk score indicates that the patient's risk of diabetic ketoacidosis or another acute hyperglycemic event is greater than a threshold probability, the command generation application 710 may increase delivery commands, decrease the patient's insulin sensitivity factor, and/or decrease the patient's target glucose value to mitigate the risk by increasing the patient's insulin on board. Thus, even though the patient's current sensor glucose measurement value or predicted glucose levels are below a hyperglycemic threshold or otherwise expected to remain within a target range of glucose values, the command generation application 710 may increase insulin delivery to proactively decrease the patient's risk of a hyperglycemic event. In some embodiments, the risk management process 1700 may dynamically determine risk scores in real-time in response to new or updated sensor glucose measurement values and cease modifying delivery commands once the patient's risk for a particular condition falls below a threshold value.

Figure 18:
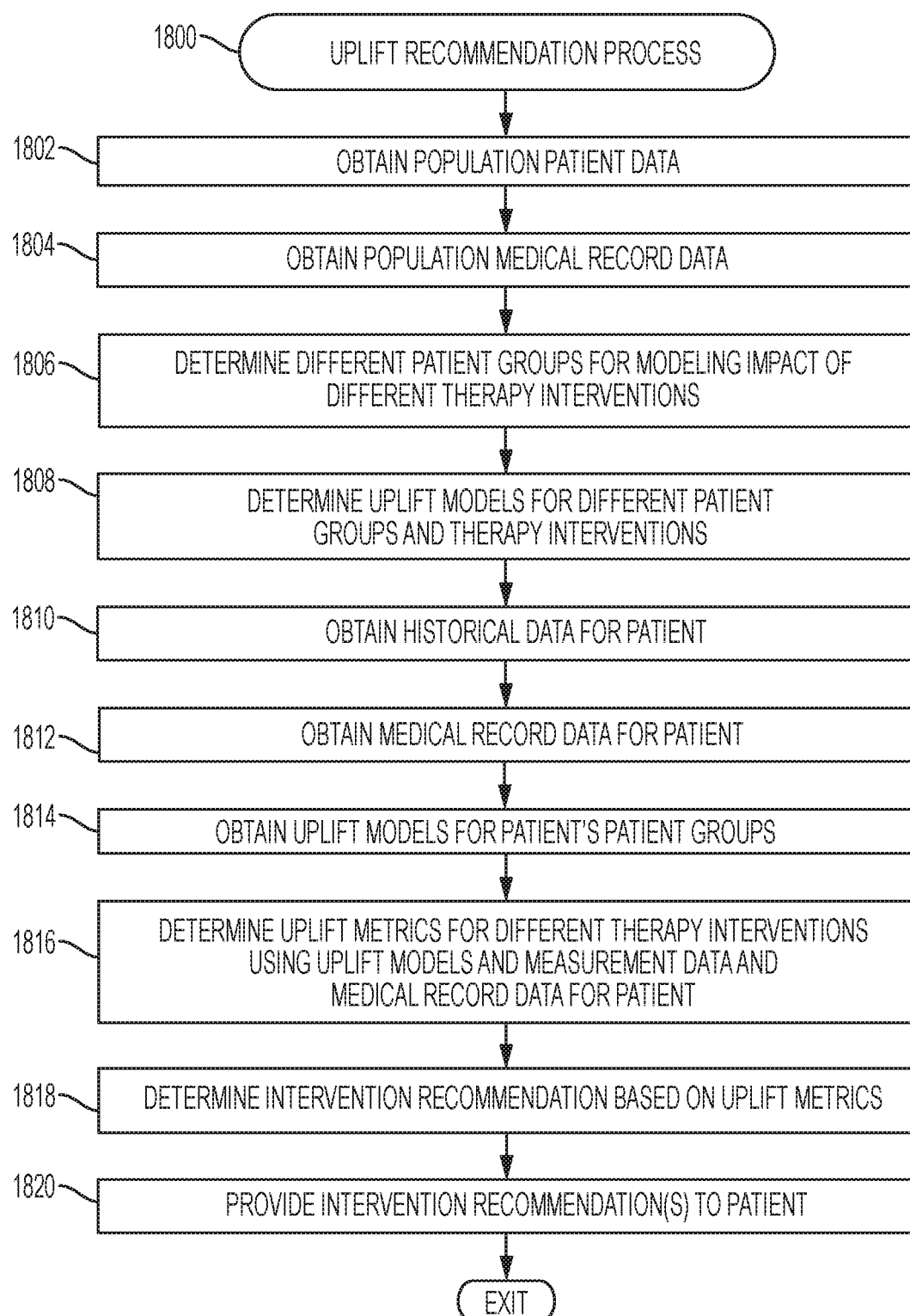
FIG. 18 is a flow diagram of an exemplary uplift recommendation process suitable implementation in connection with a patient data management system in one or more exemplary embodiments.

Referring now to FIG. 18, in one or more exemplary embodiments, an uplift recommendation process 1800 is performed to identify a therapy recommendation that is likely to provide the most beneficial impact on a patient's physiological condition based on that patient's historical data (e.g., measurement data, event log data, contextual data, and/or the like) and medical records data. In some embodiments, the uplift recommendation process 1800 may identify what therapy change or intervention is likely to have the largest impact on an aspect of an individual's physiological condition. In other embodiments, a cost-benefit analysis or similar optimization technique is applied using an uplift metric in conjunction with cost, adherence, patient burden, and/or other metrics to identify an optimal therapy recommendation for the patient. It should be noted that although the terminology uplift, uplift modeling, and variants thereof may be utilized for purposes of explanation, the subject matter is not limited to uplift modeling. Thus, absent clear indication otherwise, uplift modeling should be understood as encompassing any sort of incremental modeling of the impact of a particular event or action on a particular outcome, including true lift modeling, net lift modeling, and variants thereof.

The various tasks performed in connection with the uplift recommendation process 1800 may be performed by hardware, firmware, software executed by processing circuitry, or any combination thereof. For illustrative purposes, the following description refers to elements mentioned above in connection with FIGS. 1 and 6-7. In practice, portions of the uplift recommendation process 1800 may be performed by different elements of a patient data management system 100 or an infusion system 600, such as, for example, the server 102, the electronic device(s) 106, an infusion device 602, and/or the pump control system 620, 700. It should be appreciated that the uplift recommendation process 1800 may include any number of additional or alternative tasks, the tasks need not be performed in the illustrated order and/or the tasks may be performed concurrently, and/or the uplift recommendation process 1800 may be incorporated into a more comprehensive procedure or process having additional functionality not described in detail herein. Moreover, one or more of the tasks shown and described in the context of FIG. 18 could be omitted from a practical embodiment of the uplift recommendation process 1800 as long as the intended overall functionality remains intact.

The uplift recommendation process 1800 receives or otherwise obtains historical patient data and medical records data for a patient population, and then analyzes the relationships between the historical patient data and the medical records data to identify different patient groups for modeling the impact on the patients' physiological condition for different therapy interventions (tasks 1802, 1804, 1806). For example, the server 102 may retrieve historical patient data 120 and electronic medical records data 122 from the database 104 and then utilize machine learning to identify cohorts of patients where different therapy interventions or changes have a statistically significant improvement to an aspect of the physiological patients within that patient cohort, such as, for example, a reduction in A1C laboratory values, a reduction in glucose excursion events, an increase in the percentage of time sensor glucose measurements are within a target range, and/or the like. In this regard, the patient cohorts may be defined by common demographic attributes (e.g., gender, income, and/or the like), common medical diagnoses, common therapy regimens or therapy types (e.g., monotherapy patients, dual therapy patients, etc.), common medications or prescriptions, and/or other medical records commonalities. For example, in addition to defining patient cohorts demographically (e.g., by age, location, race, gender, socioeconomic status, profession, etc.), patient cohorts may be characterized or defined utilizing clustering techniques to classify similar patients using other available data sets, such as, for example, mood logs, program interactions, personal goals, and/or the like, which, for example, may be tracked, monitored or logged by an application at a client device 106.

After identifying different patient groups for modeling for different therapy interventions, the uplift recommendation process 1800 determines an uplift model for calculating an impact of the respective therapy intervention on the respective patient group (task 1808). In this regard, the server 102 identifies the sensor glucose measurement variables, medical record variables, and/or operating context variables that are correlative to or predictive of the improvement in the physiological condition and then calculates or otherwise determines an equation, function, or model for calculating the likely improvement in the physiological condition based on the identified subset of variables. For example, stepwise feature selection may be performed to identify which fields or attributes of patient measurement data and medical records data are most correlative to or predictive of the amount of A1C reduction within the patient cohort. An uplift model for calculating the estimated A1C reduction for patients within that particular patient cohort may then be determined as a function of the correlative subset of sensor glucose measurement variables, medical record variables, and/or operating context variables. In this regard, for each of the different patient cohorts identified for different potential therapy interventions, the server 102 may determine an uplift model for calculating a metric indicative of the impact of the respective therapy intervention on the respective cohort patients' physiological condition as a function of a subset of sensor glucose measurement variables, medical record variables, and/or operating context variables. The uplift models determined by the server 102 may be stored or otherwise maintained in the database 104 in association with the respective combination of patient cohort attributes and therapy intervention. In some embodiments, the server 102 may push or otherwise transmit to uplift models to client devices 106, 602 associated with patients classified within the respective patient cohorts. It should be noted that the uplift modeling is not limited to stepwise feature selection, and in other embodiments, random forests analysis, logistic regression, and/or other machine learning or artificial intelligence techniques may be utilized to generate an uplift model.

Still referring to FIG. 18, to determine a therapy recommendation for an individual patient, the uplift recommendation process 1800 receives or otherwise obtains the historical observational patient data and medical records data for an individual patient and then identifies or otherwise obtains the uplift models associated with patient groups that include the patient or that the patient would otherwise be classified into based on the patient's demographic information, medical records, and/or the like (tasks 1810, 1812, 1814). In other words, the patient's medical records, measurement data, event log data, and/or current operating context may be utilized to identify which uplift models in the database 104 are likely to be most relevant to the individual patient being analyzed. Thereafter, the uplift recommendation process 1800 calculates or otherwise determines the impact or uplift metric associated with each respective therapy intervention for the patient based on the patient's measurement data and medical records data and the respective uplift models associated with the different therapy interventions (task 1816). In this regard, for each potential therapy intervention, the uplift recommendation process 1800 may calculate or otherwise determine an estimated A1C reduction or other estimation of the uplift or impact associated with the respective therapy intervention on the patient based on the patient's medical records, measurement data, and/or current operating context.

After determining uplift metrics for different potential therapy interventions for the patient, the uplift recommendation process 1800 determines a therapy intervention recommendation based on the uplift metrics and generating or otherwise providing indication of the recommended therapy intervention to the patient (tasks 1818, 1820). For example, in one embodiment, the uplift recommendation process 1800 identifies the therapy intervention having the maximum estimated impact or benefit (e.g., the largest estimated A1C reduction) as the recommended therapy intervention for the patient. In other embodiments, the uplift recommendation process 1800 performs a cost-benefit analysis or other optimization to identify an optimal therapy intervention based on the estimated uplift values associated with the different potential therapy interventions and the costs associated with the respective potential therapy interventions. For example, the uplift recommendation process 1800 identifies the therapy intervention having the highest ratio of estimated uplift value to cost as the recommended therapy intervention. In this regard, in some embodiments, the claims data 124 maintained in the database 104 may be utilized to calculate or otherwise determine an estimated cost associated with a particular therapy intervention, which, in turn, may be utilized to determine the relative impact or benefit of that therapy intervention (e.g., by dividing the uplift value by the estimated cost).

In one or more embodiments, the uplift recommendation process 1800 identifies or otherwise determines an optimal therapy intervention based on the estimated uplift values associated with the different potential therapy interventions, the costs associated with the different potential therapy interventions, and estimated adherence metric values associated with the different potential therapy interventions. In this regard, some embodiments of the uplift recommendation process 1800 may calculate or otherwise determine an adherence metric value representative of how likely the patient is to adhere to the particular therapy intervention, as described in greater detail below in the context of the adherence recommendation process 1900 of FIG. 19. Thus, in some embodiments, the uplift recommendation process 1800 may identify, for recommendation as the optimal therapy intervention, a therapy intervention that does not have the highest estimated uplift value but has a relatively lower cost and/or higher adherence than one or more therapy interventions having the higher estimated uplift values. Thus, the patient may be apprised of the therapy intervention that is most cost effective and more likely to be successful based on the patient's likelihood of adherence to the recommended therapy.

Figure 19:
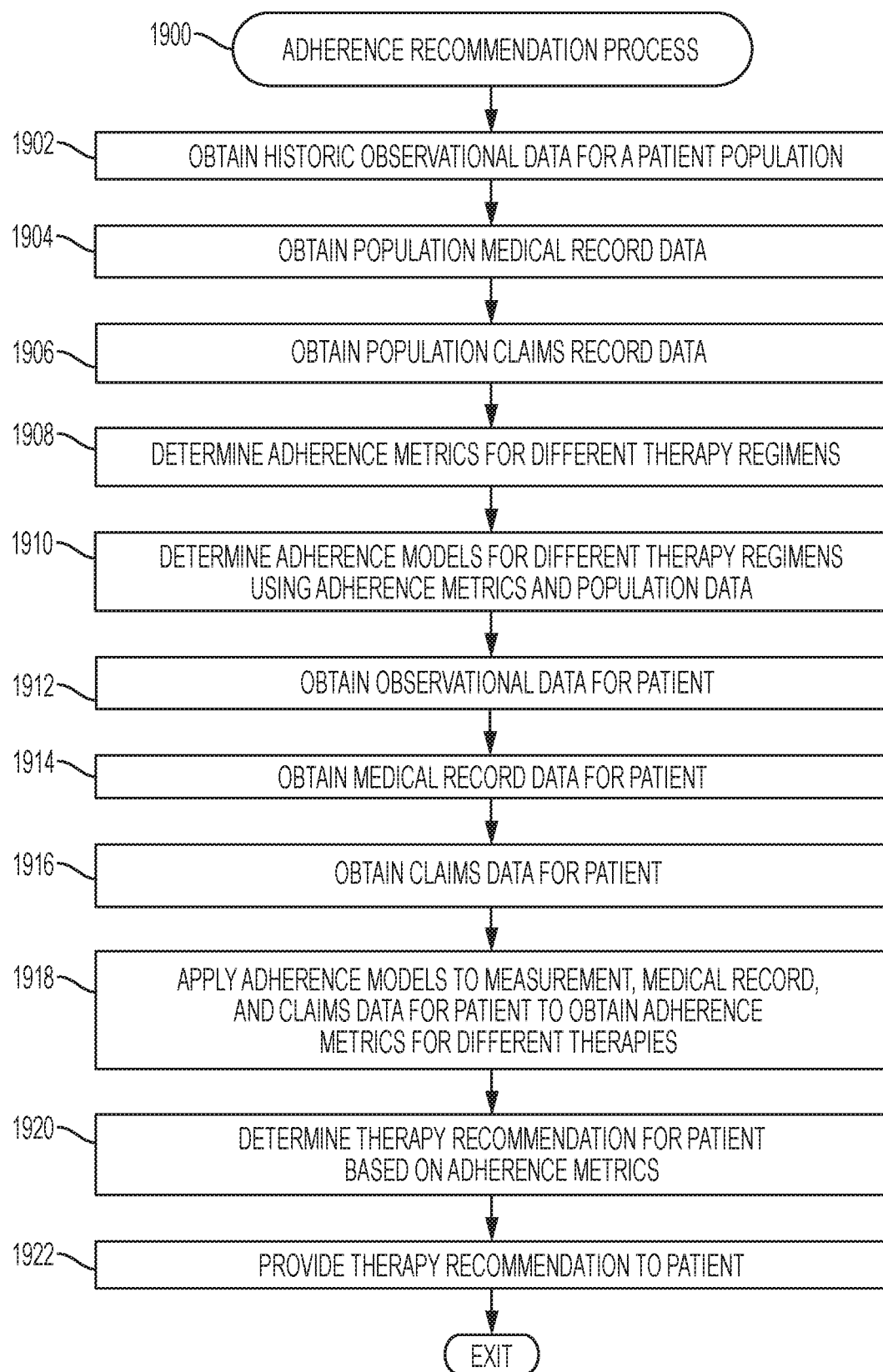
FIG. 19 is a flow diagram of an exemplary adherence recommendation process suitable implementation in connection with a patient data management system in one or more exemplary embodiments.

Referring now to FIG. 19, in one or more exemplary embodiments, an adherence recommendation process 1900 may be performed to identify a therapy recommendation that an individual patient is most likely to adhere to or will otherwise yield the highest adherence. In this regard, in exemplary embodiments described herein, adherence modeling is utilized to determine adherence metrics that represent the respective probabilities that a patient with adhere to a particular therapy regimen, for example, by taking a fully prescribed therapy regimen or engaging in some other action as prescribed by the respective therapy regimen or indicative of an attempt to fulfill the respective therapy regimen (e.g., filling a prescription within a threshold amount of time after being written). Using the adherence metrics, a therapy intervention that is likely to have better adherence by the patient (and thereby, more likely to have a beneficial outcome relative to prescribing a therapy regimen that is unlikely to have that level of adherence) may be recommended to the patient. For example, for a given patient, if the adherence metric value associated with an injectable insulin regimen (e.g., 15%) is lower relative to the adherence metric for an oral medication such as GLP-2 or Sulfonylurea (e.g., 50%), the oral medication may be recommended since it may be likely to provide greater uplift when its associated adherence probability is accounted for.

The various tasks performed in connection with the adherence recommendation process 1900 may be performed by hardware, firmware, software executed by processing circuitry, or any combination thereof. For illustrative purposes, the following description refers to elements mentioned above in connection with FIGS. 1 and 6-7. In practice, portions of the adherence recommendation process 1900 may be performed by different elements of a patient data management system 100 or an infusion system 600, such as, for example, the server 102, the electronic device(s) 106, an infusion device 602, and/or the pump control system 620, 700. It should be appreciated that the adherence recommendation process 1900 may include any number of additional or alternative tasks, the tasks need not be performed in the illustrated order and/or the tasks may be performed concurrently, and/or the adherence recommendation process 1900 may be incorporated into a more comprehensive procedure or process having additional functionality not described in detail herein. Moreover, one or more of the tasks shown and described in the context of FIG. 19 could be omitted from a practical embodiment of the adherence recommendation process 1900 as long as the intended overall functionality remains intact.

The adherence recommendation process 1900 receives or otherwise obtains historical observational data, medical records data, and medical claims data for a patient population from a database (tasks 1902, 1904, 1906). The adherence recommendation process 1900 calculates or otherwise determines adherence metrics for different therapy interventions or regimens based on the relationships between the historical observational data, medical records data, and medical claims data for a patient population (task 1908). For example, for each patient having his or her corresponding medical records and medical claims data stored in the database 104, the server 102 may analyze the relationship between the patient's prescriptions and other therapy information from the patient's medical records data and the number and/or frequency of the patient's medical claims corresponding to those prescriptions or therapies in the patient's claims data to determine an adherence metric for that respective therapy associated with the patient based on how well the patient's claims data adheres to or aligns with the patient's prescribed therapy. In this regard, patients having claims data indicating that prescriptions are being filled with the prescribed frequency or with relatively little delay after the prescriptions are written may be assigned relatively high adherence values, while patients whose claims data indicate prescriptions are not being filled regularly or promptly may be assigned relatively low adherence values. Additionally, in some embodiments, the event log data or other observational patient data may also be utilized when determining adherence metrics. For example, the patient's event log data may indicate when the patient takes a prescribed medicine and the corresponding dosage, which, in turn may be compared to the prescription information from the patient's medical records data to determine how well the patient's behavior adheres to the patient's prescribed therapy.

In the illustrated embodiment, after determining adherence metrics associated with different therapies for different patients, the adherence recommendation process 1900 continues by analyzing the relationships between the observational patient data, the medical records, the claims data, and the adherence values to determine adherence models for calculating an adherence metric for different therapies based on an individual patient's observational data, medical records data, and claims data (task 1910). In this regard, for a subset of patients having a particular therapy regimen in common, the server 102 identifies the observational patient variables (e.g., sensor glucose measurement variables, meals, exercise, or other event log variables, operating context variables and/or the like), medical record variables (e.g., demographic information, medical conditions, and/or claims data variables (e.g., refill data for previous prescriptions, and/or the like) that are correlative to or predictive of the patients' adherence metric values for that therapy regimen, and then calculates or otherwise determines an equation, function, or model for calculating the likely adherence metric value for a given patient based on the identified subset of variables associated with that prospective patient. For example, stepwise feature selection or other machine learning techniques may be performed to identify which fields or attributes of the historical observational patient data 120 and medical records data 122 are most correlative to or predictive of the adherence metric value among patients prescribed a respective therapy regimen. An adherence model for calculating the estimated adherence for patients not currently on that therapy regimen may then be determined as a function of the correlative subset of variables. In this regard, for each of the different potential therapy regimens or interventions, the server 102 may determine an adherence model for calculating a metric indicative of the likely adherence to the respective therapy regimen based on existing patients that are or were prescribed that respective therapy regimen. The adherence models determined by the server 102 may be stored or otherwise maintained in the database 104 in association with the respective therapy regimens or interventions or pushed or otherwise transmitted to client devices 106, 602.

Still referring to FIG. 19, to determine a therapy recommendation for an individual patient, the adherence recommendation process 1900 receives or otherwise obtains observational data, medical records data, and claims data for an individual patient and then applies the various adherence models for different therapy regimen that are not currently prescribed to the patient to calculate or otherwise determine adherence metrics for the different therapy regimens (tasks 1912, 1914). In this regard, the server 102 or client device 106, 602 obtains data associated with a patient of interest from the database 104 along with recent measurement data and/or operational context information from a client device 106, 602 associated with the patient, and then utilizes the adherence models to estimate that patient's likely adherence for each of the different potential therapy regimen that are not currently prescribed for the patient.

In exemplary embodiments, the adherence recommendation process 1900 determines a therapy recommendation for the patient based on the adherence metric values associated with the different potential therapy regimen and generates or otherwise provides indication of the therapy recommendation to the patient or another user (e.g., a physician, a healthcare provider, and/or the like) (tasks 1916, 1918). In some embodiments, the adherence recommendation process 1900 selects or otherwise identifies the therapy regimen having the highest adherence metric value as the recommended therapy for the patient. In other embodiments, the adherence metric values associated with the different potential therapy regimens are considered in conjunction with uplift metric values and/or estimated costs associated with the different potential therapy regimens to identify an optimal therapy regimen, as described above in the context of FIG. 19. For example, in embodiments where the adherence metric value represents a probability or percentage, the uplift metric value associated with a potential therapy regimen for a patient of interest may be scaled or otherwise multiplied by the adherence metric value associated with that therapy regimen for that patient of interest to obtain a probable uplift value for the patient that represents the likely benefit once adherence is accounted for. In one embodiment, the recommended therapy may be selected as the therapy regimen having the highest ratio of probable uplift value to cost (e.g., the product of the uplift metric value and adherence probability divided by estimated cost). A GUI display may be generated or otherwise provided at the client device 106, 602 that indicates the recommended therapy to the patient or other user of the client device 106, 602. In one embodiment, the GUI display may include a list of potential therapies that are sorted, prioritize, or otherwise ordered in a manner that is influenced by the adherence metric values, such that the most highly prioritized therapy corresponds to the therapy regimen recommended based on the adherence metric.

Referring to FIGS. 17-19, it should be noted that in some embodiments, the processes 1700, 1800, 1900 may be implemented in connection with the patient data management system 100 of FIG. 1 and adapted to leverage the graph data structures in the database 104 to improve the accuracy of the modeling. In this regard, weighted directional or causal links between nodes or entities may be utilized to identify predictive relationships and corresponding influences on patient outcomes for improved modeling. Additionally, shared links within or across logical database layers may be utilized to identify commonalities between patients that may not otherwise be readily identifiable using conventional databases reliant on tables that lack causal and/or probabilistic relationships between entities.

Infusion System Integration

Figure 20:
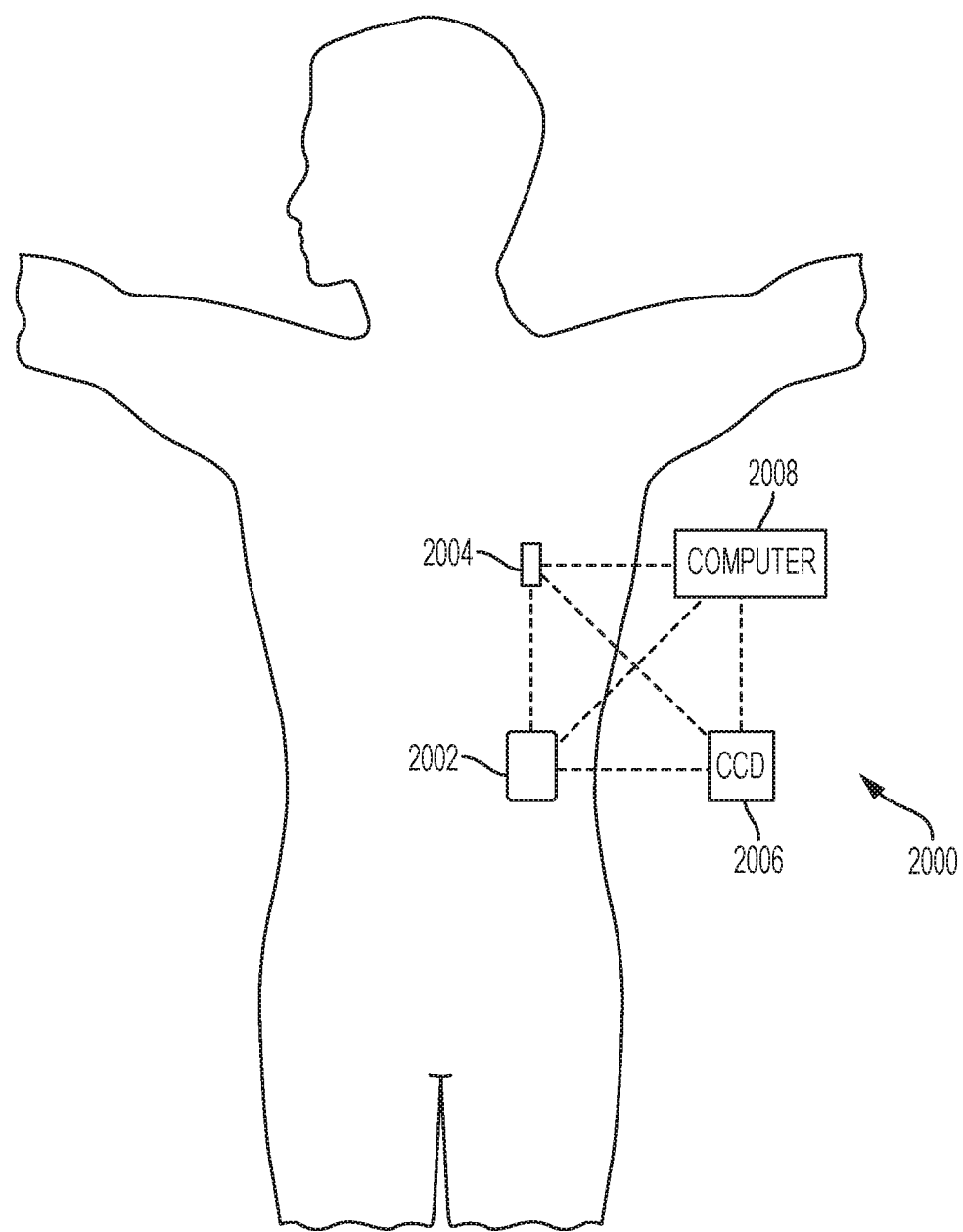
FIG. 20 depicts an exemplary embodiment of an infusion system

FIG. 20 depicts one exemplary embodiment of an infusion system 2000 suitable for use with the subject matter described above. For example, a computer 2008 (e.g., computing device 102) may communicate with and/or obtain data from various client electronic devices (e.g., electronic devices 106), such as a fluid infusion device (or infusion pump) 2002 (e.g., infusion device 602), a sensing arrangement 2004 (e.g., glucose sensing arrangement 604), and a command control device (CCD) 2006. The components of an infusion system 2000 may be realized using different platforms, designs, and configurations, and the embodiment shown in FIG. 20 is not exhaustive or limiting. In practice, the infusion device 2002 and the sensing arrangement 2004 are secured at desired locations on the body of a user (or patient), as illustrated in FIG. 20. In this regard, the locations at which the infusion device 2002 and the sensing arrangement 2004 are secured to the body of the user in FIG. 20 are provided only as a representative, non-limiting, example. The elements of the infusion system 2000 may be similar to those described in U.S. Pat. No. 8,674,288, the subject matter of which is hereby incorporated by reference in its entirety.

In the illustrated embodiment of FIG. 20, the infusion device 2002 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 2004 generally represents the components of the infusion system 2000 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 2004 may include electronics and enzymes reactive to a biological condition, such as a blood glucose level, or the like, of the user, and provide data indicative of the blood glucose level to the infusion device 2002, the CCD 2006 and/or the computer 2008. For example, the infusion device 2002, the CCD 2006 and/or the computer 2008 may include a display for presenting information or data to the user based on the sensor data received from the sensing arrangement 2004, such as, for example, a current glucose level of the user, a graph or chart of the user's glucose level versus time, device status indicators, alert messages, or the like. In other embodiments, the infusion device 2002, the CCD 2006 and/or the computer 2008 may include electronics and software that are configured to analyze sensor data and operate the infusion device 2002 to deliver fluid to the body of the user based on the sensor data and/or preprogrammed delivery routines. Thus, in exemplary embodiments, one or more of the infusion device 2002, the sensing arrangement 2004, the CCD 2006, and/or the computer 2008 includes a transmitter, a receiver, and/or other transceiver electronics that allow for communication with other components of the infusion system 2000, so that the sensing arrangement 2004 may transmit sensor data or monitor data to one or more of the infusion device 2002, the CCD 2006 and/or the computer 2008.

Still referring to FIG. 20, in various embodiments, the sensing arrangement 2004 may be secured to the body of the user or embedded in the body of the user at a location that is remote from the location at which the infusion device 2002 is secured to the body of the user. In various other embodiments, the sensing arrangement 2004 may be incorporated within the infusion device 2002. In other embodiments, the sensing arrangement 2004 may be separate and apart from the infusion device 2002, and may be, for example, part of the CCD 2006. In such embodiments, the sensing arrangement 2004 may be configured to receive a biological sample, analyte, or the like, to measure a condition of the user.

In some embodiments, the CCD 2006 and/or the computer 2008 may include electronics and other components configured to perform processing, delivery routine storage, and to control the infusion device 2002 in a manner that is influenced by sensor data measured by and/or received from the sensing arrangement 2004. By including control functions in the CCD 2006 and/or the computer 2008, the infusion device 2002 may be made with more simplified electronics. However, in other embodiments, the infusion device 2002 may include all control functions, and may operate without the CCD 2006 and/or the computer 2008. In various embodiments, the CCD 2006 may be a portable electronic device. In addition, in various embodiments, the infusion device 2002 and/or the sensing arrangement 2004 may be configured to transmit data to the CCD 2006 and/or the computer 2008 for display or processing of the data by the CCD 2006 and/or the computer 2008.

In some embodiments, the CCD 2006 and/or the computer 2008 may provide information to the user that facilitates the user's subsequent use of the infusion device 2002. For example, the CCD 2006 may provide information to the user to allow the user to determine the rate or dose of medication to be administered into the user's body. In other embodiments, the CCD 2006 may provide information to the infusion device 2002 to autonomously control the rate or dose of medication administered into the body of the user. In some embodiments, the sensing arrangement 2004 may be integrated into the CCD 2006. Such embodiments may allow the user to monitor a condition by providing, for example, a sample of his or her blood to the sensing arrangement 2004 to assess his or her condition. In some embodiments, the sensing arrangement 2004 and the CCD 2006 may be used for determining glucose levels in the blood and/or body fluids of the user without the use of, or necessity of, a wire or cable connection between the infusion device 2002 and the sensing arrangement 2004 and/or the CCD 2006.

In some embodiments, the sensing arrangement 2004 and/or the infusion device 2002 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 2004 is configured to sense or measure a condition of the user, such as, blood glucose level or the like. The infusion device 2002 is configured to deliver fluid in response to the condition sensed by the sensing arrangement 2004. In turn, the sensing arrangement 2004 continues to sense or otherwise quantify a current condition of the user, thereby allowing the infusion device 2002 to deliver fluid continuously in response to the condition currently (or most recently) sensed by the sensing arrangement 2004 indefinitely. In some embodiments, the sensing arrangement 2004 and/or the infusion device 2002 may be configured to utilize the closed-loop system only for a portion of the day, for example only when the user is asleep or awake.

Figure 21:
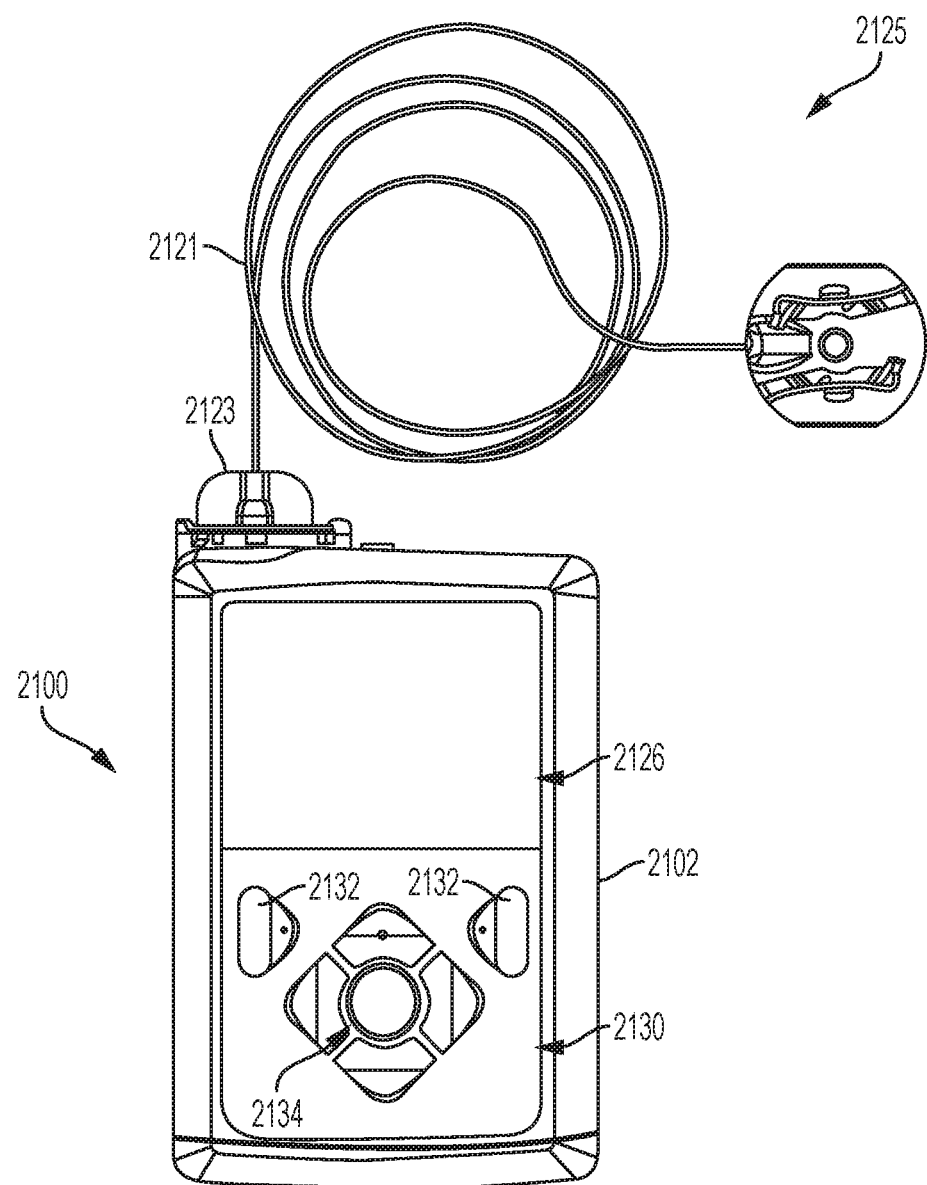
FIG. 21 depicts a plan view of an exemplary embodiment of a fluid infusion device suitable for use in the infusion system of FIG. 20.
Figure 22:
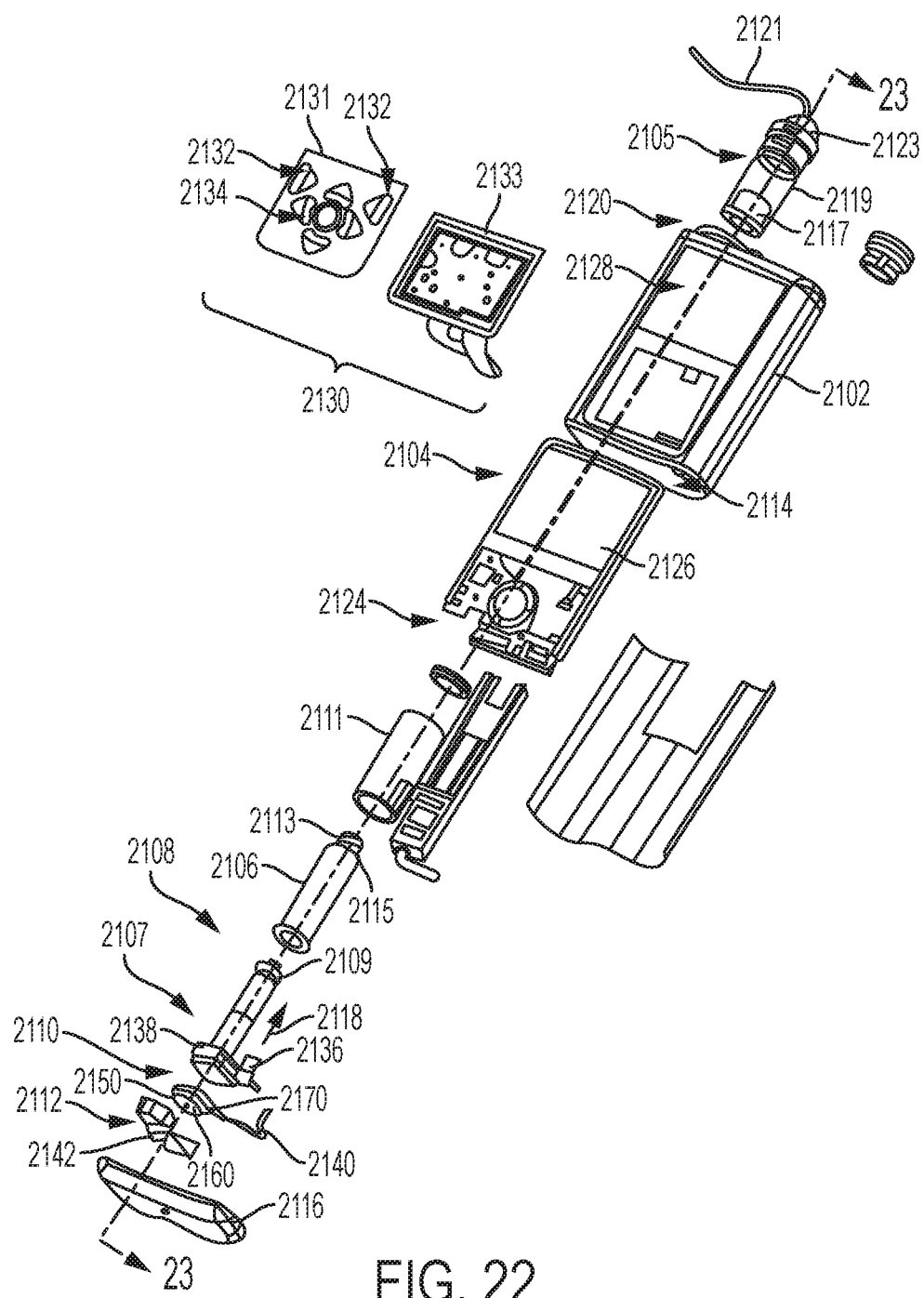
FIG. 22 is an exploded perspective view of the fluid infusion device of FIG. 21.
Figure 23:
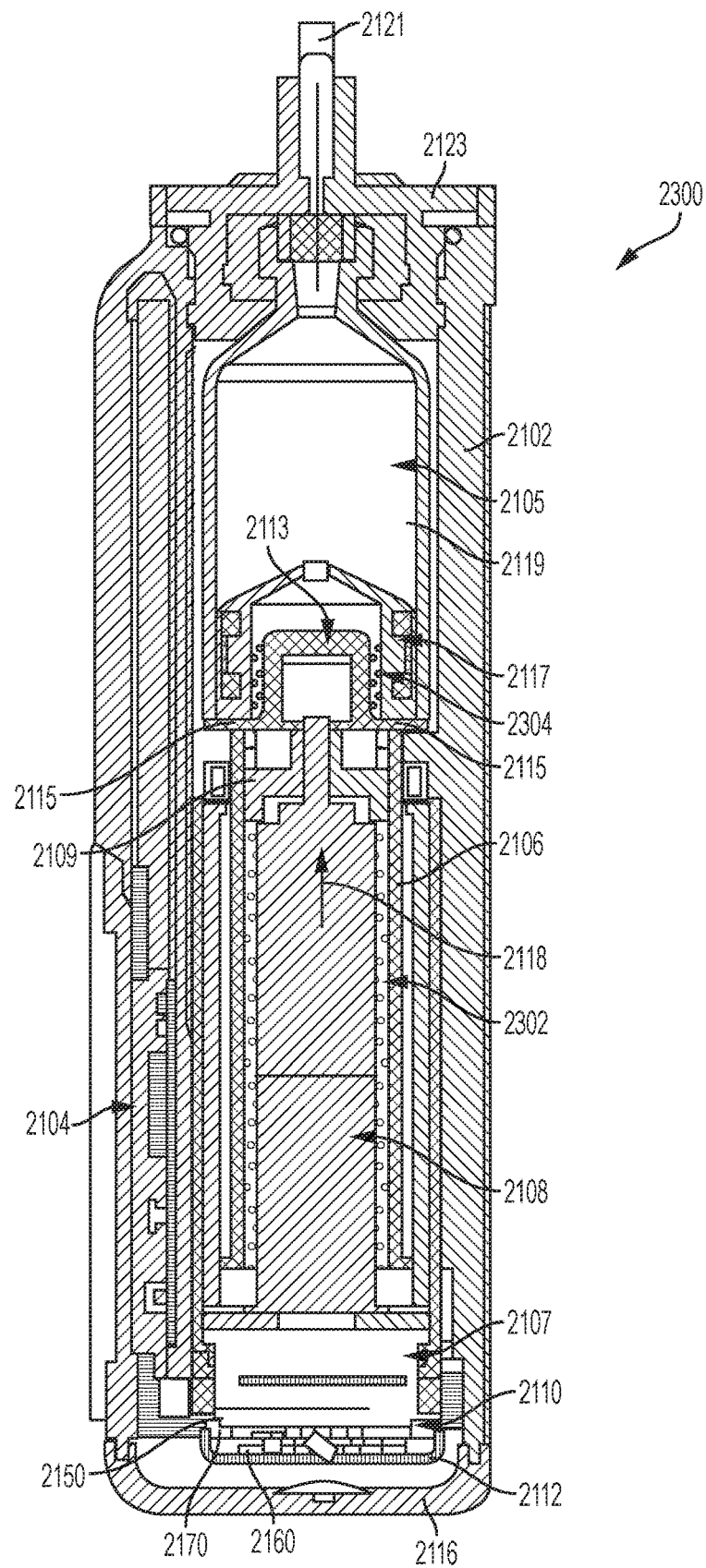
FIG. 23 is a cross-sectional view of the fluid infusion device of FIGS. 21-22 as viewed along line 23-23 in FIG. 22 when assembled with a reservoir inserted in the infusion device.

FIGS. 21-23 depict one exemplary embodiment of a fluid infusion device 2100 (or alternatively, infusion pump) suitable for use in an infusion system, such as, for example, as infusion device 602 in the infusion system 600 of FIG. 6 or as infusion device 2002 in the infusion system 2000 of FIG. 20. The fluid infusion device 2100 is a portable medical device designed to be carried or worn by a patient (or user), and the fluid infusion device 2100 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 21-23 depict some aspects of the infusion device 2100 in a simplified manner; in practice, the infusion device 2100 could include additional elements, features, or components that are not shown or described in detail herein.

As best illustrated in FIGS. 21-22, the illustrated embodiment of the fluid infusion device 2100 includes a housing 2102 adapted to receive a fluid-containing reservoir 2105. An opening 2120 in the housing 2102 accommodates a fitting 2123 (or cap) for the reservoir 2105, with the fitting 2123 being configured to mate or otherwise interface with tubing 2121 of an infusion set 2125 that provides a fluid path to/from the body of the user. In this manner, fluid communication from the interior of the reservoir 2105 to the user is established via the tubing 2121. The illustrated fluid infusion device 2100 includes a human-machine interface (HMI) 2130 (or user interface) that includes elements 2132, 2134 that can be manipulated by the user to administer a bolus of fluid (e.g., insulin), to change therapy settings, to change user preferences, to select display features, and the like. The infusion device also includes a display element 2126, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 2102 is formed from a substantially rigid material having a hollow interior 2114 adapted to allow an electronics assembly 2104, a sliding member (or slide) 2106, a drive system 2108, a sensor assembly 2110, and a drive system capping member 2112 to be disposed therein in addition to the reservoir 2105, with the contents of the housing 2102 being enclosed by a housing capping member 2116. The opening 2120, the slide 2106, and the drive system 2108 are coaxially aligned in an axial direction (indicated by arrow 2118), whereby the drive system 2108 facilitates linear displacement of the slide 2106 in the axial direction 2118 to dispense fluid from the reservoir 2105 (after the reservoir 2105 has been inserted into opening 2120), with the sensor assembly 2110 being configured to measure axial forces (e.g., forces aligned with the axial direction 2118) exerted on the sensor assembly 2110 responsive to operating the drive system 2108 to displace the slide 2106. In various embodiments, the sensor assembly 2110 may be utilized to detect one or more of the following: an occlusion in a fluid path that slows, prevents, or otherwise degrades fluid delivery from the reservoir 2105 to a user's body; when the reservoir 2105 is empty; when the slide 2106 is properly seated with the reservoir 2105; when a fluid dose has been delivered; when the infusion pump 2100 is subjected to shock or vibration; when the infusion pump 2100 requires maintenance.

Depending on the embodiment, the fluid-containing reservoir 2105 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 22-23, the reservoir 2105 typically includes a reservoir barrel 2119 that contains the fluid and is concentrically and/or coaxially aligned with the slide 2106 (e.g., in the axial direction 2118) when the reservoir 2105 is inserted into the infusion pump 2100. The end of the reservoir 2105 proximate the opening 2120 may include or otherwise mate with the fitting 2123, which secures the reservoir 2105 in the housing 2102 and prevents displacement of the reservoir 2105 in the axial direction 2118 with respect to the housing 2102 after the reservoir 2105 is inserted into the housing 2102. As described above, the fitting 2123 extends from (or through) the opening 2120 of the housing 2102 and mates with tubing 2121 to establish fluid communication from the interior of the reservoir 2105 (e.g., reservoir barrel 2119) to the user via the tubing 2121 and infusion set 2125. The opposing end of the reservoir 2105 proximate the slide 2106 includes a plunger 2117 (or stopper) positioned to push fluid from inside the barrel 2119 of the reservoir 2105 along a fluid path through tubing 2121 to a user. The slide 2106 is configured to mechanically couple or otherwise engage with the plunger 2117, thereby becoming seated with the plunger 2117 and/or reservoir 2105. Fluid is forced from the reservoir 2105 via tubing 2121 as the drive system 2108 is operated to displace the slide 2106 in the axial direction 2118 toward the opening 2120 in the housing 2102.

In the illustrated embodiment of FIGS. 22-23, the drive system 2108 includes a motor assembly 2107 and a drive screw 2109. The motor assembly 2107 includes a motor that is coupled to drive train components of the drive system 2108 that are configured to convert rotational motor motion to a translational displacement of the slide 2106 in the axial direction 2118, and thereby engaging and displacing the plunger 2117 of the reservoir 2105 in the axial direction 2118. In some embodiments, the motor assembly 2107 may also be powered to translate the slide 2106 in the opposing direction (e.g., the direction opposite direction 2118) to retract and/or detach from the reservoir 2105 to allow the reservoir 2105 to be replaced. In exemplary embodiments, the motor assembly 2107 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 2105.

As best shown in FIG. 23, the drive screw 2109 mates with threads 2302 internal to the slide 2106. When the motor assembly 2107 is powered and operated, the drive screw 2109 rotates, and the slide 2106 is forced to translate in the axial direction 2118. In an exemplary embodiment, the infusion pump 2100 includes a sleeve 2111 to prevent the slide 2106 from rotating when the drive screw 2109 of the drive system 2108 rotates. Thus, rotation of the drive screw 2109 causes the slide 2106 to extend or retract relative to the drive motor assembly 2107. When the fluid infusion device is assembled and operational, the slide 2106 contacts the plunger 2117 to engage the reservoir 2105 and control delivery of fluid from the infusion pump 2100. In an exemplary embodiment, the shoulder portion 2115 of the slide 2106 contacts or otherwise engages the plunger 2117 to displace the plunger 2117 in the axial direction 2118. In alternative embodiments, the slide 2106 may include a threaded tip 2113 capable of being detachably engaged with internal threads 2304 on the plunger 2117 of the reservoir 2105, as described in detail in U.S. Pat. Nos. 6,248,093 and 6,485,465, which are incorporated by reference herein.

As illustrated in FIG. 22, the electronics assembly 2104 includes control electronics 2124 coupled to the display element 2126, with the housing 2102 including a transparent window portion 2128 that is aligned with the display element 2126 to allow the display 2126 to be viewed by the user when the electronics assembly 2104 is disposed within the interior 2114 of the housing 2102. The control electronics 2124 generally represent the hardware, firmware, processing logic and/or software (or combinations thereof) configured to control operation of the motor assembly 2107 and/or drive system 2108. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 2124 includes one or more programmable controllers that may be programmed to control operation of the infusion pump 2100.

The motor assembly 2107 includes one or more electrical leads 2136 adapted to be electrically coupled to the electronics assembly 2104 to establish communication between the control electronics 2124 and the motor assembly 2107. In response to command signals from the control electronics 2124 that operate a motor driver (e.g., a power converter) to regulate the amount of power supplied to the motor from a power supply, the motor actuates the drive train components of the drive system 2108 to displace the slide 2106 in the axial direction 2118 to force fluid from the reservoir 2105 along a fluid path (including tubing 2121 and an infusion set), thereby administering doses of the fluid contained in the reservoir 2105 into the user's body. Preferably, the power supply is realized one or more batteries contained within the housing 2102. Alternatively, the power supply may be a solar panel, capacitor, AC or DC power supplied through a power cord, or the like. In some embodiments, the control electronics 2124 may operate the motor of the motor assembly 2107 and/or drive system 2108 in a stepwise manner, typically on an intermittent basis; to administer discrete precise doses of the fluid to the user according to programmed delivery profiles.

Referring to FIGS. 21-23, as described above, the user interface 2130 includes HMI elements, such as buttons 2132 and a directional pad 2134, that are formed on a graphic keypad overlay 2131 that overlies a keypad assembly 2133, which includes features corresponding to the buttons 2132, directional pad 2134 or other user interface items indicated by the graphic keypad overlay 2131. When assembled, the keypad assembly 2133 is coupled to the control electronics 2124, thereby allowing the HMI elements 2132, 2134 to be manipulated by the user to interact with the control electronics 2124 and control operation of the infusion pump 2100, for example, to administer a bolus of insulin, to change therapy settings, to change user preferences, to select display features, to set or disable alarms and reminders, and the like. In this regard, the control electronics 2124 maintains and/or provides information to the display 2126 regarding program parameters, delivery profiles, pump operation, alarms, warnings, statuses, or the like, which may be adjusted using the HMI elements 2132, 2134. In various embodiments, the HMI elements 2132, 2134 may be realized as physical objects (e.g., buttons, knobs, joysticks, and the like) or virtual objects (e.g., using touch-sensing and/or proximity-sensing technologies). For example, in some embodiments, the display 2126 may be realized as a touch screen or touch-sensitive display, and in such embodiments, the features and/or functionality of the HMI elements 2132, 2134 may be integrated into the display 2126 and the HMI 2130 may not be present. In some embodiments, the electronics assembly 2104 may also include alert generating elements coupled to the control electronics 2124 and suitably configured to generate one or more types of feedback, such as, without limitation: audible feedback; visual feedback; haptic (physical) feedback; or the like.

Referring to FIGS. 22-23, in accordance with one or more embodiments, the sensor assembly 2110 includes a back plate structure 2150 and a loading element 2160. The loading element 2160 is disposed between the capping member 2112 and a beam structure 2170 that includes one or more beams having sensing elements disposed thereon that are influenced by compressive force applied to the sensor assembly 2110 that deflects the one or more beams, as described in greater detail in U.S. Pat. No. 8,474,332, which is incorporated by reference herein. In exemplary embodiments, the back plate structure 2150 is affixed, adhered, mounted, or otherwise mechanically coupled to the bottom surface 2138 of the drive system 2108 such that the back plate structure 2150 resides between the bottom surface 2138 of the drive system 2108 and the housing cap 2116. The drive system capping member 2112 is contoured to accommodate and conform to the bottom of the sensor assembly 2110 and the drive system 2108. The drive system capping member 2112 may be affixed to the interior of the housing 2102 to prevent displacement of the sensor assembly 2110 in the direction opposite the direction of force provided by the drive system 2108 (e.g., the direction opposite direction 2118). Thus, the sensor assembly 2110 is positioned between the motor assembly 2107 and secured by the capping member 2112, which prevents displacement of the sensor assembly 2110 in a downward direction opposite the direction of arrow 2118, such that the sensor assembly 2110 is subjected to a reactionary compressive force when the drive system 2108 and/or motor assembly 2107 is operated to displace the slide 2106 in the axial direction 2118 in opposition to the fluid pressure in the reservoir 2105. Under normal operating conditions, the compressive force applied to the sensor assembly 2110 is correlated with the fluid pressure in the reservoir 2105. As shown, electrical leads 2140 are adapted to electrically couple the sensing elements of the sensor assembly 2110 to the electronics assembly 2104 to establish communication to the control electronics 2124, wherein the control electronics 2124 are configured to measure, receive, or otherwise obtain electrical signals from the sensing elements of the sensor assembly 2110 that are indicative of the force applied by the drive system 2108 in the axial direction 2118.

Figure 24:
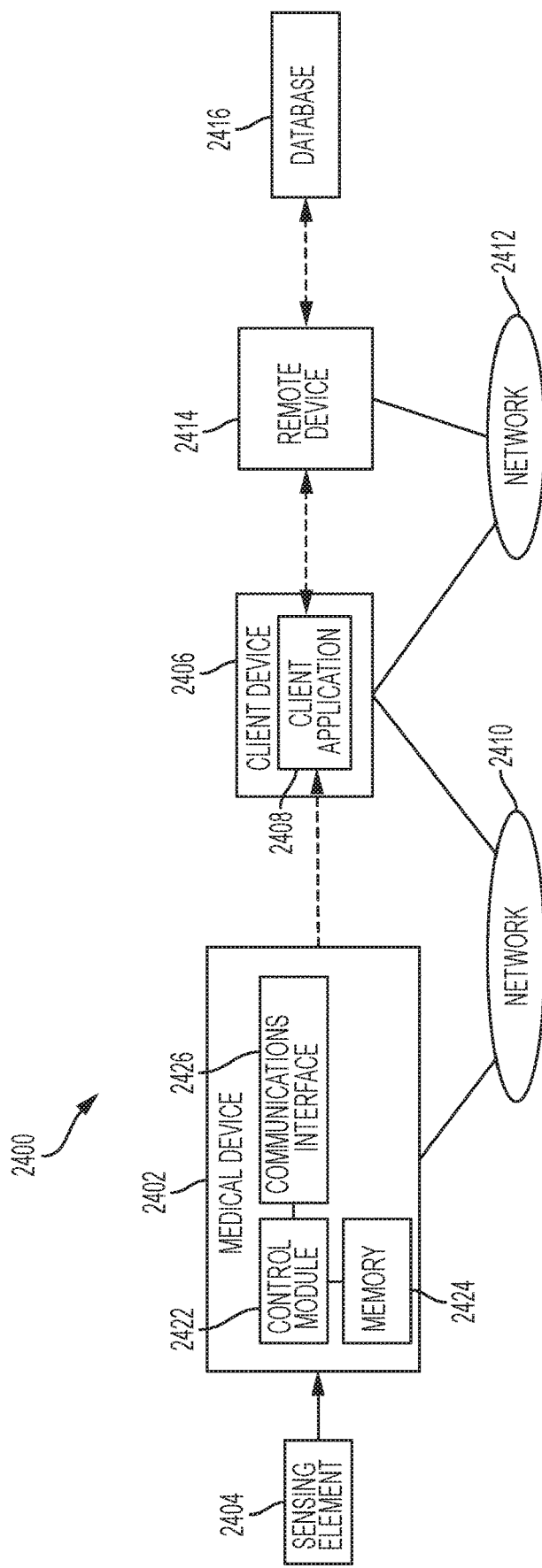
FIG. 24 is a block diagram of an exemplary patient monitoring system.

FIG. 24 depicts an exemplary embodiment of a patient monitoring system 2400 suitable for use with the subject matter described herein. The patient monitoring system 2400 includes a medical device 2402 that is communicatively coupled to a sensing element 2404 that is inserted into the body of a patient or otherwise worn by the patient to obtain measurement data indicative of a physiological condition in the body of the patient, such as a sensed glucose level. The medical device 2402 is communicatively coupled to a client device 2406 via a communications network 2410, with the client device 2406 being communicatively coupled to a remote device 2414 via another communications network 2412. In this regard, the client device 2406 may function as an intermediary for uploading or otherwise providing measurement data from the medical device 2402 to the remote device 2414 (e.g., server 102). It should be appreciated that FIG. 24 depicts a simplified representation of a patient monitoring system 2400 for purposes of explanation and is not intended to limit the subject matter described herein in any way.

In exemplary embodiments, the client device 2406 is realized as a mobile phone, a smartphone, a tablet computer, or other similar mobile electronic device; however, in other embodiments, the client device 2406 may be realized as any sort of electronic device capable of communicating with the medical device 2402 via network 2410, such as a laptop or notebook computer, a desktop computer, or the like. In exemplary embodiments, the network 2410 is realized as a Bluetooth network, a ZigBee network, or another suitable personal area network. That said, in other embodiments, the network 2410 could be realized as a wireless ad hoc network, a wireless local area network (WLAN), or local area network (LAN). The client device 2406 includes or is coupled to a display device, such as a monitor, screen, or another conventional electronic display, capable of graphically presenting data and/or information pertaining to the physiological condition of the patient. The client device 2406 also includes or is otherwise associated with a user input device, such as a keyboard, a mouse, a touchscreen, or the like, capable of receiving input data and/or other information from the user of the client device 2406.

In exemplary embodiments, a user, such as the patient, the patient's doctor or another healthcare provider, or the like, manipulates the client device 2406 to execute a client application 2408 that supports communicating with the medical device 2402 via the network 2410. In this regard, the client application 2408 supports establishing a communications session with the medical device 2402 on the network 2410 and receiving data and/or information from the medical device 2402 via the communications session. The medical device 2402 may similarly execute or otherwise implement a corresponding application or process that supports establishing the communications session with the client application 2408. The client application 2408 generally represents a software module or another feature that is generated or otherwise implemented by the client device 2406 to support the processes described herein. Accordingly, the client device 2406 generally includes a processing system and a data storage element (or memory) capable of storing programming instructions for execution by the processing system, that, when read and executed, cause processing system to create, generate, or otherwise facilitate the client application 2408 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random access memory (RAM), read only memory (ROM), flash memory, magnetic or optical mass storage, or any other suitable non-transitory short or long term data storage or other computer-readable media, and/or any suitable combination thereof.

In one or more embodiments, the client device 2406 and the medical device 2402 establish an association (or pairing) with one another over the network 2410 to support subsequently establishing a point-to-point or peer-to-peer communications session between the medical device 2402 and the client device 2406 via the network 2410. For example, in accordance with one embodiment, the network 2410 is realized as a Bluetooth network, wherein the medical device 2402 and the client device 2406 are paired with one another (e.g., by obtaining and storing network identification information for one another) by performing a discovery procedure or another suitable pairing procedure. The pairing information obtained during the discovery procedure allows either of the medical device 2402 or the client device 2406 to initiate the establishment of a secure communications session via the network 2410.

In one or more exemplary embodiments, the client application 2408 is also configured to store or otherwise maintain an address and/or other identification information for the remote device 2414 on the second network 2412. In this regard, the second network 2412 may be physically and/or logically distinct from the network 2410, such as, for example, the Internet, a cellular network, a wide area network (WAN), or the like. The remote device 2414 generally represents a server or other computing device configured to receive and analyze or otherwise monitor measurement data, event log data, and potentially other information obtained for the patient associated with the medical device 2402. In exemplary embodiments, the remote device 2414 is coupled to a database 2416 (e.g., database 104) configured to store or otherwise maintain data associated with individual patients. In practice, the remote device 2414 may reside at a location that is physically distinct and/or separate from the medical device 2402 and the client device 2406, such as, for example, at a facility that is owned and/or operated by or otherwise affiliated with a manufacturer of the medical device 2402. For purposes of explanation, but without limitation, the remote device 2414 may alternatively be referred to herein as a server.

Still referring to FIG. 24, the sensing element 2404 generally represents the component of the patient monitoring system 2400 that is configured to generate, produce, or otherwise output one or more electrical signals indicative of a physiological condition that is sensed, measured, or otherwise quantified by the sensing element 2404. In this regard, the physiological condition of a user influences a characteristic of the electrical signal output by the sensing element 2404, such that the characteristic of the output signal corresponds to or is otherwise correlative to the physiological condition that the sensing element 2404 is sensitive to. In exemplary embodiments, the sensing element 2404 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 2404.

The medical device 2402 generally represents the component of the patient monitoring system 2400 that is communicatively coupled to the output of the sensing element 2404 to receive or otherwise obtain the measurement data samples from the sensing element 2404 (e.g., the measured glucose and characteristic impedance values), store or otherwise maintain the measurement data samples, and upload or otherwise transmit the measurement data to the server 2414 via the client device 2406. In one or more embodiments, the medical device 2402 is realized as an infusion device 602, 2002 configured to deliver a fluid, such as insulin, to the body of the patient. That said, in other embodiments, the medical device 2402 could be a standalone sensing or monitoring device separate and independent from an infusion device (e.g., sensing arrangement 604, 2004). It should be noted that although FIG. 24 depicts the medical device 2402 and the sensing element 2404 as separate components, in practice, the medical device 2402 and the sensing element 2404 may be integrated or otherwise combined to provide a unitary device that can be worn by the patient.

In exemplary embodiments, the medical device 2402 includes a control module 2422, a data storage element 2424 (or memory), and a communications interface 2426. The control module 2422 generally represents the hardware, circuitry, logic, firmware and/or other component(s) of the medical device 2402 that is coupled to the sensing element 2404 to receive the electrical signals output by the sensing element 2404 and perform or otherwise support various additional tasks, operations, functions and/or processes described herein. Depending on the embodiment, the control module 2422 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 2422 includes an analog-to-digital converter (ADC) or another similar sampling arrangement that samples or otherwise converts an output electrical signal received from the sensing element 2404 into corresponding digital measurement data value. In other embodiments, the sensing element 2404 may incorporate an ADC and output a digital measurement value.

The communications interface 2426 generally represents the hardware, circuitry, logic, firmware and/or other components of the medical device 2402 that are coupled to the control module 2422 for outputting data and/or information from/to the medical device 2402 to/from the client device 2406. For example, the communications interface 2426 may include or otherwise be coupled to one or more transceiver modules capable of supporting wireless communications between the medical device 2402 and the client device 2406. In exemplary embodiments, the communications interface 2426 is realized as a Bluetooth transceiver or adapter configured to support Bluetooth Low Energy (BLE) communications.

In exemplary embodiments, the remote device 2414 receives, from the client device 2406, measurement data values associated with a particular patient (e.g., sensor glucose measurements, acceleration measurements, and the like) that were obtained using the sensing element 2404, and the remote device 2414 stores or otherwise maintains the historical measurement data in the database 2416 in association with the patient (e.g., using one or more unique patient identifiers). Additionally, the remote device 2414 may also receive, from or via the client device 2406, meal data or other event log data that may be input or otherwise provided by the patient (e.g., via client application 2408) and store or otherwise maintain historical meal data and other historical event or activity data associated with the patient in the database 2416. In this regard, the meal data include, for example, a time or timestamp associated with a particular meal event, a meal type or other information indicative of the content or nutritional characteristics of the meal, and an indication of the size associated with the meal. In exemplary embodiments, the remote device 2414 also receives historical fluid delivery data corresponding to basal or bolus dosages of fluid delivered to the patient by an infusion device 602, 2002. For example, the client application 2408 may communicate with an infusion device 602, 2002 to obtain insulin delivery dosage amounts and corresponding timestamps from the infusion device 602, 2002, and then upload the insulin delivery data to the remote device 2414 for storage in association with the particular patient. The remote device 2414 may also receive geolocation data and potentially other contextual data associated with a device 2402, 2406 from the client device 2406 and/or client application 2408, and store or otherwise maintain the historical operational context data in association with the particular patient. In this regard, one or more of the devices 2402, 2406 may include a global positioning system (GPS) receiver or similar modules, components or circuitry capable of outputting or otherwise providing data characterizing the geographic location of the respective device 2402, 2406 in real-time.

As described above, in one or more exemplary embodiments, the remote device 2414 utilizes machine learning to determine which combination of variables, fields, or attributes of the historical observational patient data are correlated to or predictive of the occurrence of a particular event, activity, or metric for a particular patient, and then determines a corresponding equation, function, or model for calculating the value of the parameter of interest based on that set of input variables. Thus, the resultant model is capable of characterizing or mapping a particular combination of one or more of the current (or recent) sensor glucose measurement data, auxiliary measurement data, delivery data, geographic location, patient behavior or activities, and the like to a value representative of the current probability or likelihood of a particular event or activity or a current value for a parameter of interest. It should be noted that since each patient's physiological response may vary from the rest of the population, the subset of input variables that are predictive of or correlative for a particular patient may vary from other users when the modeling is performed on a per-patient basis. Additionally, in such embodiments, the relative weightings applied to the respective variables of that predictive subset may also vary from other patients who may have common predictive subsets, based on differing correlations between a particular input variable and the historical data for that particular patient. It should be noted that any number of different machine learning techniques may be utilized by the remote device 2414 to determine what input variables are predictive for a current patient of interest, such as, for example, artificial neural networks, genetic programming, support vector machines, Bayesian networks, probabilistic machine learning models, or other Bayesian techniques, fuzzy logic, heuristically derived combinations, or the like.

Diabetes Data Management System Overview

Figure 25:
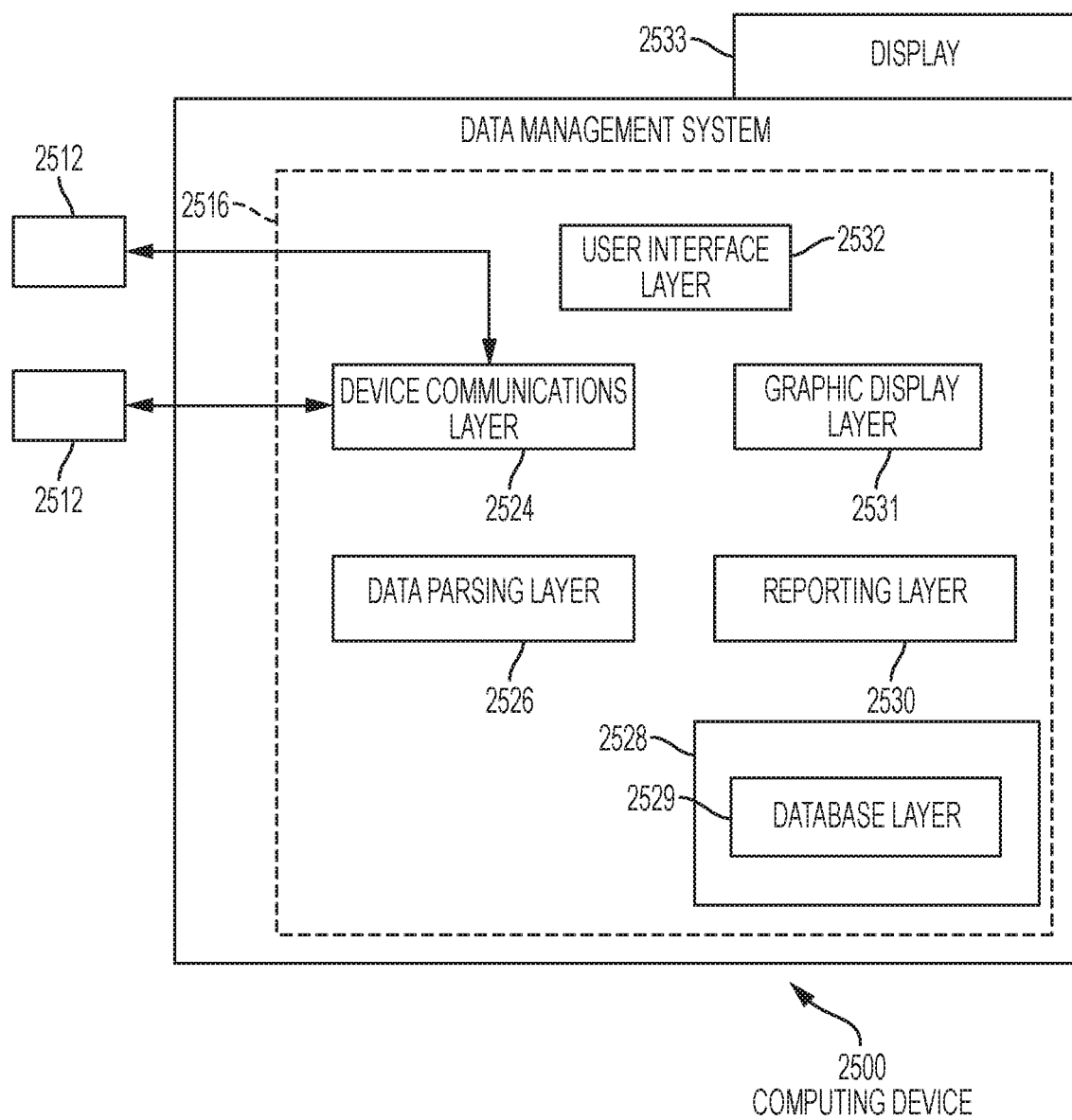
FIG. 25 depicts an embodiment of a computing device of a diabetes data management system suitable for use in connection with any one or more of the systems of FIGS. 1, 6, 20 and 24 and any one or more of the processes of FIGS. 2-3, 8, 11, 13 and 17-19 in accordance with one or more embodiments.

FIG. 25 illustrates a computing device 2500 suitable for use as part of a diabetes data management system in conjunction with one or more of the processes described above. The diabetes data management system (DDMS) may be referred to as the Medtronic MiniMed CARELINK™ system or as a medical data management system (MDMS) in some embodiments. The DDMS may be housed on a server or a plurality of servers which a user or a health care professional may access via a communications network via the Internet or the World Wide Web. Some models of the DDMS, which is described as an MDMS, are described in U.S. Patent Application Publication Nos. 2006/0031094 and 2013/0338630, which is herein incorporated by reference in their entirety.

While descriptions of embodiments are made in regard to monitoring medical or biological conditions for subjects having diabetes, the systems and processes herein are applicable to monitoring medical or biological conditions for cardiac subjects, cancer subjects, HIV subjects, subjects with other disease, infection, or controllable conditions, or various combinations thereof.

In embodiments of the invention, the DDMS may be installed in a computing device in a health care provider's office, such as a doctor's office, a nurse's office, a clinic, an emergency room, an urgent care office. Health care providers may be reluctant to utilize a system where their confidential patient data is to be stored in a computing device such as a server on the Internet.

The DDMS may be installed on a computing device 2500. The computing device 2500 may be coupled to a display 2533. In some embodiments, the computing device 2500 may be in a physical device separate from the display (such as in a personal computer, a mini-computer, etc.) In some embodiments, the computing device 2500 may be in a single physical enclosure or device with the display 2533 such as a laptop where the display 2533 is integrated into the computing device. In embodiments of the invention, the computing device 2500 hosting the DDMS may be, but is not limited to, a desktop computer, a laptop computer, a server, a network computer, a personal digital assistant (PDA), a portable telephone including computer functions, a pager with a large visible display, an insulin pump including a display, a glucose sensor including a display, a glucose meter including a display, and/or a combination insulin pump/glucose sensor having a display. The computing device may also be an insulin pump coupled to a display, a glucose meter coupled to a display, or a glucose sensor coupled to a display. The computing device 2500 may also be a server located on the Internet that is accessible via a browser installed on a laptop computer, desktop computer, a network computer, or a PDA. The computing device 2500 may also be a server located in a doctor's office that is accessible via a browser installed on a portable computing device, e.g., laptop, PDA, network computer, portable phone, which has wireless capabilities and can communicate via one of the wireless communication protocols such as Bluetooth and IEEE 802.11 protocols.

In the embodiment shown in FIG. 25, the data management system 2516 comprises a group of interrelated software modules or layers that specialize in different tasks. The system software includes a device communication layer 2524, a data parsing layer 2526, a database layer 2528, database storage devices 2529, a reporting layer 2530, a graph display layer 2531, and a user interface layer 2532. The diabetes data management system may communicate with a plurality of subject support devices 2512, two of which are illustrated in FIG. 25. Although the different reference numerals refer to a number of layers, (e.g., a device communication layer, a data parsing layer, a database layer), each layer may include a single software module or a plurality of software modules. For example, the device communications layer 2524 may include a number of interacting software modules, libraries, etc. In embodiments of the invention, the data management system 2516 may be installed onto a non-volatile storage area (memory such as flash memory, hard disk, removable hard, DVD-RW, CD-RW) of the computing device 2500. If the data management system 2516 is selected or initiated, the system 2516 may be loaded into a volatile storage (memory such as DRAM, SRAM, RAM, DDRAM) for execution.

The device communication layer 2524 is responsible for interfacing with at least one, and, in further embodiments, to a plurality of different types of subject support devices 2512, such as, for example, blood glucose meters, glucose sensors/monitors, or an infusion pump. In one embodiment, the device communication layer 2524 may be configured to communicate with a single type of subject support device 2512. However, in more comprehensive embodiments, the device communication layer 2524 is configured to communicate with multiple different types of subject support devices 2512, such as devices made from multiple different manufacturers, multiple different models from a particular manufacturer and/or multiple different devices that provide different functions (such as infusion functions, sensing functions, metering functions, communication functions, user interface functions, or combinations thereof). By providing an ability to interface with multiple different types of subject support devices 2512, the diabetes data management system 2516 may collect data from a significantly greater number of discrete sources. Such embodiments may provide expanded and improved data analysis capabilities by including a greater number of subjects and groups of subjects in statistical or other forms of analysis that can benefit from larger amounts of sample data and/or greater diversity in sample data, and, thereby, improve capabilities of determining appropriate treatment parameters, diagnostics, or the like.

The device communication layer 2524 allows the DDMS 2516 to receive information from and transmit information to or from each subject support device 2512 in the system 2516. Depending upon the embodiment and context of use, the type of information that may be communicated between the system 2516 and device 2512 may include, but is not limited to, data, programs, updated software, education materials, warning messages, notifications, device settings, therapy parameters, or the like. The device communication layer 2524 may include suitable routines for detecting the type of subject support device 2512 in communication with the system 2516 and implementing appropriate communication protocols for that type of device 2512. Alternatively or in addition, the subject support device 2512 may communicate information in packets or other data arrangements, where the communication includes a preamble or other portion that includes device identification information for identifying the type of the subject support device. Alternatively, or in addition, the subject support device 2512 may include suitable user-operable interfaces for allowing a user to enter information (e.g., by selecting an optional icon or text or other device identifier) that corresponds to the type of subject support device used by that user. Such information may be communicated to the system 2516, through a network connection. In yet further embodiments, the system 2516 may detect the type of subject support device 2512 it is communicating with in the manner described above and then may send a message requiring the user to verify that the system 2516 properly detected the type of subject support device being used by the user. For systems 2516 that are capable of communicating with multiple different types of subject support devices 2512, the device communication layer 2524 may be capable of implementing multiple different communication protocols and selects a protocol that is appropriate for the detected type of subject support device.

The data-parsing layer 2526 is responsible for validating the integrity of device data received and for inputting it correctly into a database 2529. A cyclic redundancy check CRC process for checking the integrity of the received data may be employed. Alternatively, or in addition, data may be received in packets or other data arrangements, where preambles or other portions of the data include device type identification information. Such preambles or other portions of the received data may further include device serial numbers or other identification information that may be used for validating the authenticity of the received information. In such embodiments, the system 2516 may compare received identification information with pre-stored information to evaluate whether the received information is from a valid source.

The database layer 2528 may include a centralized database repository that is responsible for warehousing and archiving stored data in an organized format for later access, and retrieval. The database layer 2528 operates with one or more data storage device(s) 2529 suitable for storing and providing access to data in the manner described herein. Such data storage device(s) 2529 may comprise, for example, one or more hard discs, optical discs, tapes, digital libraries or other suitable digital or analog storage media and associated drive devices, drive arrays or the like.

Data may be stored and archived for various purposes, depending upon the embodiment and environment of use. Information regarding specific subjects and patient support devices may be stored and archived and made available to those specific subjects, their authorized healthcare providers and/or authorized healthcare payor entities for analyzing the subject's condition. Also, certain information regarding groups of subjects or groups of subject support devices may be made available more generally for healthcare providers, subjects, personnel of the entity administering the system 2516 or other entities, for analyzing group data or other forms of conglomerate data.

Embodiments of the database layer 2528 and other components of the system 2516 may employ suitable data security measures for securing personal medical information of subjects, while also allowing non-personal medical information to be more generally available for analysis. Embodiments may be configured for compliance with suitable government regulations, industry standards, policies or the like, including, but not limited to the Health Insurance Portability and Accountability Act of 1996 (HIPAA).

The database layer 2528 may be configured to limit access of each user to types of information pre-authorized for that user. For example, a subject may be allowed access to his or her individual medical information (with individual identifiers) stored by the database layer 2528, but not allowed access to other subject's individual medical information (with individual identifiers). Similarly, a subject's authorized healthcare provider or payor entity may be provided access to some or all of the subject's individual medical information (with individual identifiers) stored by the database layer 2528, but not allowed access to another individual's personal information. Also, an operator or administrator-user (on a separate computer communicating with the computing device 2500) may be provided access to some or all subject information, depending upon the role of the operator or administrator. On the other hand, a subject, healthcare provider, operator, administrator or other entity, may be authorized to access general information of unidentified individuals, groups or conglomerates (without individual identifiers) stored by the database layer 2528 in the data storage devices 2529.

In exemplary embodiments, the database 2529 stores uploaded measurement data for a patient (e.g., sensor glucose measurement and characteristic impedance values) along with event log data consisting of event records created during a monitoring period corresponding to the measurement data. In embodiments of the invention, the database layer 2528 may also store preference profiles. In the database layer 2528, for example, each user may store information regarding specific parameters that correspond to the user. Illustratively, these parameters could include target blood glucose or sensor glucose levels, what type of equipment the users utilize (insulin pump, glucose sensor, blood glucose meter, etc.) and could be stored in a record, a file, or a memory location in the data storage device(s) 2529 in the database layer. Preference profiles may include various threshold values, monitoring period values, prioritization criteria, filtering criteria, and/or other user-specific values for parameters to generate a snapshot GUI display on the display 2533 or a support device 2512 in a personalized or patient-specific manner.

The DDMS 2516 may measure, analyze, and track either blood glucose (BG) or sensor glucose (SG) measurements (or readings) for a user. In embodiments of the invention, the medical data management system may measure, track, or analyze both BG and SG readings for the user. Accordingly, although certain reports may mention or illustrate BG or SG only, the reports may monitor and display results for the other one of the glucose readings or for both of the glucose readings.

The reporting layer 2530 may include a report wizard program that pulls data from selected locations in the database 2529 and generates report information from the desired parameters of interest. The reporting layer 2530 may be configured to generate multiple different types of reports, each having different information and/or showing information in different formats (arrangements or styles), where the type of report may be selectable by the user. A plurality of pre-set types of report (with pre-defined types of content and format) may be available and selectable by a user. At least some of the pre-set types of reports may be common, industry standard report types with which many healthcare providers should be familiar. In exemplary embodiments described herein, the reporting layer 2530 also facilitates generation of a snapshot report including a snapshot GUI display.

In embodiments of the invention, the database layer 2528 may calculate values for various medical information that is to be displayed on the reports generated by the report or reporting layer 2530. For example, the database layer 2528, may calculate average blood glucose or sensor glucose readings for specified timeframes. In embodiments of the invention, the reporting layer 2530 may calculate values for medical or physical information that is to be displayed on the reports. For example, a user may select parameters which are then utilized by the reporting layer 2530 to generate medical information values corresponding to the selected parameters. In other embodiments of the invention, the user may select a parameter profile that previously existed in the database layer 2528.

Alternatively, or in addition, the report wizard may allow a user to design a custom type of report. For example, the report wizard may allow a user to define and input parameters (such as parameters specifying the type of content data, the time period of such data, the format of the report, or the like) and may select data from the database and arrange the data in a printable or displayable arrangement, based on the user-defined parameters. In further embodiments, the report wizard may interface with or provide data for use by other programs that may be available to users, such as common report generating, formatting or statistical analysis programs. In this manner, users may import data from the system 2516 into further reporting tools familiar to the user. The reporting layer 2530 may generate reports in displayable form to allow a user to view reports on a standard display device, printable form to allow a user to print reports on standard printers, or other suitable forms for access by a user. Embodiments may operate with conventional file format schemes for simplifying storing, printing and transmitting functions, including, but not limited to PDF, JPEG, or the like. Illustratively, a user may select a type of report and parameters for the report and the reporting layer 2530 may create the report in a PDF format. A PDF plug-in may be initiated to help create the report and also to allow the user to view the report. Under these operating conditions, the user may print the report utilizing the PDF plug-in. In certain embodiments in which security measures are implemented, for example, to meet government regulations, industry standards or policies that restrict communication of subject's personal information, some or all reports may be generated in a form (or with suitable software controls) to inhibit printing, or electronic transfer (such as a non-printable and/or non-capable format). In yet further embodiments, the system 2516 may allow a user generating a report to designate the report as non-printable and/or non-transferable, whereby the system 2516 will provide the report in a form that inhibits printing and/or electronic transfer.

The reporting layer 2530 may transfer selected reports to the graph display layer 2531. The graph display layer 2531 receives information regarding the selected reports and converts the data into a format that can be displayed or shown on a display 2533.

In embodiments of the invention, the reporting layer 2530 may store a number of the user's parameters. Illustratively, the reporting layer 2530 may store the type of carbohydrate units, a blood glucose movement or sensor glucose reading, a carbohydrate conversion factor, and timeframes for specific types of reports. These examples are meant to be illustrative and not limiting.

Data analysis and presentations of the reported information may be employed to develop and support diagnostic and therapeutic parameters. Where information on the report relates to an individual subject, the diagnostic and therapeutic parameters may be used to assess the health status and relative well-being of that subject, assess the subject's compliance to a therapy, as well as to develop or modify treatment for the subject and assess the subject's behaviors that affect his/her therapy. Where information on the report relates to groups of subjects or conglomerates of data, the diagnostic and therapeutic parameters may be used to assess the health status and relative well-being of groups of subjects with similar medical conditions, such as, but not limited to, diabetic subjects, cardiac subjects, diabetic subjects having a particular type of diabetes or cardiac condition, subjects of a particular age, sex or other demographic group, subjects with conditions that influence therapeutic decisions such as but not limited to pregnancy, obesity, hypoglycemic unawareness, learning disorders, limited ability to care for self, various levels of insulin resistance, combinations thereof, or the like.

The user interface layer 2532 supports interactions with the end user, for example, for user login and data access, software navigation, data input, user selection of desired report types and the display of selected information. Users may also input parameters to be utilized in the selected reports via the user interface layer 2532. Examples of users include but are not limited to: healthcare providers, healthcare payer entities, system operators or administrators, researchers, business entities, healthcare institutions and organizations, or the like, depending upon the service being provided by the system and depending upon the invention embodiment. More comprehensive embodiments are capable of interacting with some or all of the above-noted types of users, wherein different types of users have access to different services or data or different levels of services or data.

In an example embodiment, the user interface layer 2532 provides one or more websites accessible by users on the Internet. The user interface layer may include or operate with at least one (or multiple) suitable network server(s) to provide the website(s) over the Internet and to allow access, world-wide, from Internet-connected computers using standard Internet browser software. The website(s) may be accessed by various types of users, including but not limited to subjects, healthcare providers, researchers, business entities, healthcare institutions and organizations, payor entities, pharmaceutical partners or other sources of pharmaceuticals or medical equipment, and/or support personnel or other personnel running the system 2516, depending upon the embodiment of use.

In another example embodiment, where the DDMS 2516 is located on one computing device 2500, the user interface layer 2532 provides a number of menus to the user to navigate through the DDMS. These menus may be created utilizing any menu format, including but not limited to HTML, XML, or Active Server pages. A user may access the DDMS 2516 to perform one or more of a variety of tasks, such as accessing general information made available on a website to all subjects or groups of subjects. The user interface layer 2532 of the DDMS 2516 may allow a user to access specific information or to generate reports regarding that subject's medical condition or that subject's medical device(s) 2512, to transfer data or other information from that subject's support device(s) 2512 to the system 2516, to transfer data, programs, program updates or other information from the system 2516 to the subject's support device(s) 2512, to manually enter information into the system 2516, to engage in a remote consultation exchange with a healthcare provider, or to modify the custom settings in a subject's supported device and/or in a subject's DDMS/MDMS data file.

The system 2516 may provide access to different optional resources or activities (including accessing different information items and services) to different users and to different types or groups of users, such that each user may have a customized experience and/or each type or group of user (e.g., all users, diabetic users, cardio users, healthcare provider-user or payor-user, or the like) may have a different set of information items or services available on the system. The system 2516 may include or employ one or more suitable resource provisioning program or system for allocating appropriate resources to each user or type of user, based on a pre-defined authorization plan. Resource provisioning systems are well known in connection with provisioning of electronic office resources (email, software programs under license, sensitive data, etc.) in an office environment, for example, in a local area network LAN for an office, company or firm. In one example embodiment, such resource provisioning systems is adapted to control access to medical information and services on the DDMS 2516, based on the type of user and/or the identity of the user.

Upon entering successful verification of the user's identification information and password, the user may be provided access to secure, personalized information stored on the DDMS 2516. For example, the user may be provided access to a secure, personalized location in the DDMS 2516 which has been assigned to the subject. This personalized location may be referred to as a personalized screen, a home screen, a home menu, a personalized page, etc. The personalized location may provide a personalized home screen to the subject, including selectable icons or menu items for selecting optional activities, including, for example, an option to transfer device data from a subject's supported device 2512 to the system 2516, manually enter additional data into the system 2516, modify the subject's custom settings, and/or view and print reports. Reports may include data specific to the subject's condition, including but not limited to, data obtained from the subject's subject support device(s) 2512, data manually entered, data from medical libraries or other networked therapy management systems, data from the subjects or groups of subjects, or the like. Where the reports include subject-specific information and subject identification information, the reports may be generated from some or all subject data stored in a secure storage area (e.g., storage devices 2529) employed by the database layer 2528.

The user may select an option to transfer (send) device data to the medical data management system 2516. If the system 2516 receives a user's request to transfer device data to the system, the system 2516 may provide the user with step-by-step instructions on how to transfer data from the subject's supported device(s) 2512. For example, the DDMS 2516 may have a plurality of different stored instruction sets for instructing users how to download data from different types of subject support devices, where each instruction set relates to a particular type of subject supported device (e.g., pump, sensor, meter, or the like), a particular manufacturer's version of a type of subject support device, or the like. Registration information received from the user during registration may include information regarding the type of subject support device(s) 2512 used by the subject. The system 2516 employs that information to select the stored instruction set(s) associated with the particular subject's support device(s) 2512 for display to the user.

Other activities or resources available to the user on the system 2516 may include an option for manually entering information to the DDMS/MDMS 2516. For example, from the user's personalized menu or location, the user may select an option to manually enter additional information into the system 2516.

Further optional activities or resources may be available to the user on the DDMS 2516. For example, from the user's personalized menu, the user may select an option to receive data, software, software updates, treatment recommendations or other information from the system 2516 on the subject's support device(s) 2512. If the system 2516 receives a request from a user to receive data, software, software updates, treatment recommendations or other information, the system 2516 may provide the user with a list or other arrangement of multiple selectable icons or other indicia representing available data, software, software updates or other information available to the user.

Yet further optional activities or resources may be available to the user on the medical data management system 2516 including, for example, an option for the user to customize or otherwise further personalize the user's personalized location or menu. In particular, from the user's personalized location, the user may select an option to customize parameters for the user. In addition, the user may create profiles of customizable parameters. When the system 2516 receives such a request from a user, the system 2516 may provide the user with a list or other arrangement of multiple selectable icons or other indicia representing parameters that may be modified to accommodate the user's preferences. When a user selects one or more of the icons or other indicia, the system 2516 may receive the user's request and makes the requested modification.

In one or more exemplary embodiments, for an individual patient in the DDMS, the computing device 2500 of the DDMS is configured to analyze that patient's historical measurement data, historical delivery data, historical event log data, and any other historical or contextual data associated with the patient maintained in the database layer 2528 to support one or more of the processes described herein. In this regard, machine learning, artificial intelligence, or similar mathematical modeling of the patient's physiological behavior or response may be performed at the computing device 2500 to facilitate patient-specific correlations or predictions. Current measurement data, delivery data, and event log data associated with the patient along with current contextual data may be analyzed using the resultant models, either at the computing device 2500 of the DDMS or another device 2512 to determine predictions or other probable events, behaviors, or outcomes pertaining to a patient in real-time.

For the sake of brevity, conventional techniques related to glucose sensing and/or monitoring, sensor calibration and/or compensation, bolusing, machine learning and/or artificial intelligence, pharmodynamic modeling, and other functional aspects of the subject matter may not be described in detail herein. In addition, certain terminology may also be used in the herein for the purpose of reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of monitoring a physiological condition of a patient, the method comprising:

obtaining, at a computing device, current measurement data for the physiological condition of the patient provided by a sensing arrangement;

obtaining, at the computing device, a user input indicative of one or more future events associated with the patient; and in response to the user input:

determining a prediction of the physiological condition of the patient in the future based at least in part on the current measurement data and the one or more future events using one or more prediction models associated with the patient, wherein determining the prediction comprises:

determining hourly forecast values for the physiological condition using an hourly forecasting model associated with the patient based at least in part on the current measurement data and the one or more future events, the hourly forecasting model comprising a neural network including a plurality of cells, wherein each cell corresponds to a respective hourly interval and at least one of the plurality of cells is configured to output an average value for the physiological condition during the respective hourly interval in the future based at least in part on a subset of the one or more future events predicted to occur within the respective hourly interval in the future;

determining a second plurality of predicted values for the physiological condition of the patient in the future based at least in part on the current measurement data using a second prediction model different from the hourly forecasting model;

determining, for each of the hourly forecasting model and the second prediction model, a weighting factor associated with the respective prediction model based at least in part on the one or more future events; and determining an ensemble prediction for the physiological condition of the patient with respect to time in the future based at least in part on the hourly forecast values, the second plurality of predicted values, and respective weighting factors associated with the hourly forecasting model and the second prediction model; and displaying, at the computing device, a graphical representation of the ensemble prediction with respect to time on a display device.

2. The method of claim 1, wherein:

the weighting factors vary with respect to an amount of time in the future based on a relationship between a first reliability metric associated with the hourly forecast model and a second reliability metric associated with the second prediction model; and the first and second reliability metrics are influenced by the one or more future events.

3. The method of claim 1, further comprising obtaining, from a second sensing arrangement, contextual measurement data, wherein determining the hourly forecast values comprises determining the hourly forecast values based at least in part on the current measurement data, the one or more future events, and the contextual measurement data.

4. The method of claim 1, wherein determining the second plurality of predicted values comprises determining predicted sample values for the physiological condition using at least one of an autoregressive integrated moving average model determined based on historical data associated with the patient or a physiological model determined based on historical data associated with the patient.

5. The method of claim 4, wherein the ensemble prediction comprises a weighted average of the hourly forecast values weighted using a first weighting factor and the second plurality of predicted values weighted using a second weighting factor.

6. The method of claim 1, wherein:

obtaining the current measurement data comprises receiving sensor glucose measurement data from a glucose sensing arrangement;

obtaining the user input comprises receiving, via a user interface at the computing device, at least one of a prospective amount of carbohydrates to be consumed by the patient, a prospective amount of exercise to be performed by the patient, and a prospective bolus amount of insulin to be administered;

determining the ensemble prediction comprises determining an ensemble prediction of a glucose level of the patient in the future based at least in part on the sensor glucose measurement data and the one or more future events using a plurality of prediction models associated with the patient; and displaying the graphical representation of the ensemble prediction comprises displaying a graphical representation of the ensemble prediction of the glucose level of the patient in the future with respect to time.

7. The method of claim 6, wherein determining the ensemble prediction comprises:

determining the hourly forecast values for the glucose level of the patient in the future based at least in part on the sensor glucose measurement data using the hourly forecasting model associated with the patient;

determining the second plurality of predicted values for the glucose level of the patient in the future based at least in part on the sensor glucose measurement data using the second prediction model;

determining a first weighting factor associated with the hourly forecasting model based at least in part on the one or more future events;

determining a second weighting factor associated with the second prediction model based at least in part on the one or more future events; and determining the ensemble prediction as a weighted average of the hourly forecast values and the second plurality of predicted values using the first and second weighting factors.

8. The method of claim 1, further comprising providing, on the display device, a graphical user interface display prompting conversational interaction by the patient, wherein:

obtaining the user input comprises receiving a conversational input indicative of the one or more future events from the patient; and displaying the graphical representation of the ensemble prediction comprises providing graphical representation of the ensemble prediction within the graphical user interface display responsive to the conversational input.

9. A non-transitory computer-readable medium having instructions stored thereon that are executable by a processing system to perform a method comprising:

obtaining current measurement data for a physiological condition of a patient provided by a sensing arrangement;

obtaining a user input indicative of one or more future events associated with the patient; and in response to the user input:

determining a prediction of the physiological condition of the patient in the future based at least in part on the current measurement data and the one or more future events using one or more prediction models associated with the patient, wherein determining the prediction comprises:

determining hourly forecast values for the physiological condition using an hourly forecasting model associated with the patient based at least in part on the current measurement data and the one or more future events, the hourly forecasting model comprising a neural network including a plurality of cells, wherein each cell corresponds to a respective hourly interval and at least one of the plurality of cells is configured to output an average value for the physiological condition during the respective hourly interval in the future based at least in part on a subset of the one or more future events predicted to occur within the respective hourly interval in the future;

determining a second plurality of predicted values for the physiological condition of the patient in the future based at least in part on the current measurement data using a second prediction model different from the hourly forecasting model;

determining, for each of the hourly forecasting model and the second prediction model, a weighting factor associated with the respective prediction model based at least in part on the one or more future events; and determining an ensemble prediction for the physiological condition of the patient with respect to time in the future based at least in part on the hourly forecast values, the second plurality of predicted values, and respective weighting factors associated with the hourly forecasting model and the second prediction model; and displaying a graphical representation of the ensemble prediction with respect to time on a display device.

10. An electronic device comprising:

a communications interface to receive current measurement data for a physiological condition of a patient from a sensing arrangement;

a display device having a graphical user interface display presented thereon;

a user interface to obtain a user input indicative of one or more future events; and a control system coupled to the communications interface, the display device, and the user interface to determine hourly forecast values for the physiological condition using an hourly forecasting model associated with the patient based at least in part on the current measurement data and the one or more future events, determine a second plurality of predicted values for the physiological condition of the patient in the future based at least in part on the current measurement data using a second prediction model different from the hourly forecasting model, determine, for each of the hourly forecasting model and the second prediction model, a weighting factor associated with the respective prediction model based at least in part on the one or more future events, determine an ensemble prediction of the physiological condition of the patient in the future based at least in part on the hourly forecast values, the second plurality of predicted values and respective weighting factors associated with the hourly forecasting model and the second prediction model, and display a graphical representation of the ensemble prediction within the graphical user interface display on the display device, wherein:

the hourly forecasting model comprises a neural network including a plurality of cells;

each cell corresponds to a respective hourly interval; and at least one of the plurality of cells is configured to output an average value for the physiological condition during the respective hourly interval in the future based at least in part on a subset of the one or more future events predicted to occur within the respective hourly interval in the future.

11. The electronic device of claim 10, wherein:

the ensemble prediction comprises a weighted average of the hourly forecast values and the second plurality of predicted values determined using the second prediction model; and the respective weighting factors associated with the hourly forecast model and the second prediction model vary with respect to time in the future based at least in part on the one or more future events and a relationship between a first reliability metric associated with the hourly forecast model and a second reliability metric associated with the second prediction model.

12. The electronic device of claim 10, wherein:

the current measurement data comprises sensor glucose measurement data from a glucose sensing arrangement;

the one or more future events comprise at least one of a prospective amount of carbohydrates to be consumed by the patient, a prospective amount of exercise to be performed by the patient, and a prospective bolus amount of insulin to be administered; and the ensemble prediction comprises a simulated glucose level.

13. The electronic device of claim 10, the graphical user interface display prompting conversational interaction, wherein:

the user input comprises a conversational input indicative of the one or more future events from the patient; and the graphical representation of the ensemble prediction is provided within the graphical user interface display responsive to the conversational input.

\* \* \* \* \*